United States Patent
Rogers et al.

(10) Patent No.: US 11,786,168 B2
(45) Date of Patent: Oct. 17, 2023

(54) EPIDERMAL SENSING SYSTEMS FOR OPTICAL READOUT, VISUALIZATION AND ANALYSIS OF BIOFLUIDS

(71) Applicants: NORTHWESTERN UNIVERSITY, Evanston, IL (US); THE BOARD OF TRUSTEES OF THE UNIVERSITY OF ILLINOIS, Urbana, IL (US)

(72) Inventors: John A. Rogers, Wilmette, IL (US); Johnathan T. Reeder, Plano, TX (US); Amay J. Bandodkar, Evanston, IL (US); Sungbong Kim, Champaign, IL (US); Yurina Sekine, Evanston, IL (US); Jungil Choi, Chicago, IL (US); Tyler R. Ray, Evanston, IL (US); Aurelie Hourlier-Fargette, Evanston, IL (US); Philipp Gutruf, Evanston, IL (US); Kun Hyuck Lee, Evanston, IL (US); Milan Raj, Evanston, IL (US)

(73) Assignees: NORTHWESTERN UNIVERSITY, Evanston, IL (US); THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 698 days.

(21) Appl. No.: 16/616,898

(22) PCT Filed: Jun. 1, 2018

(86) PCT No.: PCT/US2018/035738
§ 371 (c)(1),
(2) Date: Nov. 25, 2019

(87) PCT Pub. No.: WO2018/223090
PCT Pub. Date: Dec. 6, 2018

(65) Prior Publication Data
US 2021/0145352 A1 May 20, 2021

Related U.S. Application Data

(60) Provisional application No. 62/514,468, filed on Jun. 2, 2017, provisional application No. 62/514,520, filed
(Continued)

(51) Int. Cl.
*A61B 5/00* (2006.01)
*A61B 5/1455* (2006.01)
(Continued)

(52) U.S. Cl.
CPC .......... *A61B 5/4266* (2013.01); *A61B 5/0022* (2013.01); *A61B 5/01* (2013.01);
(Continued)

(58) Field of Classification Search
CPC .............. A61B 5/14517; A61B 5/4266; A61B 5/14532; A61B 5/14539; A61B 5/14546; A61B 5/1455
See application file for complete search history.

(56) References Cited

U.S. PATENT DOCUMENTS 4,960,467 A   10/1990  Peck
6,198,953 B1   3/2001  Webster et al.
(Continued)

FOREIGN PATENT DOCUMENTS

JP   2011-506953 A   3/2011
WO   2009025698 A1   2/2009
(Continued)

OTHER PUBLICATIONS

Ahyeon Koh et al., A soft, wearable microfluidic device for the capture, storage, and colorimetric sensing of sweat, Sci. Transl. Med., 2016.
(Continued)

*Primary Examiner* — Eric F Winakur
(74) *Attorney, Agent, or Firm* — Locke Lord LLP; Tim Tingkang Xia, Esq.

(57) ABSTRACT

The invention provides a versatile sensing platform for sensing and analysis of biofluids, particularly well-suited for sensing and analysis of sweat. Systems of the invention
(Continued)

allows for sensitive and selective detection of a range of analytes in sweat including metabolites, electrolytes and biomarkers. Systems of the invention provide a noninvasive and accurate means for quantitative characterization of important sweat characteristics including sweat volume, sweat loss and sweat rate. Systems of the invention are compatible with materials and device geometries for important class of conformal tissue mounted electronic devices, including epidermal electronic devices.

41 Claims, 53 Drawing Sheets

Related U.S. Application Data on Jun. 2, 2017, provisional application No. 62/514,374, filed on Jun. 2, 2017, provisional application No. 62/514,455, filed on Jun. 2, 2017, provisional application No. 62/514,546, filed on Jun. 2, 2017, provisional application No. 62/514,515, filed on Jun. 2, 2017, provisional application No. 62/514,559, filed on Jun. 2, 2017, provisional application No. 62/514,489, filed on Jun. 2, 2017, provisional application No. 62/514,436, filed on Jun. 2, 2017.

(51) Int. Cl.
| | | |
|---|---|---|
| *A61B 5/1486* | (2006.01) | |
| *A61B 5/145* | (2006.01) | |
| *A61B 5/1477* | (2006.01) | |
| *A61B 5/01* | (2006.01) | |
| *A61B 5/103* | (2006.01) | |

(52) U.S. Cl.
CPC .......... *A61B 5/1032* (2013.01); *A61B 5/1455* (2013.01); *A61B 5/1477* (2013.01); *A61B 5/1486* (2013.01); *A61B 5/14517* (2013.01); *A61B 5/14532* (2013.01); *A61B 5/14539* (2013.01); *A61B 5/14546* (2013.01); *A61B 2562/0242* (2013.01); *A61B 2562/0276* (2013.01); *A61B 2562/164* (2013.01)

(56) References Cited

U.S. PATENT DOCUMENTS

| 7,927,865 | B2 | 4/2011 | Meathrel et al. |
| 2006/0253011 | A1 | 11/2006 | Edmonson et al. |
| 2007/0027383 | A1 | 2/2007 | Peyser et al. |
| 2007/0179371 | A1 | 8/2007 | Peyser et al. |
| 2010/0179403 | A1 | 7/2010 | Martinsen et al. |
| 2015/0094219 | A1 | 4/2015 | Trowell et al. |
| 2015/0112165 | A1 | 4/2015 | Heikenfeld |
| 2017/0055890 | A1* | 3/2017 | Kube ................. A61B 5/14532 |
| 2017/0059563 | A1 | 3/2017 | Smith et al. |

FOREIGN PATENT DOCUMENTS

| WO | 2010030609 A1 | 3/2010 |
| WO | 2016025430 A1 | 2/2016 |
| WO | 2016025438 A1 | 2/2016 |
| WO | 2016025468 A2 | 2/2016 |
| WO | 2017218878 A1 | 12/2017 |

OTHER PUBLICATIONS

Jungil Choi et al., Thin, Soft, Skin-Mounted Microfluidic Networks with Capillary Bursting Valves for Chrono-Sampling of Sweat, Adv. Healthcare Mater., 2017.

EPO, "Supplementary Partial European Search Report for EP Application No. 18809483.3", Munich, Germany, dated Mar. 17, 2021.

JPO, "First Office Action for JP Application No. 2019-566631", Japan, dated Mar. 8, 2021.

United States Patent and Trademark Office (ISR/US) "International Search Report for PCT/US2018/035738", U.S., dated Oct. 2018.

\* cited by examiner

EPIDERMAL SENSING SYSTEMS FOR OPTICAL READOUT, VISUALIZATION AND ANALYSIS OF BIOFLUIDS

CROSS-REFERENCE TO RELATED APPLICATIONS

This application claims the benefit of priority to U.S. Provisional Patent Application Nos. 62/514,489, filed Jun. 2, 2017, 62/514,515, filed Jun. 2, 2017, 62/514,374, filed Jun. 2, 2017, 62/514,455, filed Jun. 2, 2017, 62/514,520, filed Jun. 2, 2017, 62/514,468, filed Jun. 2, 2017, 62/514,546, filed Jun. 2, 2017, 62/514,559, filed Jun. 2, 2017, and 62/514,436, filed Jun. 2, 2017, all of which are hereby incorporated by reference in their entirety.

BACKGROUND OF INVENTION

Microfluidics provides a versatile technology platform impacting a wide range of industries and commercial products. In the field of medical diagnostics, for example, microfluidics has been essential to the development of entirely new classes of sensors and assays with potential for revolutionizing medical diagnosis and the treatment of disease. Lab on a chip and microarray systems, for example, have been developed for clinical pathology taking advantage of microfluidic sample collection, preparation and handling to achieve highly sensitivity and rapid point of care analysis of biomarkers in minute quantities of biofluid. The advances in microfluidics have also been leveraged to support other biotechnology and medical applications including high throughput DNA sequencing, mass spectrometry-based proteomics, cellular expression and imaging.

Wearable systems are another technology for which advances in microfluidics has potential to enable new classes of products and advanced modes of functionality. Recent developments in epidermal electronics, for example, provide a class of skin-mounted sensors and actuators compatible with efficient microfluidic sampling at the interface of the skin. Such microfluidics-enabled epidermal systems have potential to support a broad range of clinical applications in healthcare including analysis of biomarkers, drug administration, and real time diagnosis and monitoring of medical conditions including diabetes, inflammation and hydration state. See, e.g., US20060253011; US20100179403; WO 2016/025468; WO 2016/025438; WO2010030609; US20070027383; US20070179371A1; U.S. Pat. Nos. 4,960,467; 6,198,953; and WO2009025698A1.

As will be understood from the forgoing, the development of wearable systems is needed for integrating microfluidic functionality with tissue mounted sensing and actuation. Wearable systems are needed, for example, having physical formats and mechanical properties providing a robust interface with the skin to achieve quantitatively reliable collection and handling of biofluids over clinically relevant time intervals. In addition, microfluidic systems are needed that are capable of effective collection, pretreatment, storage and analysis of biofluids to support a range of applications for wearable systems including medical diagnostics and therapy.

Conventional approaches for real-time measurement of biomarkers in a biofluid, such as sweat, are limited. In certain cases, conventional systems include complex and bulky hardware, such as a potentiostat for signal generation, radio transmitters, and a battery. Such systems are difficult to miniaturize and inhibit portability. Furthermore, conventional systems may include potentiometric electrolytic sensors that require complicated (re)calibration protocols for each use, which may be prohibitive for end-user experiences, and these systems may further be plagued by signal drift between calibrations. Some conventional approaches lack the capacity to determine dynamic changes in biofluid or biomarkers properties and others fail to detect physiologically relevant species such as metabolites, proteins, and drugs.

Provided herein are wireless and battery-free microfluidic devices that address these, and other challenges, via, for example, dynamic optical sensing of a range of biomarkers.

SUMMARY OF THE INVENTION

The invention provides a versatile sensing platform for sensing and analysis of biofluids, particularly well-suited for sensing and analysis of sweat. Systems of the invention allows for sensitive and selective characterization of a range of analytes in sweat including metabolites, electrolytes and biomarkers. Systems of the invention provide a noninvasive and accurate means for quantitative characterization of important sweat characteristics including sweat volume, sweat loss and sweat rate. Systems of the invention are compatible with materials and device geometries for important class of conformal tissue mounted electronic devices, including epidermal electronic devices.

Provided herein are various microfluidic systems useful for a range of applications, including monitoring a biofluid such as sweat or a component thereof. As will be apparent the various classes of sensors provided herein may be used independently or in combination with each other.

In an aspect, a microfluidic system for monitoring a biofluid comprises: (1) substrate, such as a flexible substrate; (2) a microfluidic network at least partially embedded in or supported by the substrate; (3) a biofluid inlet fluidically connected to the microfluidic network to transport a biofluid from a skin surface to the microfluidic network; and (4) an optical sensor supported by the substrate and configured to sense one or more parameters of the biofluid or a component thereof, the optical sensor including one or more integrated optical structures for detection or visualization of the optical sensor.

In an aspect, a microfluidic system for monitoring a biofluid comprises: (1) substrate, such as a flexible substrate; (2) a microfluidic network at least partially embedded in or supported by the substrate; (3) a biofluid inlet fluidically connected to the microfluidic network to transport a biofluid from a skin surface to the microfluidic network; and (4) an electrochemical sensor supported by the substrate and configured to sense one or more parameters of the biofluid or a component thereof; the electrochemical sensor comprises a cathode and an anode, wherein both of the cathode and anode is provided in physical contact with the biofluid and functionalized to provide reactivity with one or more analytes in the biofluid.

In an aspect, a microfluidic system for monitoring a biofluid comprises: (1) substrate, such as a flexible substrate; (2) a microfluidic network at least partially embedded in or supported by the substrate; (3) a biofluid inlet fluidically connected to the microfluidic network to transport a biofluid from a skin surface to the microfluidic network; and (4) an electronic sensor supported by the substrate and configured to sense one or more parameters of the biofluid or a component thereof; wherein the parameters include the rate of production or loss of the biofluid from a subject.

In an aspect, a microfluidic system for monitoring a biofluid comprises: (1) a substrate, such as flexible substrate;

(2) a microfluidic network at least partially embedded in or supported by the substrate; (3) a biofluid inlet fluidically connected to the microfluidic network to transport a biofluid from a skin surface to the microfluidic network; (4) a colorimetric sensor supported by the substrate and configured to detect a first analyte of the biofluid or a component thereof; (5) an electrochemical sensor supported by the substrate and configured to detect a second analyte of the biofluid or a component thereof; and (6) a biofluid rate sensor supported by the substrate and configured to detect a rate of biofluid production or loss from a subject.

In an aspect, a microfluidic system for monitoring a biofluid comprises: (1) substrate, such as a flexible substrate; (2) a microfluidic network at least partially embedded in or supported by the substrate; (3) a biofluid inlet fluidically connected to the microfluidic network to transport a biofluid from a skin surface to the microfluidic network; and (4) a sensor supported by the substrate and configured to detect one or more parameters of the biofluid or a component thereof; (5) an electronic device configured to provide wireless power, wireless communication or both for the system; wherein the electronic device is selectively releasable from the substrate and microfluidic network.

The invention provides versatile optical sensors, particularly well-suited for epidermal applications for monitoring sweat of a subject, such as a human subject.

In an embodiment, for example, the one or more integrated optical structures are one or more lenses, lens arrays, filters, optical gratings, reflectors, optical sources, optical detectors, retroreflectors, pattern of surface roughness or any combination of these; wherein the integrated optical structures are integrated in a sensor channel or reservoir that is a part of the microfluidic network or a sensor channel or reservoir that is in fluid communication with the microfluidic network. In an embodiment, for example, the sensor is a colorimetric sensor, a fluorometric sensor, a scattered light sensor, an extinction-based sensor, a chemiluminescence sensor or any combination of these.

In an embodiment, for example, the sensor comprises one or more reactants provided in a sensor reservoir or channel of the microfluidic network or a sensor reservoir or channel in fluid communication with the microfluidic network; wherein interaction between the reactant and the biofluid results in a measureable change in an optical property of the biofluid or component thereof. In an embodiment, for example, the sensor comprises a channel or reservoir of the microfluidic network or comprises a channel or reservoir of the microfluidic network; wherein the channel or reservoir has an inlet for receiving the biofluid; wherein a reactant is provided proximate to the inlet that provides a change in an optical property upon contact with the biofluid; wherein the position of the biofluid in the channel or reservoir is characteristic of the local rate biofluid from the skin of a subject. In an embodiment, for example, the channel or reservoir has a volume selected from the range of 1-500 µL.

In an embodiment, for example, the one or more reactants are an indicator, a dye, a fluorophore, a chelating agent, or any combination of these. In an embodiment, for example, the one or more reagent is immobilized in a matrix in a sensor channel or reservoir or the walls of a sensor channel or reservoir. In an embodiment, for example, the matrix is a gel, a hydrogel, coating, particles, a filler or any combination of these. In an embodiment, for example, the reagent is selected from the group consisting of silver chloranilate, of $CoCl_2$, glucose oxidase, peroxidase, potassium iodide, lactate d dehydrogenase, diaphorase, formazan dyes, 2,4,6-tris (2-pyridiyl)-s-triazine (TPTZ) complexed with mercury ion or iron ion, a 2,2'-bicinchoninic acid, 1,10-phenanthroline, a universal pH indicator. In an embodiment, for example, the integrated optical components include one or more indicator layers to provide for visualization of the optical sensor; wherein the indicator layer comprises a scattering media with a refractive index within 20% of the biofluid.

In an embodiment, for example, the integrated optical components include one or more color reference markers. In an embodiment, for example, the integrated optical components include one or more colorimetric temperature sensors comprising a thermochromic liquid crystal layer. In an embodiment, for example, the sensor is a fluorometric sensor comprising a microfluidic reservoir and a detachable black light-shielding film provided in a multilayer geometry, wherein the microfluidic reservoir is in fluidic communication with the microfluidic network and wherein microfluidic reservoir contains one or more fluorophore reagent.

The invention provides versatile electrochemical sensors, particularly well-suited for epidermal applications for monitoring sweat of a subject, such as a human subject.

In an embodiment, for example, a current generated between the cathode and the anode is proportional to the amount or concentration of one or more analytes in the biofluid. In an embodiment, for example, the cathode and the anode are provided in a sensor reservoir or channel of the microfluidic network or a sensor reservoir or channel in fluid communication with the microfluidic network.

In an embodiment, for example, the cathode, the anode or both are independently configured to react selectively with the one or more analytes in the biofluid. In an embodiment, for example, the cathode, the anode or both are independently functionalized with one or more catalysts. In an embodiment, for example, the anode is configured to oxidize an analyte in the biofluid and the cathode is configured to reduce oxygen in the biofluid.

In an embodiment, for example, the cathode, anode or both is independently functionalized with one or more enzymes or derivatives thereof. In an embodiment, for example, the cathode, anode or both independently comprises a redox mediator for shuttling electrons to a contact pad or current collector. In an embodiment, for example, the redox mediator is a tetratiafulvalene, quionone redox dye or any combination thereof. In an embodiment, for example, the anode is functionalized with a lactate oxidase (LOx) enzyme, glucose oxidase, alcohol oxidase, other oxidases and dehydrogenases, or any combination thereof. In an embodiment, for example, the cathode comprises an oxygen reduction catalyst. In an embodiment, for example, the oxygen reduction catalyst is a noble metal catalyst or an enzyme. In an embodiment, for example, the oxygen reduction catalyst is platinum black, platinum on carbon, ruthenium on carbon or a combination of these. In an embodiment, for example, the oxygen reduction catalyst is laccase or bilirubin oxidase.

In an embodiment, for example, the cathode, anode or both independently further comprises a surface area enhancing component. In an embodiment, for example, nanostructured material or a microstructured material, such as a nanostructured or microstructured conductor or semiconductor. In an embodiment, for example, the surface area enhancing component comprises carbon nanotubes, carbon nanotubes, graphene, metal nanoparticles, metal oxide nanoparticles, fullerenes, graphene, carbon nanoparticles, graphite, carbon fibers or any combination thereof.

In an embodiment, for example, the cathode, anode or both independently further comprises a contact pad, a current collector or both. In an embodiment, for example, the cathode, anode or both independently further comprise a membrane. In an embodiment, for example, the membrane is a polymeric membrane or a ceramic membrane. In an embodiment, for example, the membrane is a chitosan and polyvinyl chloride membrane, polyurethane, silicone or a Nafion® membrane.

In an embodiment, for example, the electrochemical sensor is for measuring the concentration or amount of lactate or glucose. In an embodiment, for example, the electrochemical sensor is for measuring the concentration or amount of electrolyte. In an embodiment, for example, the electrochemical sensor further comprises a readout circuit for digitalization of an output signal. In an embodiment, for example, the electrochemical sensor is operably connected to an electronic device providing for wireless power harvesting. In an embodiment, for example, the electrochemical sensor is operably connected to an electronic device providing for wireless data transmission, for example, the electronic device is a NFC electronics module operably connect to support wireless power delivery, wireless data transmission or both to the system.

The invention provides versatile electronic sensors, particularly well-suited for epidermal applications for monitoring sweat of a subject, such as a human subject.

In an embodiment, for example, the electronic sensor comprises a sensor reservoir or channel of the microfluidic network or a sensor reservoir or channel in fluid communication with the microfluidic network; wherein a plurality of electrodes are provided in the sensor reservoir or channel. In an embodiment, for example, the electrodes are configured to measure impedance of biofluid provided to the chamber at a plurality of positions in the sensor channel or reservoir, thereby providing sensing or measurement of the production or loss of the biofluid from a subject.

In an embodiment, for example, the electrodes are provide on at least a portion of the bottom or the walls of the sensor channel or reservoir. In an embodiment, for example, the channel or reservoir is provided in a linear geometry, serpentine geometry or interdigitated geometry. In an embodiment, for example, the sensor channel or reservoir has a thickness selected from 1 µm to 10 mm, a width selected from 10 µm to 5 mm and a length selected from 100 µm to 50 cm. In an embodiment, for example, the electrodes comprises one or more conductive or semiconducting structures comprising a materials selected form the groups consisting of Cu, Au, Ti, Pt, carbon, Ag or any combinations thereof. In an embodiment, for example, the electrodes independently have a thickness selected from 5 nm to 1000 µm, a width selected from 1 µm to 1000 µm and a length selected from 100 nm to 20 cm. In an embodiment, for example, the electrodes are flexible electrodes.

In an embodiment, for example, the electrodes comprise a first electrode and a second electrode; wherein each of the first electrode and a second electrode extend at least a portion of the sensor reservoir or channel, and wherein the first electrode and a second flexible electrode are not in direct electrical communication with each other. In an embodiment, for example, the first electrode and second electrode are provided in a parallel configuration, concentric configuration, an interdigitated configuration, a nested configuration or any combination of these.

In an embodiment, for example, the sensor channel or reservoirs is configured to receive and accommodate the biofluid, wherein the biofluid fills the sensor reservoir or channel thereby providing for indirect electrical communication between the first and second electrodes. In an embodiment, for example, the system further comprise one or more additional reference electrodes provides in the sensor channel or reservoir or an additional sensor channel or reservoir in fluid communication with the microfluidic network for sensing the composition of the biofluid, for example, wherein the one or more additional reference electrodes are for measuring change in conductivity of the biofluid.

In an embodiment, for example, the electrochemical sensor further comprises a readout circuit for digitalization of an output signal. In an embodiment, for example, the electrochemical sensor is operably connected to an electronic device providing for wireless power harvesting. In an embodiment, for example, the electrochemical sensor is operably connected to an electronic device providing for wireless data transmission, for example, wherein the electronic device is a NFC electronics module operably connect to support wireless power delivery, wireless data transmission or both to the system.

The invention provides versatile electronic sensors that are configured for detachment and reuse of certain system components, such as electronic device components. In an embodiment, for example, the microfluidic network and substrate are coupled to the electronic device by one or more selectively releasable coupling elements. In an embodiment, for example, the microfluidic network and substrate are coupled to the electronic device by one or more self-aligning coupling elements. In an embodiment, for example, the microfluidic network and substrate are coupled to the electronic device by one or more magnetic coupling elements. In an embodiment, for example, the electronic device is configured for reusability.

Systems of the invention include wirelessly powered systems; battery-less systems, and systems configured for one-way or two-way wireless communication, such as wireless data transmission, for example via incorporation of a NFC device component.

In an embodiment, for example, a system further comprises a NFC electronics module operably connect to support wireless power delivery, wireless data transmission or both to the system. In an embodiment, for example, the NFC electronics module is a multilayer, flexible circuit. In an embodiment, for example, the NFC electronics module includes an antenna providing for RF power of the system. In an embodiment, for example, the NFC electronics module provides for one-way or two-way wireless communication to an external receiving or transmitting electronic device. In an embodiment, for example, the receiving or transmitting electronic device is a portable electronic device. In an embodiment, for example, the NFC electronics module is at least partially encapsulated in a barrier layer, such as a moisture barrier.

The present systems are capable of sensing and quantitative characterization of a range of sweat parameters and components of sweat, including biomarker analytes in sweat.

In an embodiment, for example, the one or more parameters of the biofluid are visually observable. In an embodiment, for example, a signal corresponding to the one or more parameters of the biofluid is transmitted from the system to an external receiving device. In an embodiment, for example, the one or more parameters is sweat volume, sweat rate, sweat loss or any combination of these.

In an embodiment, for example, the one or more parameters is pH. In an embodiment, for example, the one or more parameters of the biofluid or a component thereof comprise the presence of, amount or concentration of an analyte in the biofluid or component thereof. In an embodiment, for example, the analyte is an electrolyte, a metabolite, or a biomarker in the biofluid or component thereof. In an embodiment, for example, a leading edge of the volume of biofluid in a sensor microfluidic channel or reservoir is sensed as a function of time. In an embodiment, for example, the lead edge of the volume of the biofluid in the microfluidic channel is sensed visually or measured using a photodetector.

The systems-level design, materials and properties of the present systems are important to support a range of applications including epidermal sensing and characterization of sweat.

In an embodiment, for example, the system provided herein comprises an epidermal electronic system. In an embodiment, for example, the system provided herein comprises a wearable electronic system. In an embodiment, for example, the substrate, microfluidic network or both is capable of establishing conformal contact with the skin of a human subject. In an embodiment, for example, the substrate, microfluidic network or both is characterized by an average Young's Modulus equal to or less than 10 MPa. In an embodiment, for example, the substrate, microfluidic network or both is characterized by an average Young's Modulus selected from the range of 0.5 kPa to 10 MPa. In an embodiment, for example, the substrate, microfluidic network or both is characterized by a net bending stiffness less than or equal to 1 nN m. In an embodiment, for example, the substrate, microfluidic network or both is characterized by a selected from a range of 0.1 to 1 nN m. In an embodiment, for example, the system has a footprint selected from a range of 100 mm$^2$ to 1000 cm$^2$. In an embodiment, for example, the sensor comprises a sensor channel or reservoir that is at least partially optically transparent in the visible or infrared region of the electromagnetic spectrum. In an embodiment, for example, the sensor comprises a sensor channel or reservoir characterized by a volume selected over the range of 1 $\mu m^3$-10000 mm$^3$. In an embodiment, for example, the sensor comprises a sensor channel or reservoir characterized by a volume selected over the range of 1000 $\mu m^3$-10000 mm$^3$.

In an aspect, a method of analyzing biofluid from a subject comprises the steps of: (1) providing a microfluidic system for monitoring the biofluid, the system comprising: (i) substrate, such as a flexible substrate; (ii) a microfluidic network at least partially embedded in or supported by the substrate; (iii) a biofluid inlet fluidically connected to the microfluidic network to transport the biofluid from a skin surface to the microfluidic network; and (iv) an optical sensor supported by the substrate and configured to sense one or more parameters of the sweat or a component thereof, the optical sensor including one or more integrated optical structures for detection or visualization of the optical sensor; (2) contacting the substrate of the system with a surface of the skin of a subject; and (3) analyzing the biofluid from the surface of the skin of the subject.

In an aspect, a method of analyzing biofluid from a subject comprises the steps of: (1) providing a microfluidic system for monitoring the biofluid, the system comprising: (i) substrate, such as a flexible substrate; (ii) a microfluidic network at least partially embedded in or supported by the substrate; (iii) a biofluid inlet fluidically connected to the microfluidic network to transport a biofluid from a skin surface to the microfluidic network; and (iv) an electrochemical sensor supported by the substrate and configured to sense one or more parameters of the biofluid or a component thereof; the electrochemical sensor comprising a cathode and an anode, wherein at least one of the cathode and an anode is provided in physical contact with the biofluid and functionalized to provide reactivity with one or more analytes in the biofluid; (2) contacting the substrate of the system with a surface of the skin of a subject; and (3) analyzing the biofluid from the surface of the skin of the subject.

In an aspect, a method of analyzing biofluid from a subject comprises the steps of: providing a microfluidic system for monitoring a biofluid, the system comprising: (i) substrate, such as a flexible substrate; (ii) a microfluidic network at least partially embedded in or supported by the substrate; (iii) a biofluid inlet fluidically connected to the microfluidic network to transport a biofluid from a skin surface to the microfluidic network; and (iii) an electronic sensor supported by the substrate and configured to sense one or more parameters of the biofluid or a component thereof; wherein the parameters include the rate of production or loss of the biofluid from a subject; (2) contacting the substrate of the system with a surface of the skin of a subject; and (3) analyzing the biofluid from the surface of the skin of the subject.

In an aspect, a method of analyzing biofluid from a subject comprises the steps of: (1) providing a microfluidic system for monitoring the biofluid, the system comprising: (i) substrate, such as a flexible substrate; (ii) a microfluidic network at least partially embedded in or supported by the substrate; (iii) a biofluid inlet fluidically connected to the microfluidic network to transport a biofluid from a skin surface to the microfluidic network; (iv) a colorometric sensor supported by the substrate and configured to detect a first analyte of the biofluid or a component thereof; (v) an electrochemical sensor supported by the substrate and configured to detect a second analyte of the biofluid or a component thereof; and (vi) a biofluid rate sensor supported by the substrate and configured to detect a rate of biofluid production or loss from a subject; (2) contacting the substrate of the system with a surface of the skin of a subject; and (3) analyzing the biofluid from the surface of the skin of the subject.

In an aspect, a method of analyzing biofluid from a subject comprises the steps of: (1) providing a microfluidic system for monitoring the biofluid, the system comprising: (i) substrate, such as a flexible substrate; (ii) a microfluidic network at least partially embedded in or supported by the substrate; (iii) a biofluid inlet fluidically connected to the microfluidic network to transport a biofluid from a skin surface to the microfluidic network; and (iv) an sensor supported by the substrate and configured to detect one or more parameters of the biofluid or a component thereof; (v) an electronic device configured to provide wireless power, wireless communication or both for the system; wherein the electronic device is selectively releasable from the substrate and microfluidic network; (2) contacting the substrate of the system with a surface of the skin of a subject; (3) analyzing the biofluid from the surface of the skin of the subject, and optionally (4) releasing the electronic device from the substrate and microfluidic network.

In a method provide herein, for example, the biofluid is sweat. In a method provide herein, for example, the subject is a human subject. In a method provide, for example, the subject is a human subject undergoing a diagnostic procedure. In a method provide herein, for example, the subject is a human subject undergoing a therapeutic procedure. In a method provide herein, for example, the subject is a human subject monitoring the presence, onset or progression of a disease condition. In a method provide herein, for example, the subject is a human subject undergoing a fitness activity For example, provided is a microfluidic system for monitoring a biofluid comprising: a flexible substrate; a microfluidic network at least partially embedded in or supported by the substrate; an electrochemical sensor supported by the substrate and fluidically connected to the microfluidic network; a biofluid inlet fluidically connected to the microfluidic network to transport a biofluid from a skin surface, during use, to the electrochemical sensor; and an electronic device in electronic contact with the electrochemical sensor to detect an electronic output from the electrochemical sensor.

A microfluidic system for monitoring a biofluid may comprise: a flexible substrate; a microfluidic channel at least partially embedded in or supported by the substrate; a biofluid inlet configured to introduce biofluid from the skin surface to the microfluidic channel during use; an outlet fluidically connected to the microfluidic channel and configured to reduce backpressure in the microfluidic channel; at least two biofluid tracking electrodes positioned along the microfluidic channel and spatially separated from each other by a microfluidic channel lumen; and an electronic device in electronic contact with the at least two biofluid tracking electrodes to measure a biofluid property of a biofluid introduced to the microfluidic channel.

Also provided are methods of monitoring a biofluid property using any of the devices or systems provided herein, including by the steps of: mounting a microfluidic system to a skin surface, wherein the microfluidic system has an electrochemical sensor comprising a biofluid working electrode and a counter-electrode to measure a biofluid property of a biofluid released from the skin surface; introducing a biofluid released from the skin surface to the electrochemical sensor; applying an electrical load to the biofluid working electrode; and detecting an electrical parameter with the biofluid counter-electrode, thereby monitoring the biofluid property.

Also provided herein are systems and methods for the volumetric detection of a biofluid utilizing flexible epidermal sensor systems and methods of fabricating the same. The provided systems utilize patterned or segment indicator tape or easily and quickly provide a wearer information regarding the amount of biofluid captured by the sensors. The methods of fabrication described herein are facile, inexpensive and do not require advanced manufacturing techniques such as photolithography.

In an aspect, provided is an epidermal microfluidic system for measuring a characteristic of a biofluid from a skin surface comprising: a) a flexible substrate; b) a biofluid inlet embedded on or supported by the substrate for receiving the biofluid from the skin surface; and c) a microfluidic channel embedded in or supported by the flexible substrate and fluidically connected to the inlet to receive the biofluid; the microfluidic channel having an indicator comprising a series of indicator tape segments configured such that the biofluid is transported along the series by wicking, wherein each of the indicator tap segments in the series is independently separated from at least one adjacent tape segment by a gap such that additional sweat volume is required to transport the biofluid through the gaps in the series.

In embodiments, for example, the system is for measurement of sweat volume loss or sweat volume loss rate. In an embodiment, the system further comprises a fluid outlet fluidically connected to the microfluidic channel.

In an aspect, provided is a method for determining sweat loss comprising: a) providing an epidermal microfluidic system in contact with a skin surface of a subject, the system comprising: i) a flexible substrate; ii) a biofluid inlet embedded on or supported by the substrate for receiving the biofluid from the skin surface; and iii) a microfluidic channel embedded in or supported by the flexible substrate and fluidically connected to the inlet to receive the biofluid; the microfluidic channel having an indicator comprising a series of indicator tape segments configured such that the biofluid is transported along the series by wicking, wherein each of the indicator tap segments in the series is independently separated from at least one adjacent tape segment by a gap such that additional sweat volume is required to transport the biofluid through the gaps in the series; and determining the subject's sweat loss by measuring the number of indicator tape segments which have contacted sweat.

In an aspect, provided is a method for fabricating a real-time sweat loss monitoring system comprising the steps of: a) providing an indicator having an indicator paper and a backing; b) patterning the indicator into a plurality of indicator paper segments; c) removing the indicator paper segments using a transfer stamp; d) placing the indicator paper segments onto a first flexible substrate; e) removing the transfer stamp; f) placing a second flexible substrate on the first flexible substrate, wherein the first and second substrates are formed to generate a channel containing the indicator paper segments; g) heating, providing pressure, or heating and providing pressure to create a fluidic seal between the first and second flexible substrate thereby generating a microfluidic channel; h) generating a biofluid inlet in fluidic communication with the microfluidic channel, thereby producing a real-time sweat loss monitoring system.

In an aspect, provided is a microfluidic system for monitoring a biofluid, the microfluidic system comprising: a flexible substrate, the substrate having a skin-facing surface and a back surface; a microfluidic network at least partially embedded in or supported by the substrate; a biofluid inlet fluidically connected to the microfluidic network to transport a biofluid from a skin surface to the microfluidic network; a capacitive sensor operably connected to the microfluidic network and configured to capacitively sense one or more parameters of the biofluid or a component thereof; the capacitive sensor comprising a first electrode and a second electrode; wherein at least one of the first electrode and the second electrode is not in physical contact with the biofluid; and a first dielectric element positioned between the microfluidic network and at least one of the first electrode and the second electrode. In some embodiments of this aspect, the first dielectric element is positioned between the microfluidic network and the capacitive sensor. In some embodiments of this aspect, the first dielectric element is supported by the substrate on the back surface of the substrate; and wherein the system further comprises a second dielectric element supported by the substrate and positioned on the skin-facing surface of the substrate. In some embodiments of this aspect, the second electrode is provided in physical contact with said biofluid; wherein said first electrode is not in physical contact with the biofluid; and wherein the first dielectric element positioned (i) between the first electrode and the second electrode, and (ii) between the first electrode and the microfluidic network. In some embodiments of this aspect: each of said first electrode and said second electrode is not in physical contact with said biofluid; the first dielectric element is supported by said substrate on said back surface, the first dielectric element being positioned between the first electrode and the microfluidic channel; a second dielectric element supported by the substrate on the skin-facing surface, the second dielectric element being positioned between the second electrode and the microfluidic channel; and the second dielectric element and the second electrode each independently comprises a biofluid inlet fluidically connected to the microfluidic network to transport a biofluid from a skin surface to said microfluidic network. In some embodiments of this aspect, the first and second electrodes are interdigitated. In some embodiments of this aspect, the first dielectric element is in physical contact with the biofluid. In some embodiments of this aspect, the second dielectric element is in physical contact with the biofluid. In some embodiments of this aspect, the capacitive sensor is configured to capacitively sense one or more parameters of the biofluid or a component thereof via frequency sweeping. In some embodiments of this aspect, the system further comprises an electronic device for providing wireless power delivery, wireless data transmission, or both to said system; the electronic device being operably connected to the capacitive sensor. In some embodiments of this aspect, the electronic device is a NFC electronics module or a Bluetooth electronics module. In some embodiments of this aspect, the dielectric element is a dielectric layer.

In an aspect, provided are methods of analyzing biofluid from a subject, the methods comprising steps of: providing a microfluidic system according to any of the embodiments disclosed herein, including but not limited to a microfluidic system comprising a capacitive sensor; contacting the substrate of the system with a surface of the skin of a subject; and analyzing the biofluid from the surface of the skin of the subject. In some embodiments of this aspect, the subject is a human subject. In some embodiments of this aspect, the biofluid is sweat.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

at 25° C. and (Panel D) the corresponding calibration (n=3). (Panel E) Plot illustrating reversible sensor response for lactate sensor for four consecutive cycles of varying lactate concentration. (Inset: Calibration plot comparing the sensor signal plotted in (Panel E) for the four cycles. V: voltage in millivolts; C: concentration in millimolar). (Panel F) Real-time data acquired for increasing lactate concentration in artificial sweat under common physiological sweat conditions (temperature=30° C.; pH=5.5). (Panel G) Calibration plot obtained for lactate sensors in artificial sweat at different pH (n=3).

Figure 12:
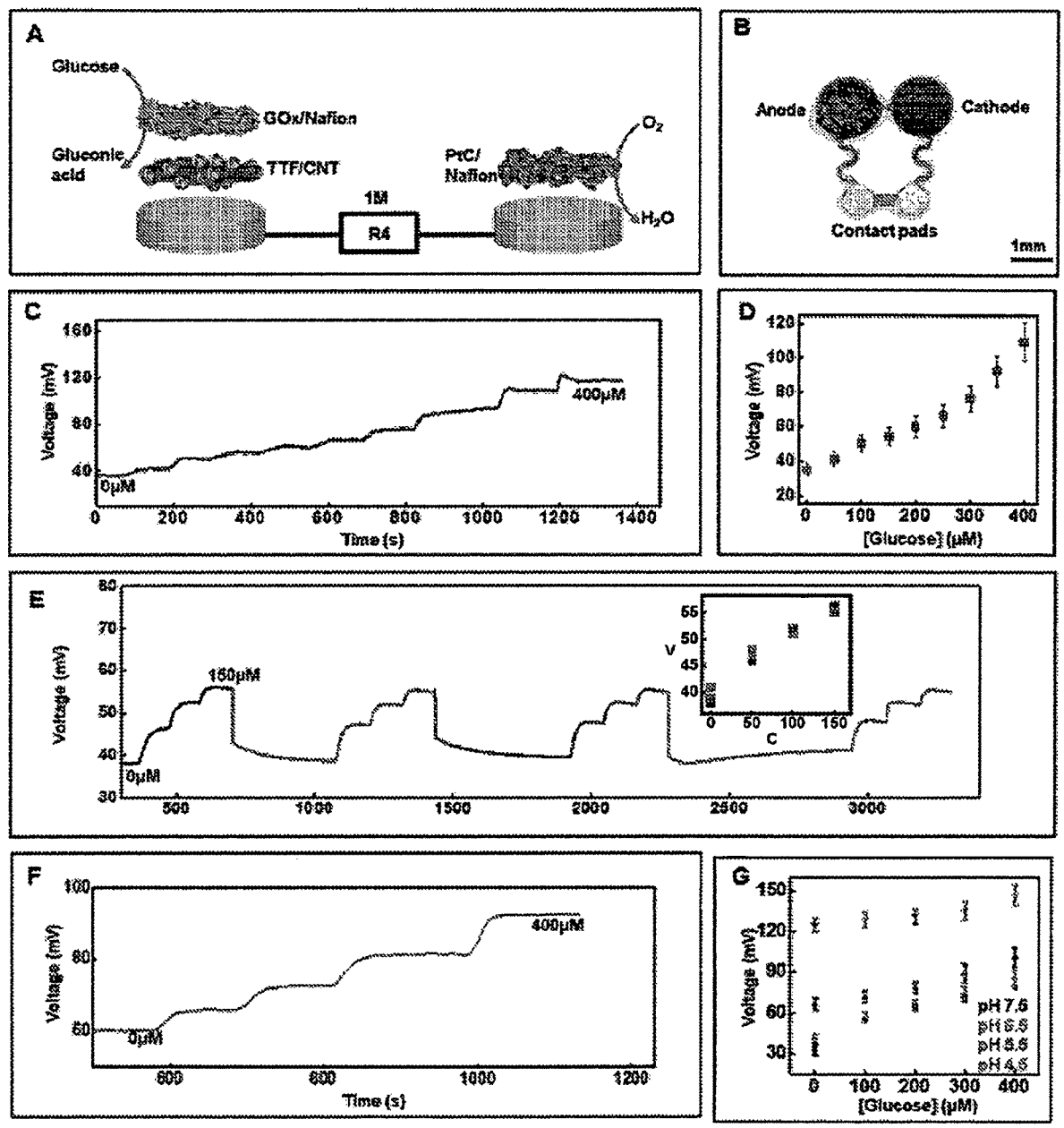

FIG. 12 Glucose sensor characterization. (Panel A) Exploded-view schematic visualizing layer makeup of the fuel cell-based glucose sensor. (Panel B) Image of the actual glucose sensor. (Panel C) Real-time sensor response to increasing glucose concentration in phosphate buffer (pH 7.0) at 25° C. and (Panel D) the corresponding calibration. (n=3) (Panel E) Plot illustrating reversible sensor response for glucose sensor for four consecutive cycles of varying glucose concentration. (Inset: Calibration plot comparing the sensor signal plotted in (Panel E) for the four cycles. V: voltage in millivolts; C: concentration in micromolar). (Panel F) Real-time data acquired for increasing glucose concentration in artificial sweat under common physiological sweat conditions (temperature=30° C.; pH=5.5). (Panel G) Calibration plot obtained for glucose sensors in artificial sweat at different pH (n=3).

Figure 13:
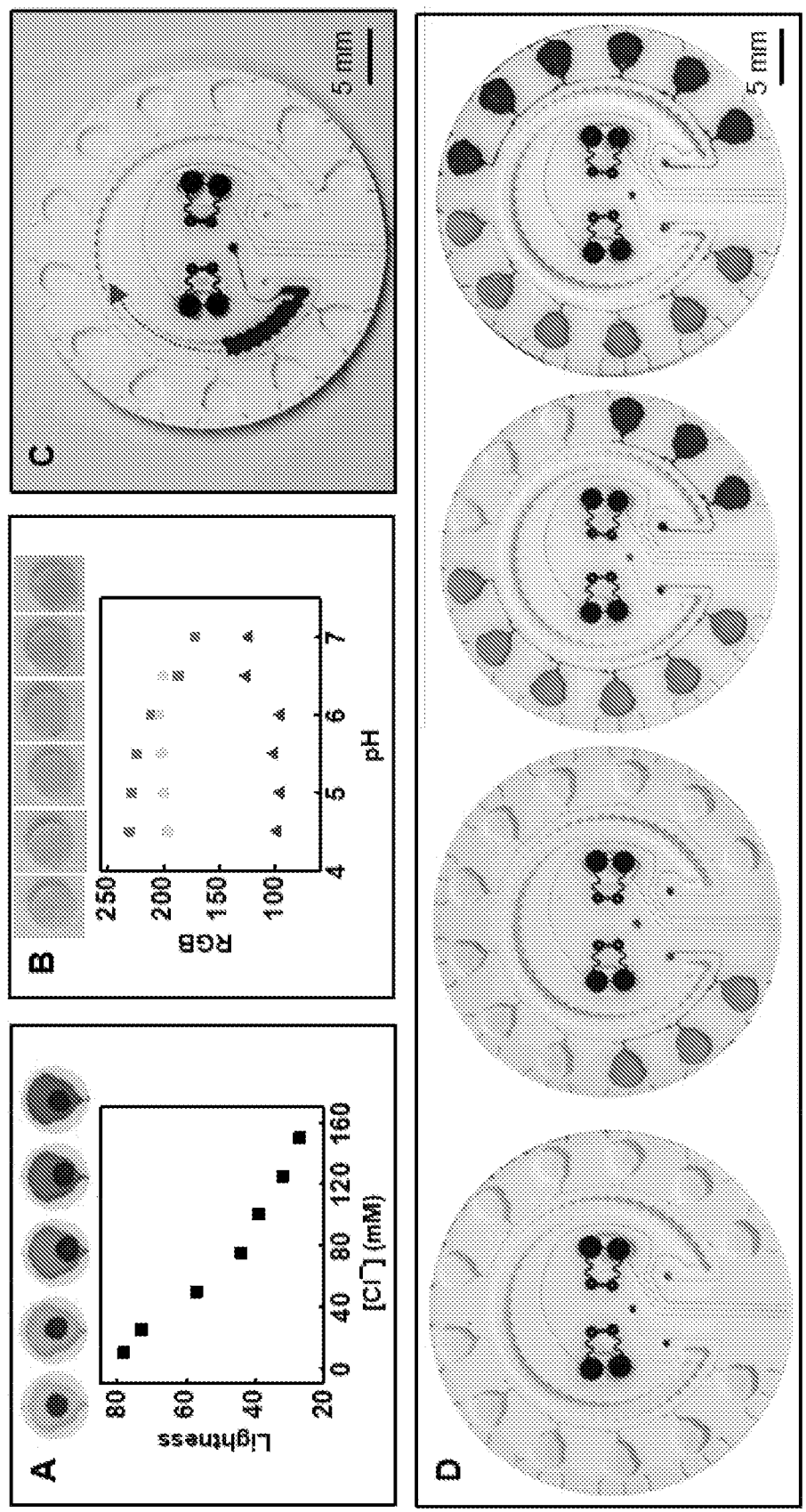

FIG. 13. Colorimetric assay characterization. Calibration and corresponding color evolution for physiologically relevant levels of (Panel A) chloride (n=3) and (Panel B) pH (n=3). (Panel C) Filling of sweat rate sensor. (Panel D) Image illustrating chrono-sampling feature of the microfluidics system.

Figure 14:
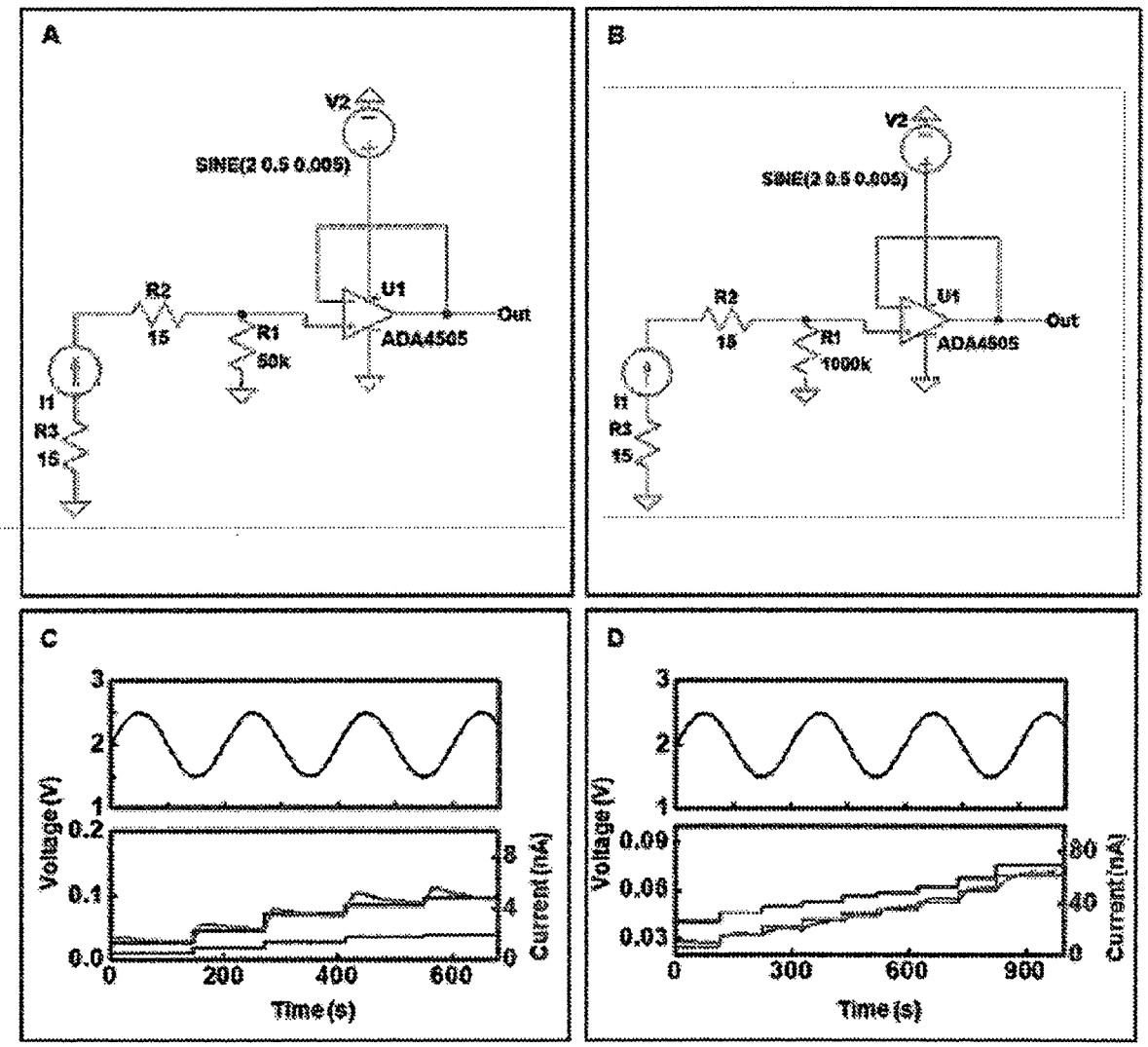

FIG. 14. (Panel A and Panel B) SPICE schematic of amplification scheme where R3 and R2 represent contact resistance of magnetic connection and R1 represents the respective load for (Panel A) lactate and (Panel B) glucose biofuel cell-based sensor. (Panels C-D) Simulation results for amplified signal (black trace for voltage and blue trace for sensor current) vs. benchtop measurements (red trace) with oscillating supply voltage; demonstrating supply voltage insensitivity for (Panel C) lactate and (Panel D) glucose measurements with increasing concentrations.

Figure 15:
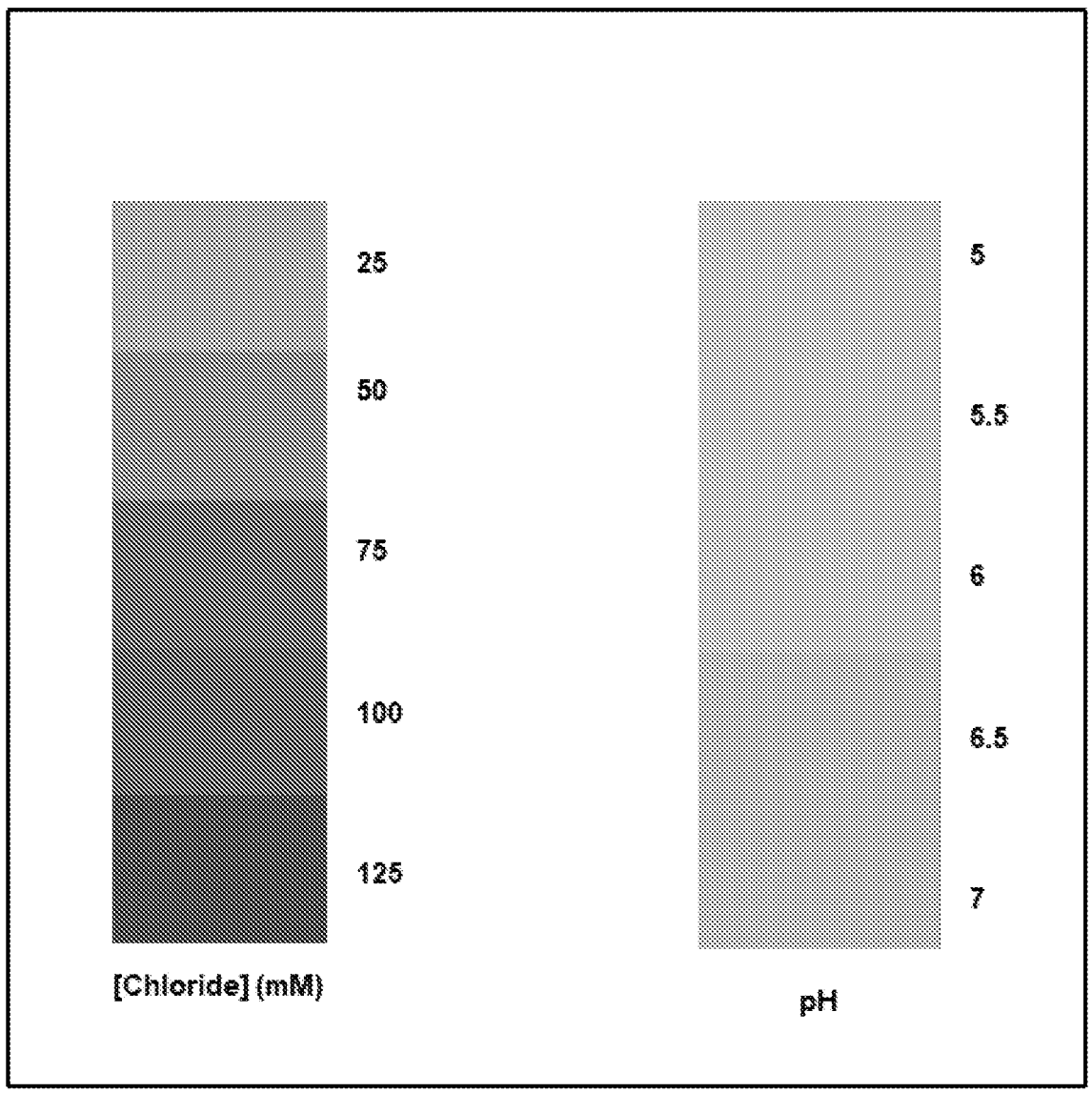

FIG. 15. Color reference marker of chloride and pH.

Figure 16:
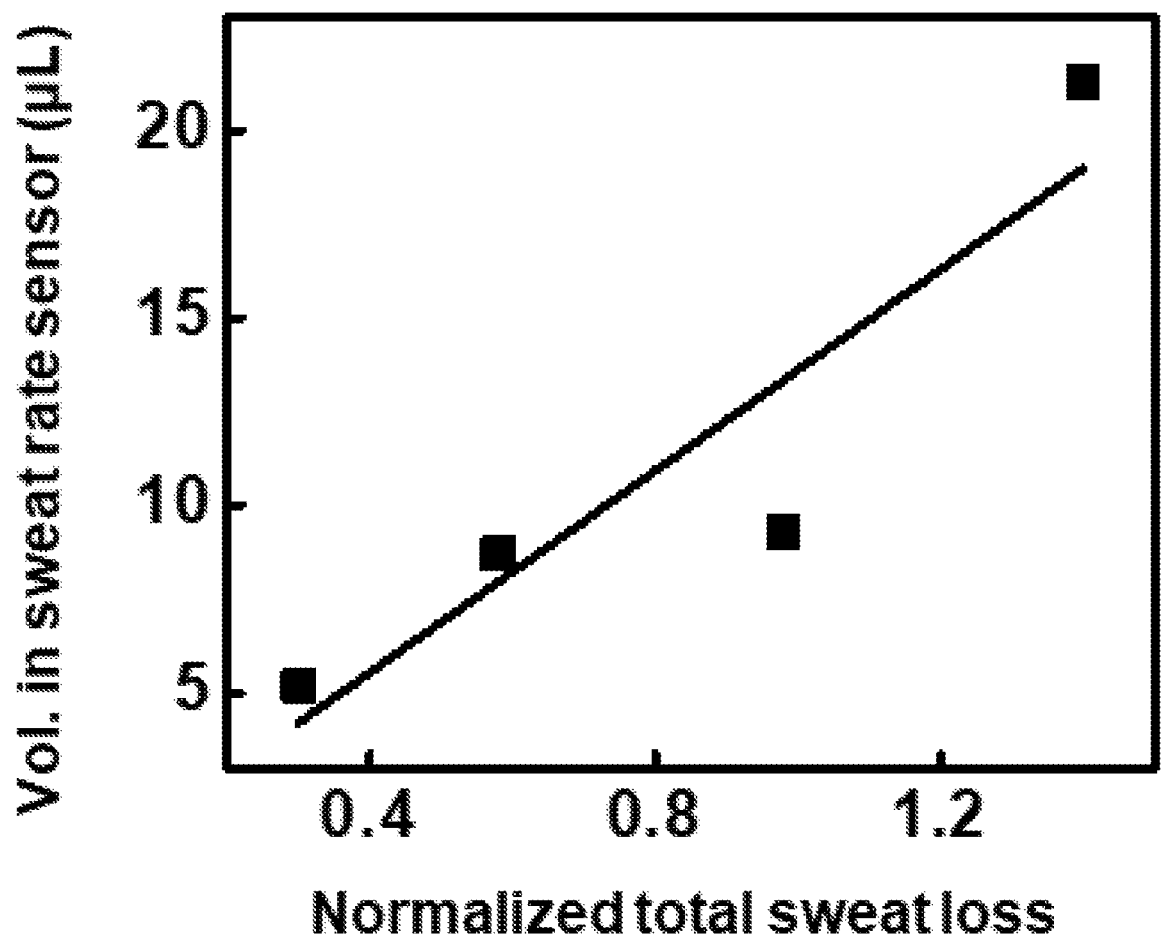

FIG. 16. Plot corresponding to the relationship between normalized total sweat loss and volume captured in sweat rate sensor.

Figure 17:
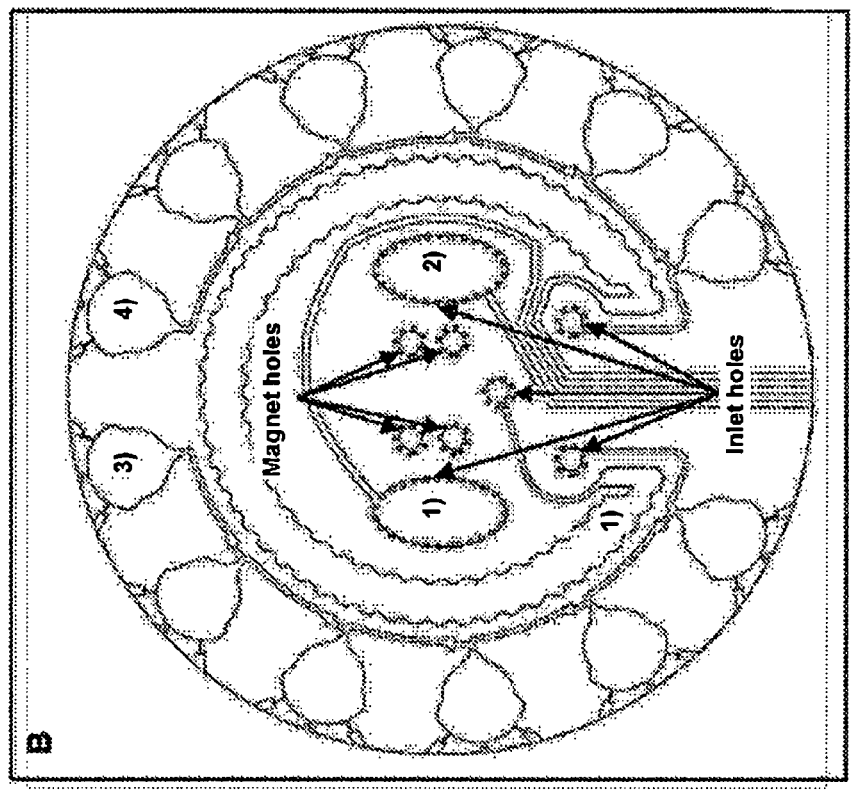
Figure 17:
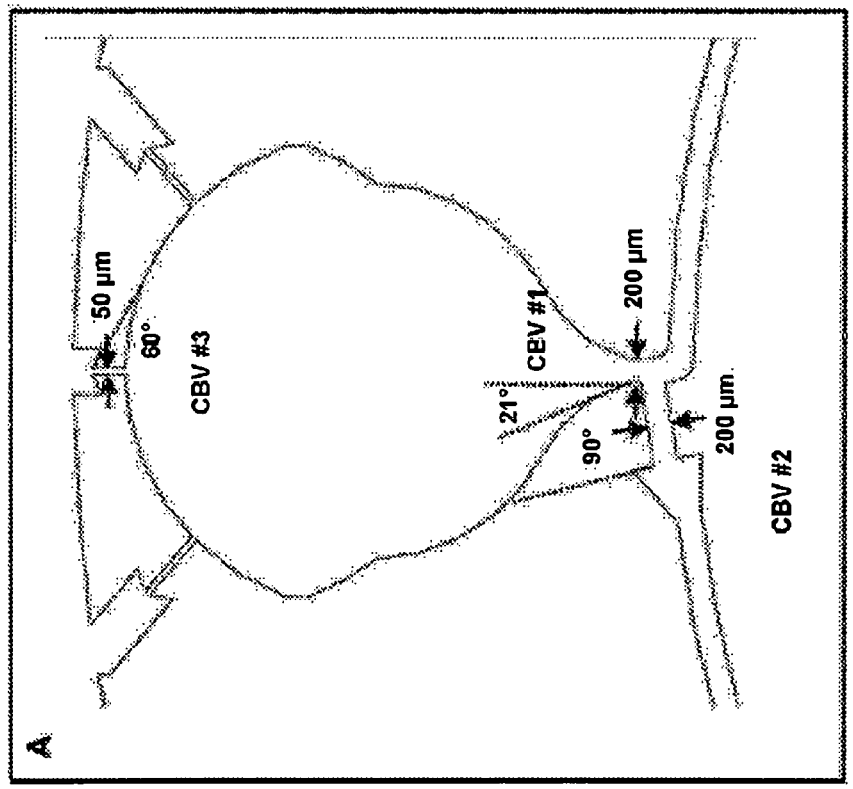

FIG. 17. (Panel A) Schematic illustration of capillary bursting valves in a colorimetric detection chamber. (Panel B) Schematic illustration of microfluidic channel: 1) Glucose detection chamber 2) lactate detection chamber 3) chloride chrono detection chambers 4) pH chrono detection chambers 5) sweat rate detection chamber.

Figure 18:
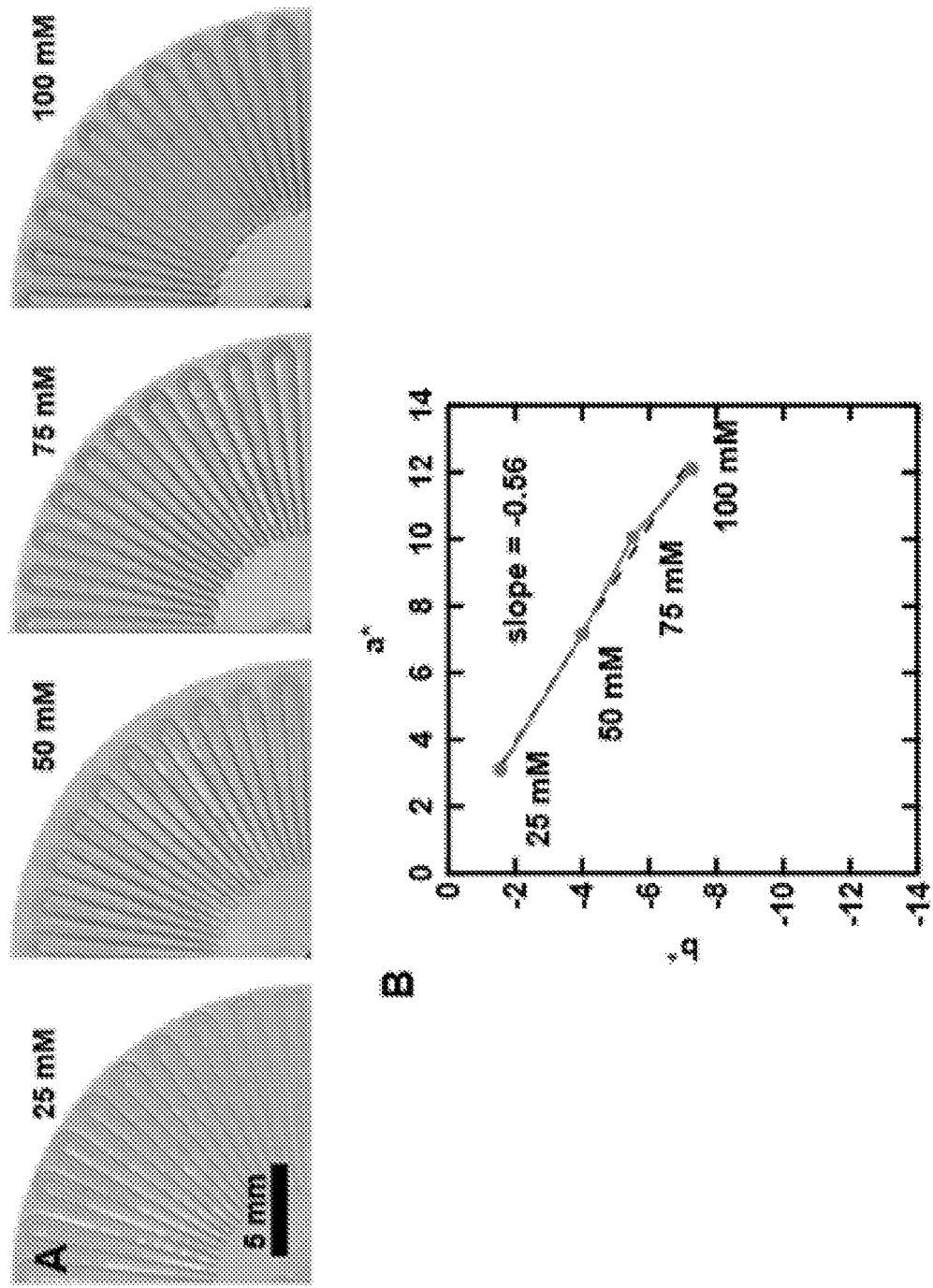

FIG. 18. Color calibration for chloride sensing. Panel A is a series of photographs of SIS devices with silver chloranilate reagent reacting with reference chloride concentrations. Panel B is a plot of a* and b* color values of reference chloride concentrations after reacting with silver chloranilate.

Figure 19:
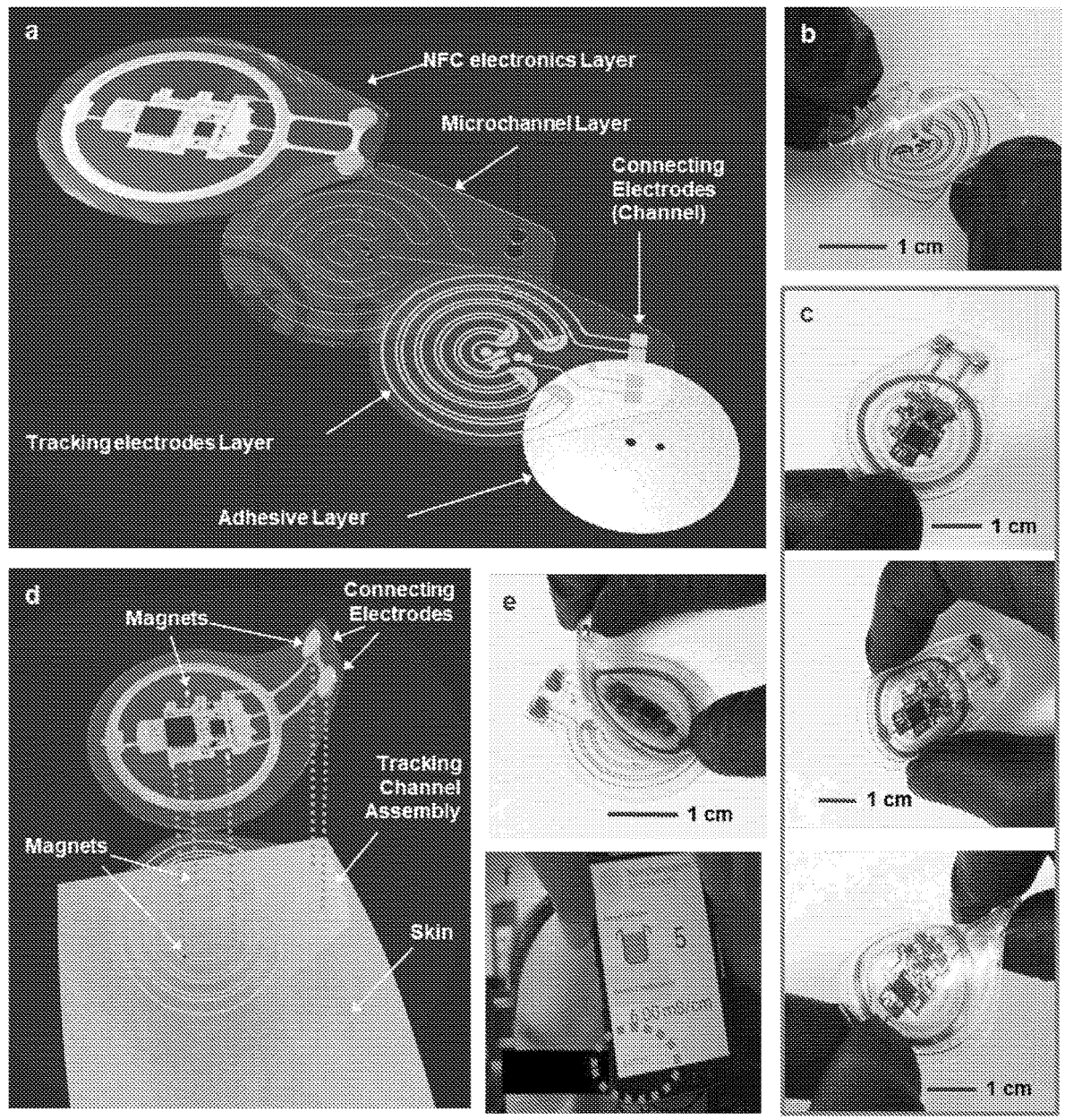

FIG. 19. Schematics of the battery free sweat rate readout device. Panel a: The exploded structure of the device. Panel b. The flexibility of sweat tracking electrodes. Panel c: The optical image of the assembled device and its examination of bend and twist. Panel d: The reusability of NFC electronics with magnets application, e: The optical image of electronics reuse examination. Panel f: Communication with smartphone by programmed application.

Figure 20:
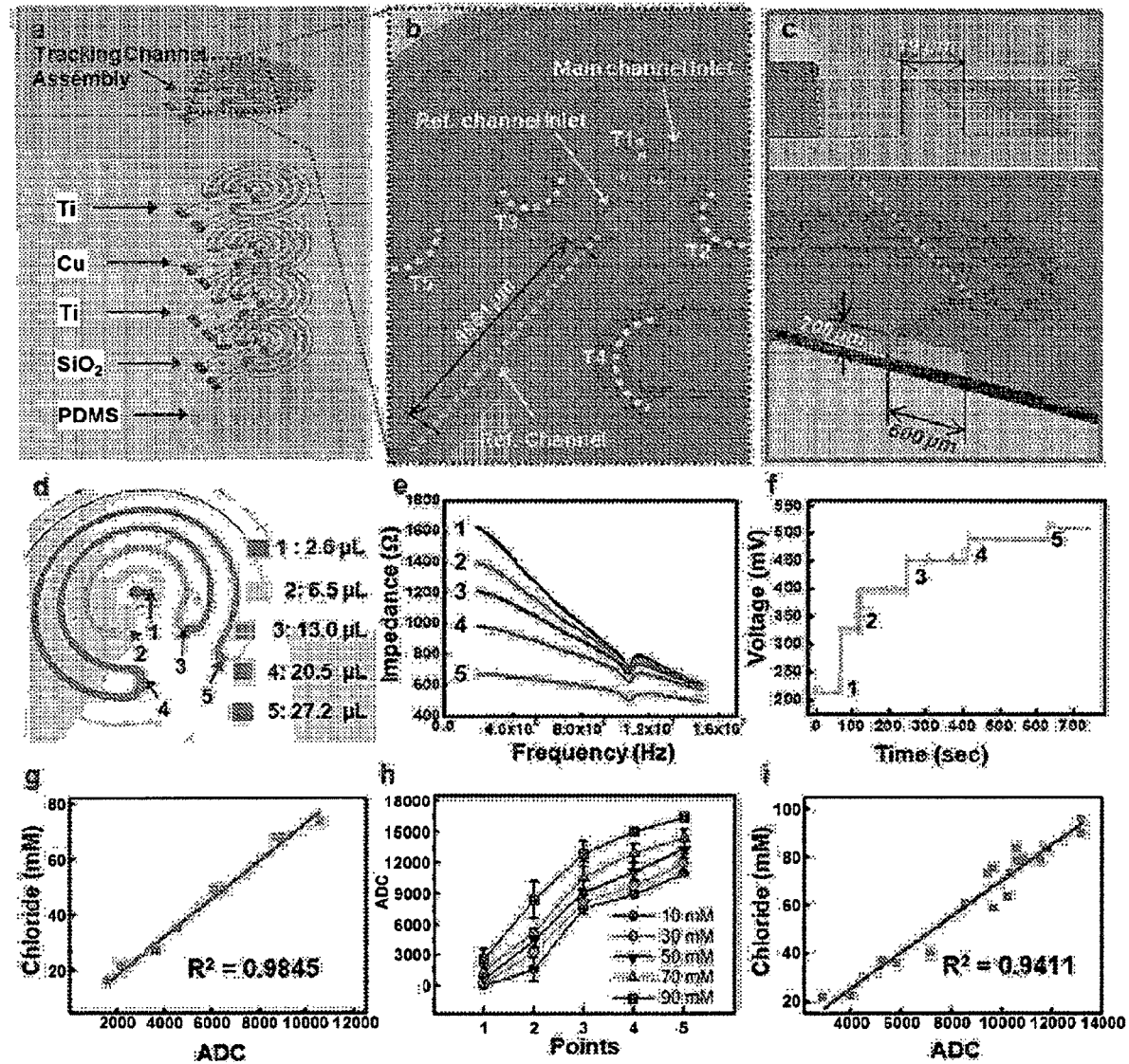

FIG. 20. The properties of electrodes, and calibration. Panel a: The exploded structure of flexible electrodes. Panel b: The expansion of tracking soft microfluidics and its organization. Panel c: The dimensions of microfluidic channel and tracking electrodes. Panel d: The volumes for each time points. Panel e: Electrodes properties on the impedance measurement by sweeping frequency at $200$-$1.5 \times 10^7$ Hz. Panel f: Continuous tracking of sweat using assembled sweat readout channel. Panel g: The calibration of reference channel with sodium chloride standard solution. Panel h: The calibration of main tracking channel with sodium chloride standard solution. Panel i: The comparison plotting with human test results using NFC system and instrument chloride analysis.

Figure 21:
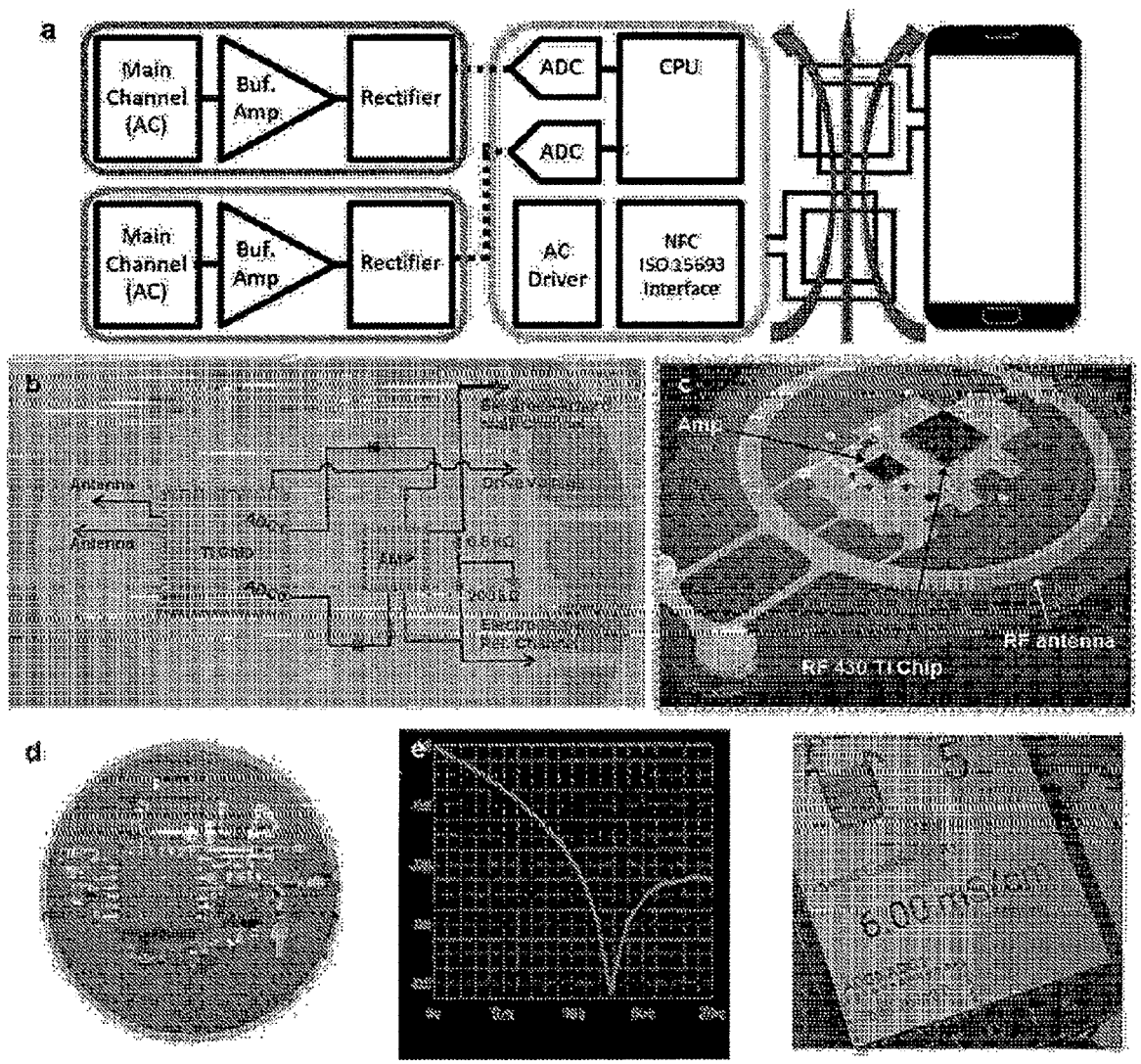

FIG. 21. Scheme of NFC system and fabrication. Panel a: The schematic diagram of NFC system organization. Panel b: The design of circuit board for the NFC system. Panel c: The illustration of NFC system packaged. Panel d: The optical image of fabricated NFC system. Panel e: RF antenna design for RF resonance. Panel f: ADC values shown on the smartphone screen, the data from the NFC system in human test.

Figure 22:
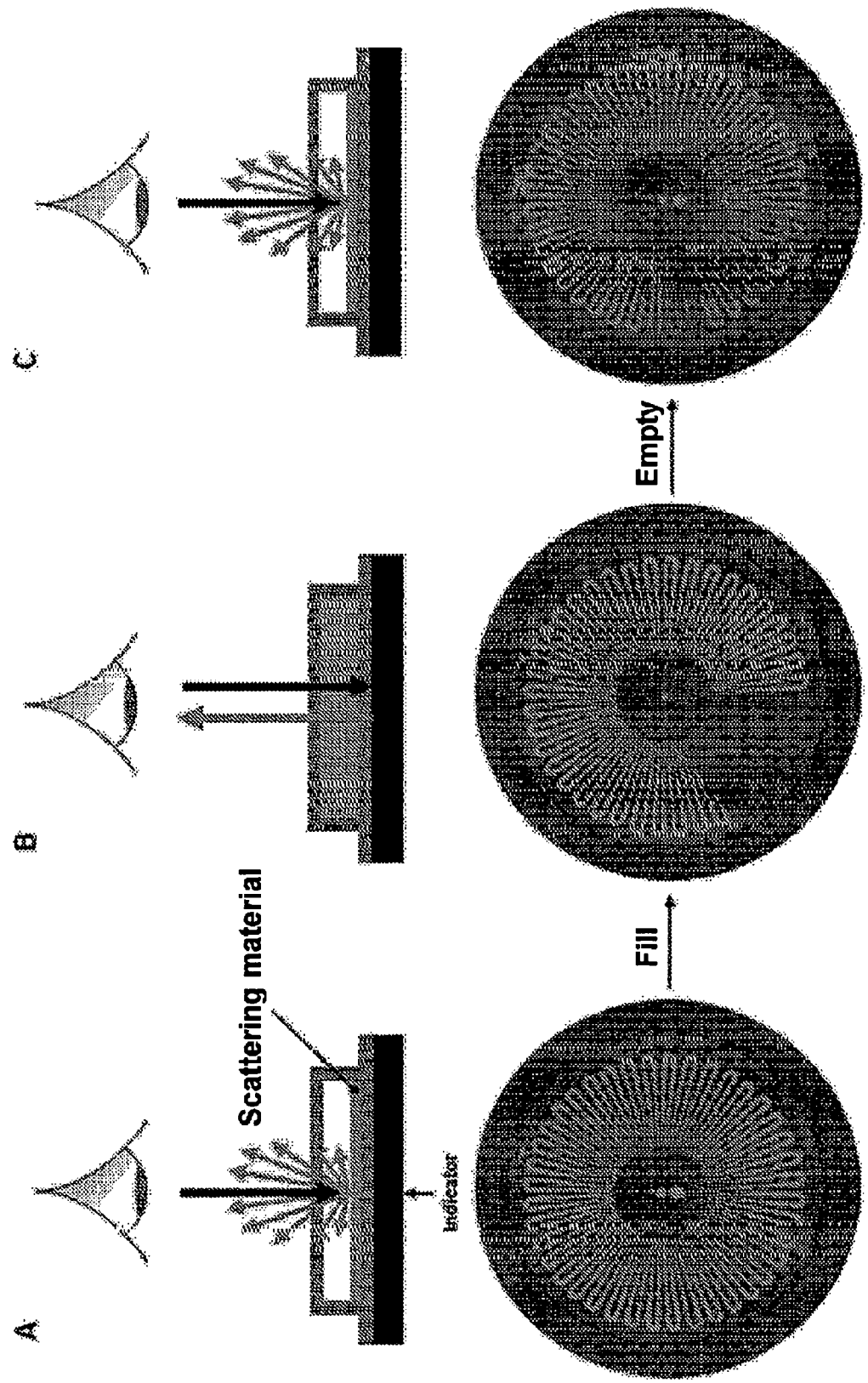

FIG. 22. Resettable sweat indicator via light scattering. Panel A is a schematic (top) and image (bottom) showing that scattering material patterned in the channel of a microfluidic device causes light scattering and presents of a white color. Panel B is a schematic (top) and image (bottom) showing that captured sweat enters the microchannel and reduces scattering and presents the color of the indicator (black). Panel C is a schematic (top) and image (bottom) showing that extracting sweat resets the device to the initial state.

Figure 23:
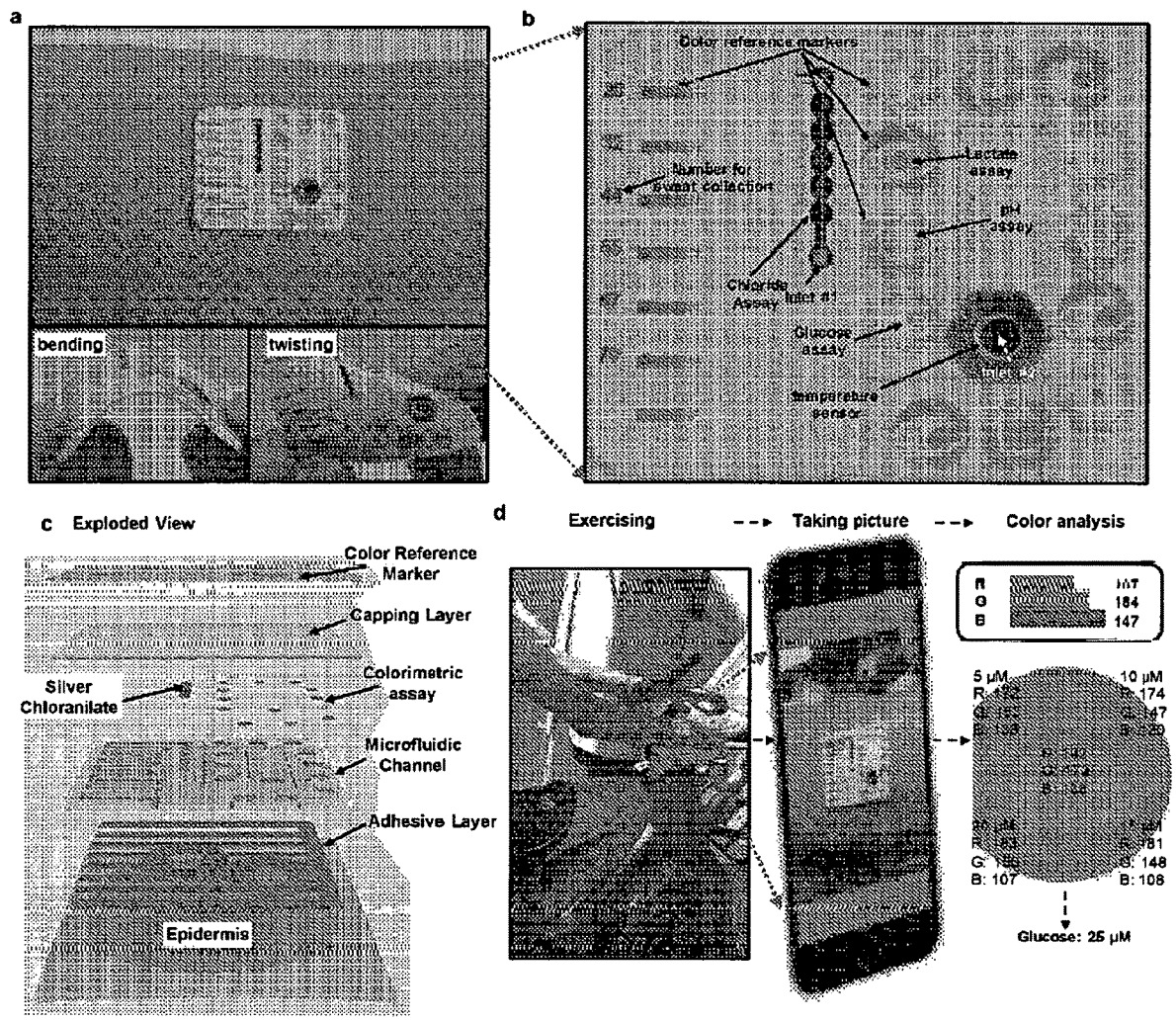

FIG. 23. Panel a: Optical images of soft and flexible microfluidic devices for colorimetric analysis of sweat on the skin (top) and under mechanical diction of bending (bottom left) and twisting (bottom right). Panel b: Top view illustration of microfluidic channels filled with blue-dyed water. Panel c: Exploded view illustration of a device and its interface with skin. Panel d: Procedure of collecting sweat sample and color analysis of digital image of the device.

Figure 24:
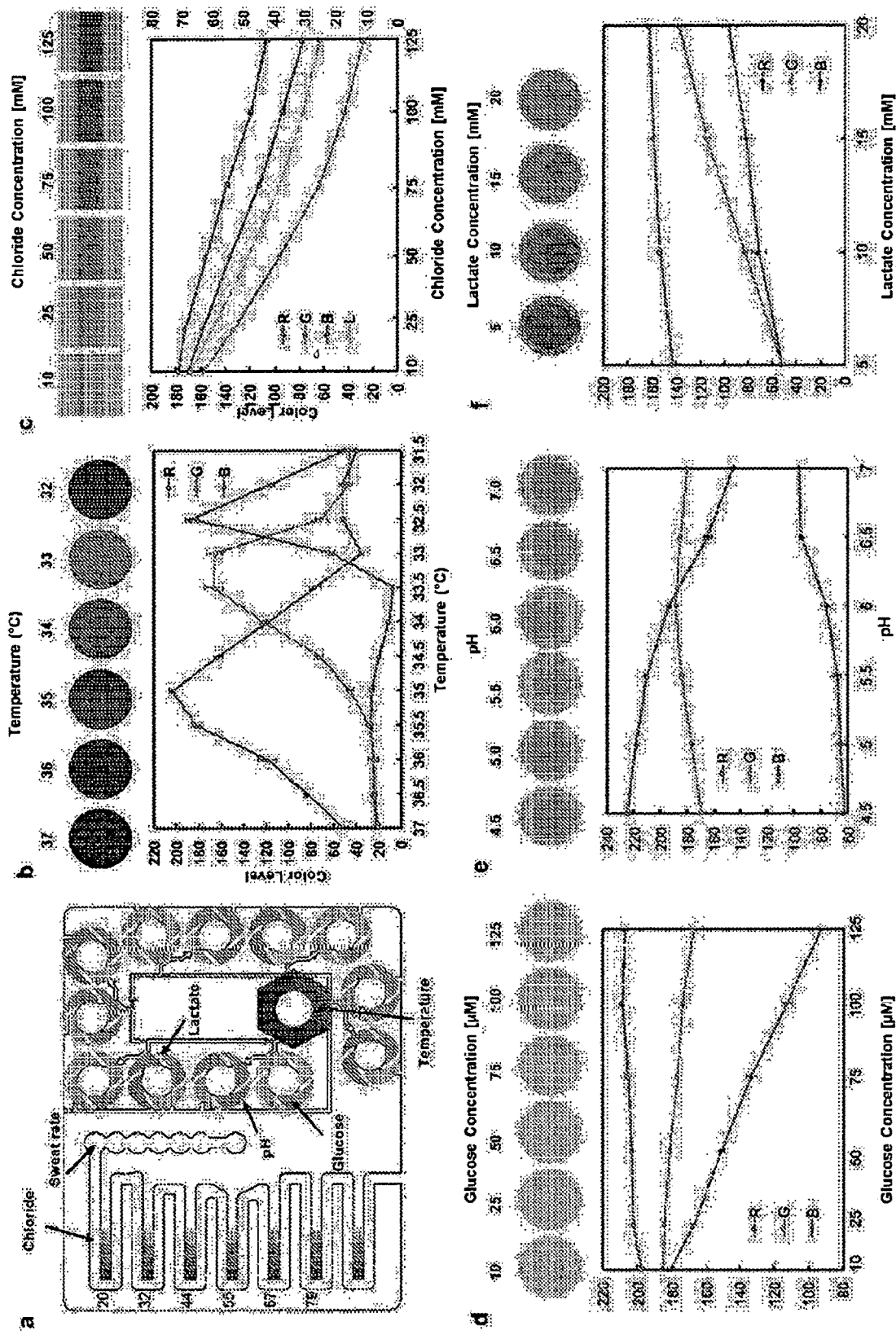

FIG. 24. Panel a: Schematic illustration of device with color reference markers of chloride, glucose, pH and lactate, and number for indicating sweat collection volume. Panel b: Optical images color development of thermochromic liquid crystal temperature sensor according to temperature (top) and color level of each color (bottom). Optical images color development of assay chambers according to sample concentrations (top) and color level of each color (bottom) of (Panel c) chloride, (Panel d) glucose, (Panel e) pH and (Panel f) lactate.

Figure 25:
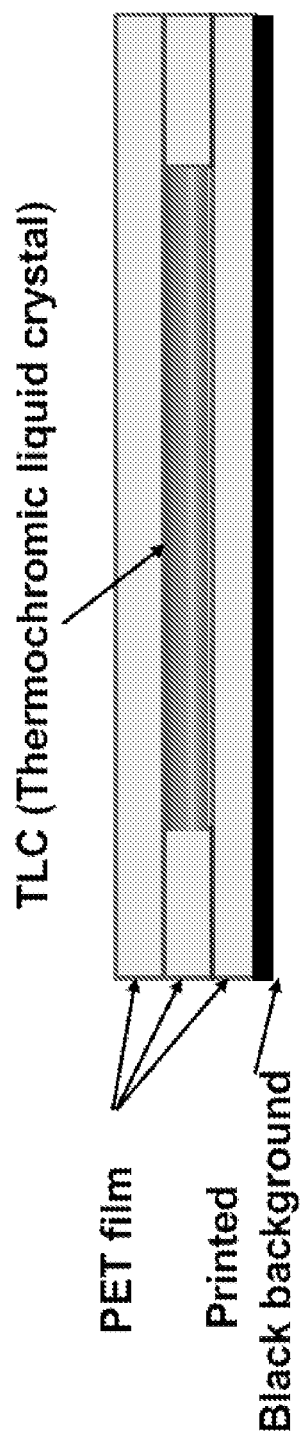

FIG. 25. The structure of temperature sensing film of thermochromic liquid crystal.

Figure 26:
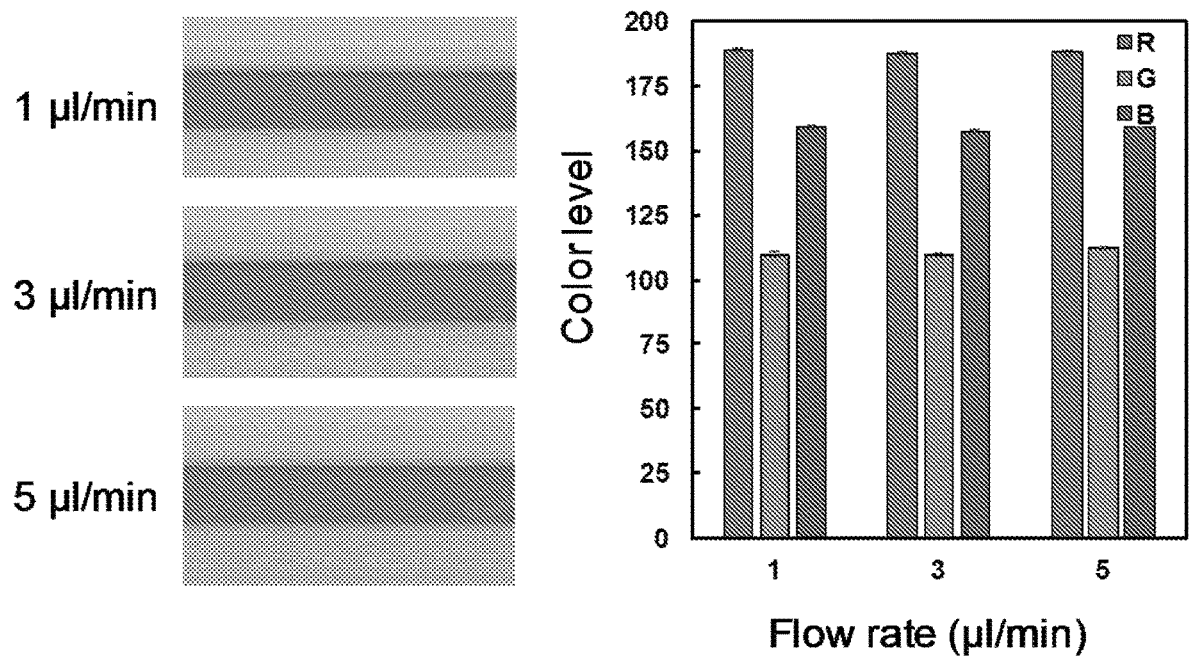

FIG. 26. Color development at various flow rates. (Right) Bar graph of color level vs. flow rate corresponding to each color and flow rate.

Figure 27:
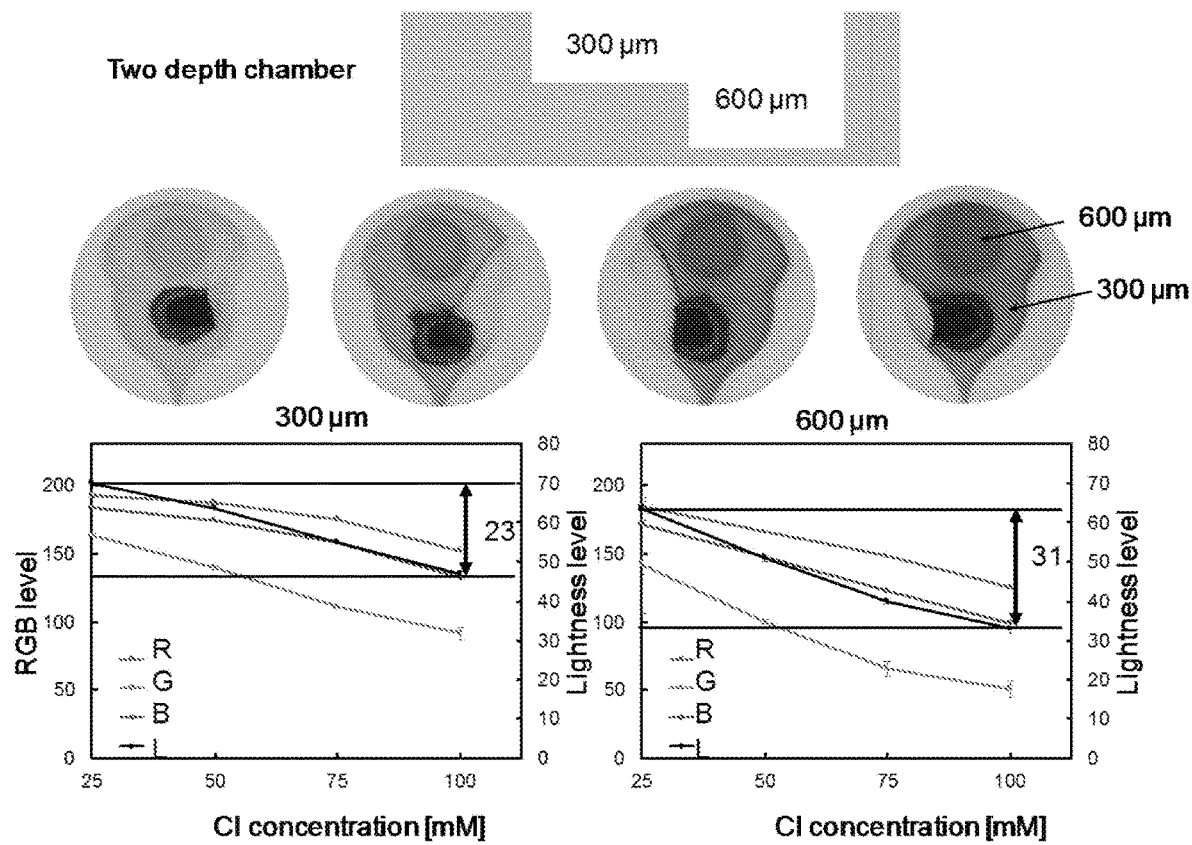

FIG. 27. Color development at different channel depth. (Top) Illustration of two-depth channel chamber. (Middle) images of devices showing regions corresponding to different channel depths (300 μm or 600 μm) and fluid therein. (Bottom) Plots of RGB lightness level vs. Cl concentration (mM) corresponding to the (bottom-left) 300 μm depth chamber and the (bottom-right) 600 μm depth chamber.

Figure 28:
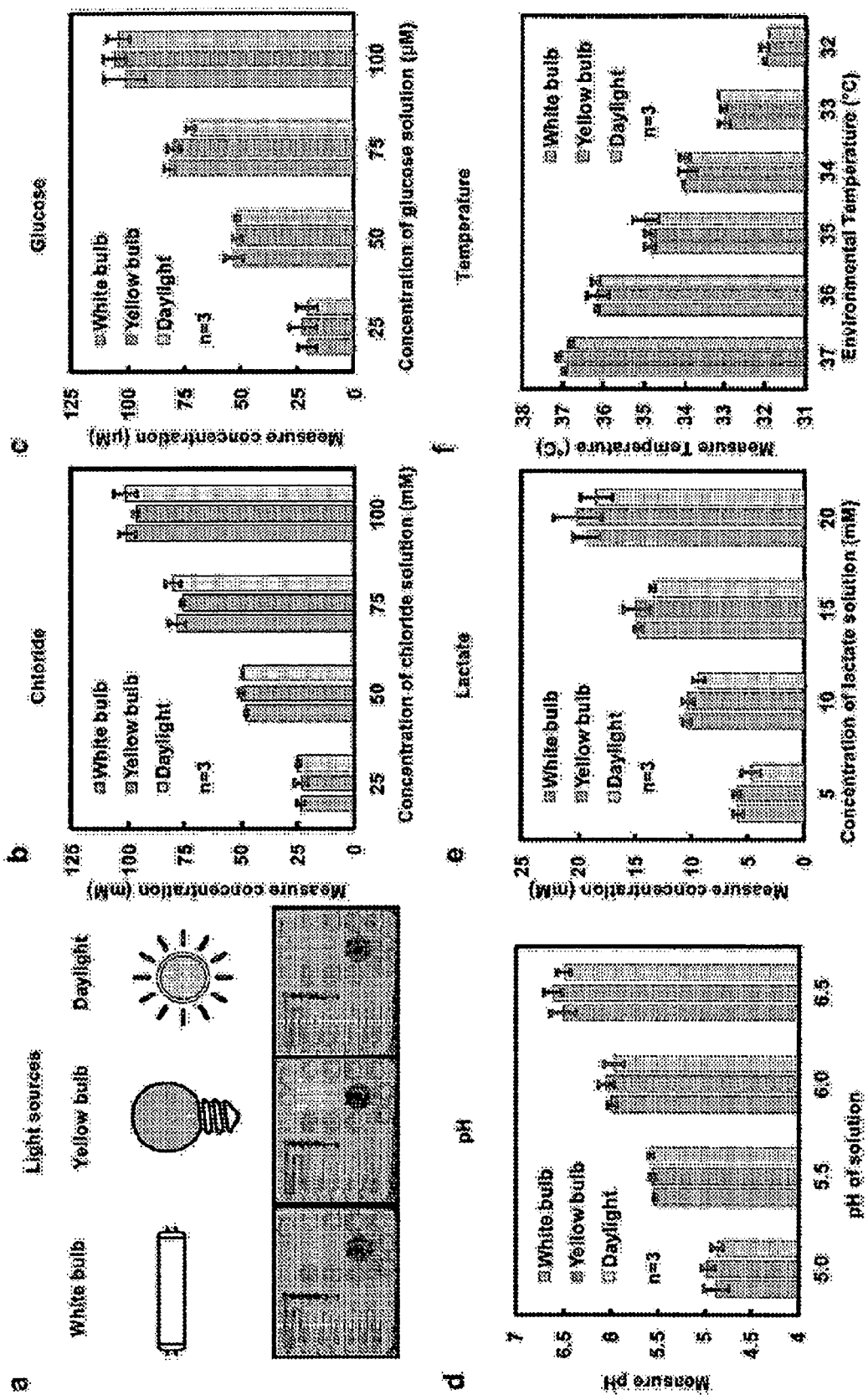

FIG. 28. Panel a: Schematic illustration of in vitro accuracy test of color reference marker in various light sources of white light bulb, yellow light bulb, and daylight. Measured concentration using color reference marker in the device filled with standard solutions of (Panel b) chloride, (Panel c) glucose, (Panel d) pH, (Panel e) lactate, and (Panel f) temperature marker in various light sources.

Figure 29:
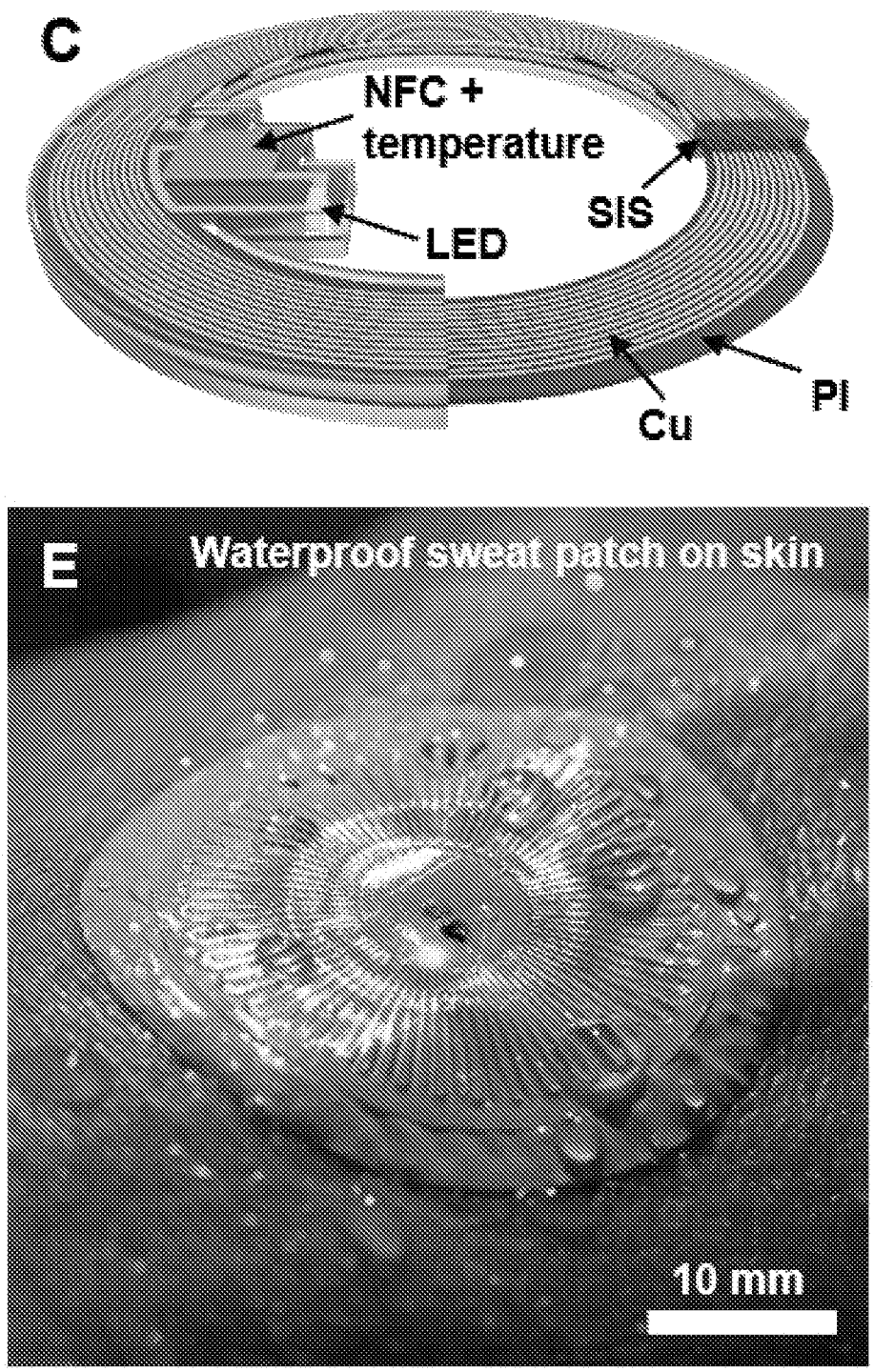

FIG. 29. Panel C is a schematic of an exemplary wearable waterproof device with NFC electronic. Panel E illustrates the wireless operation of the NFC electronics in a wet environment and shows the LED as it emits light through the microfluidic layers.

Figure 30:
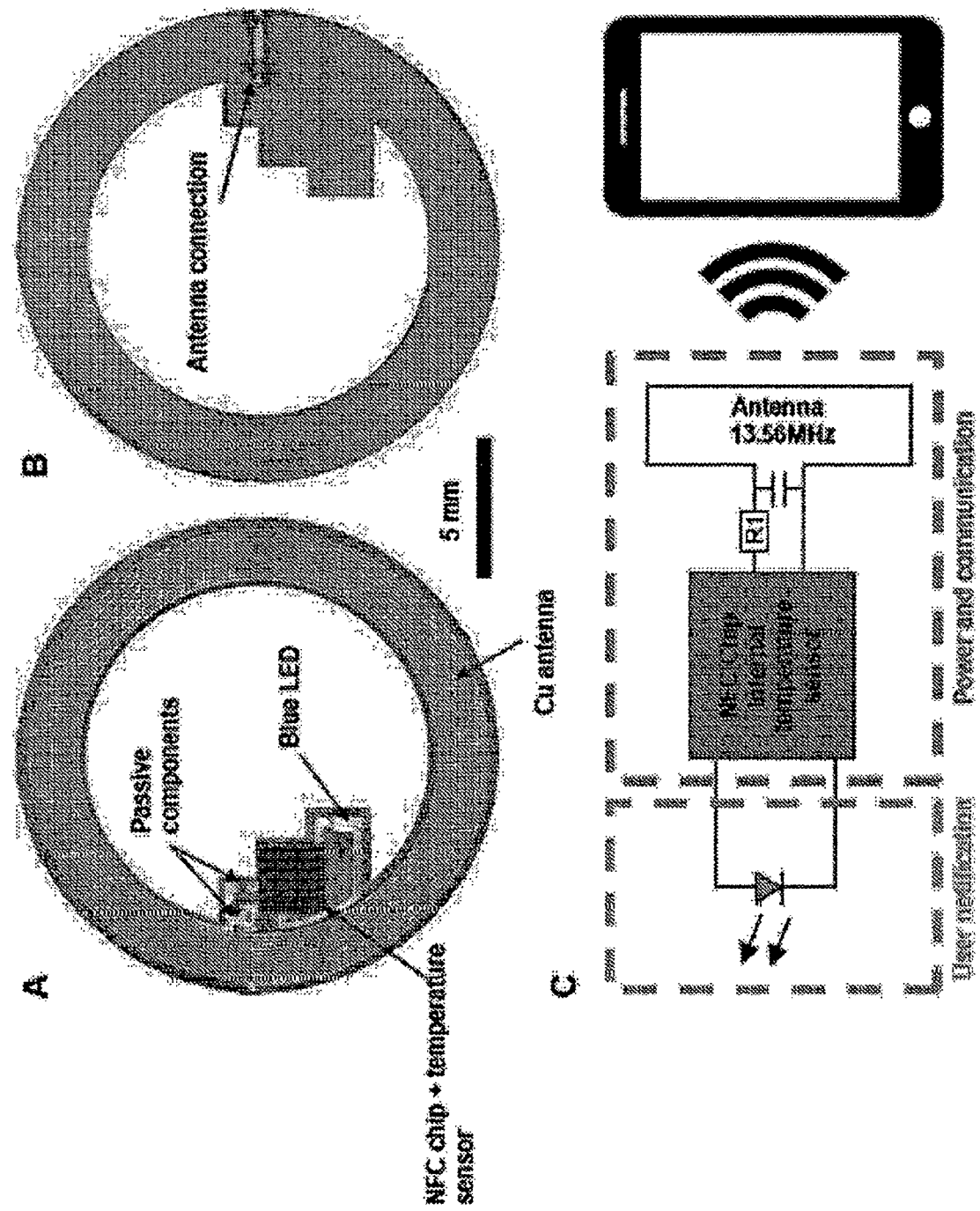

FIG. 30. NFC coil components. Panel A shows a front side view of an exemplary wearable device, such as one of FIG. 29. Panel B shows a backside view of the device of Panel A. Panel C is a schematic of a circuit diagram for skin temperature readout and user notification.

Figure 31:
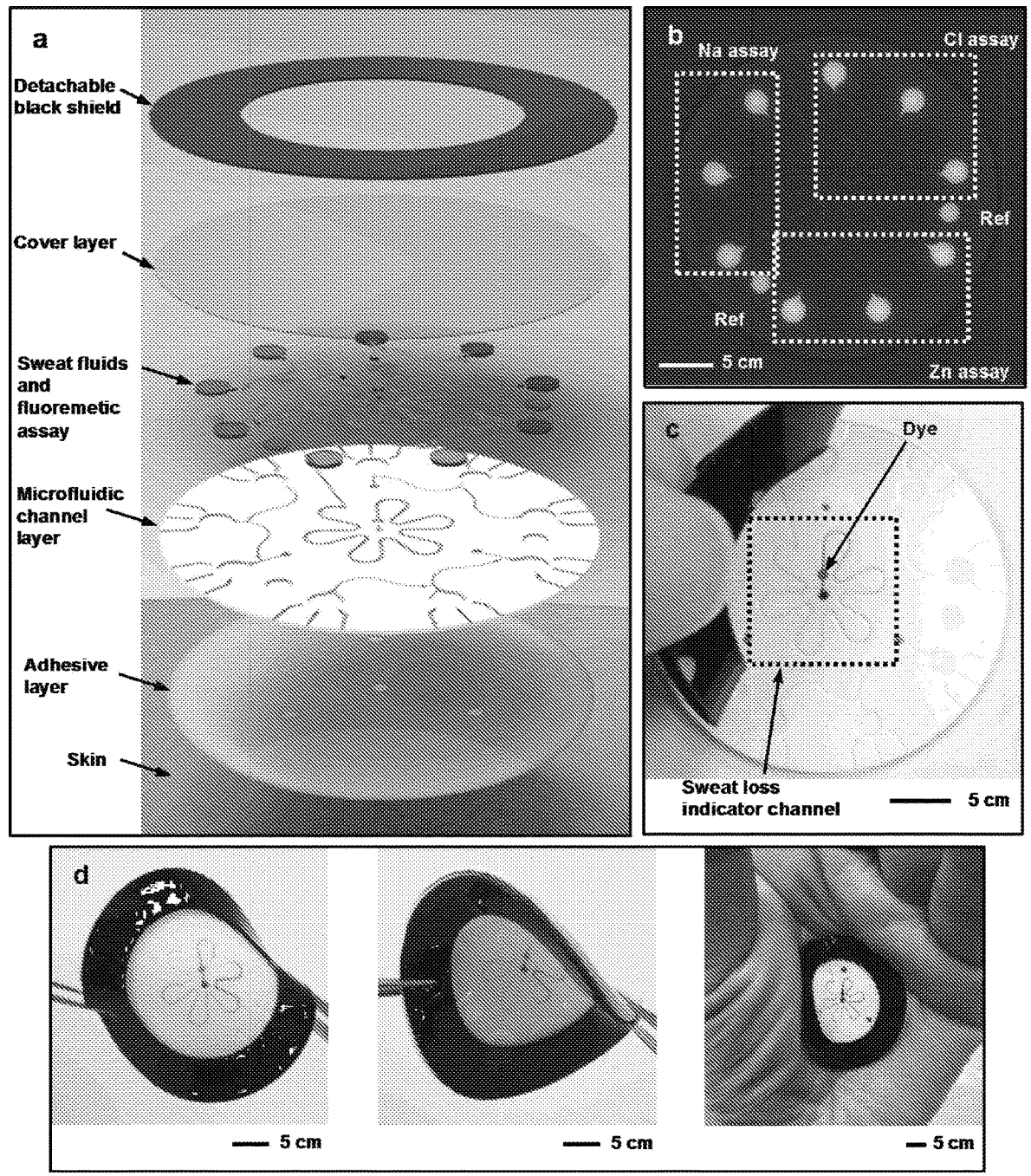

FIG. 31. Schematic illustration and digital images of the microfluidic device for sweat chloride, sodium, and zinc sensing by fluorometric methods. Panel a: Schematic illustrating the exploded view of the micro-fluidic device for fluorescence assays. Panel b: Image illustrating fluorescence signals of chloride, sodium, and zinc probes on the device under the excitation light. Image illustrating (Panel c) the peeling of the detachable black shield from the microfluidic device and (Panel d) the mechanical flexibility under mechanical distortions: forward twisting (left) and backward twisting (center), and on the palm (right).

Figure 32:
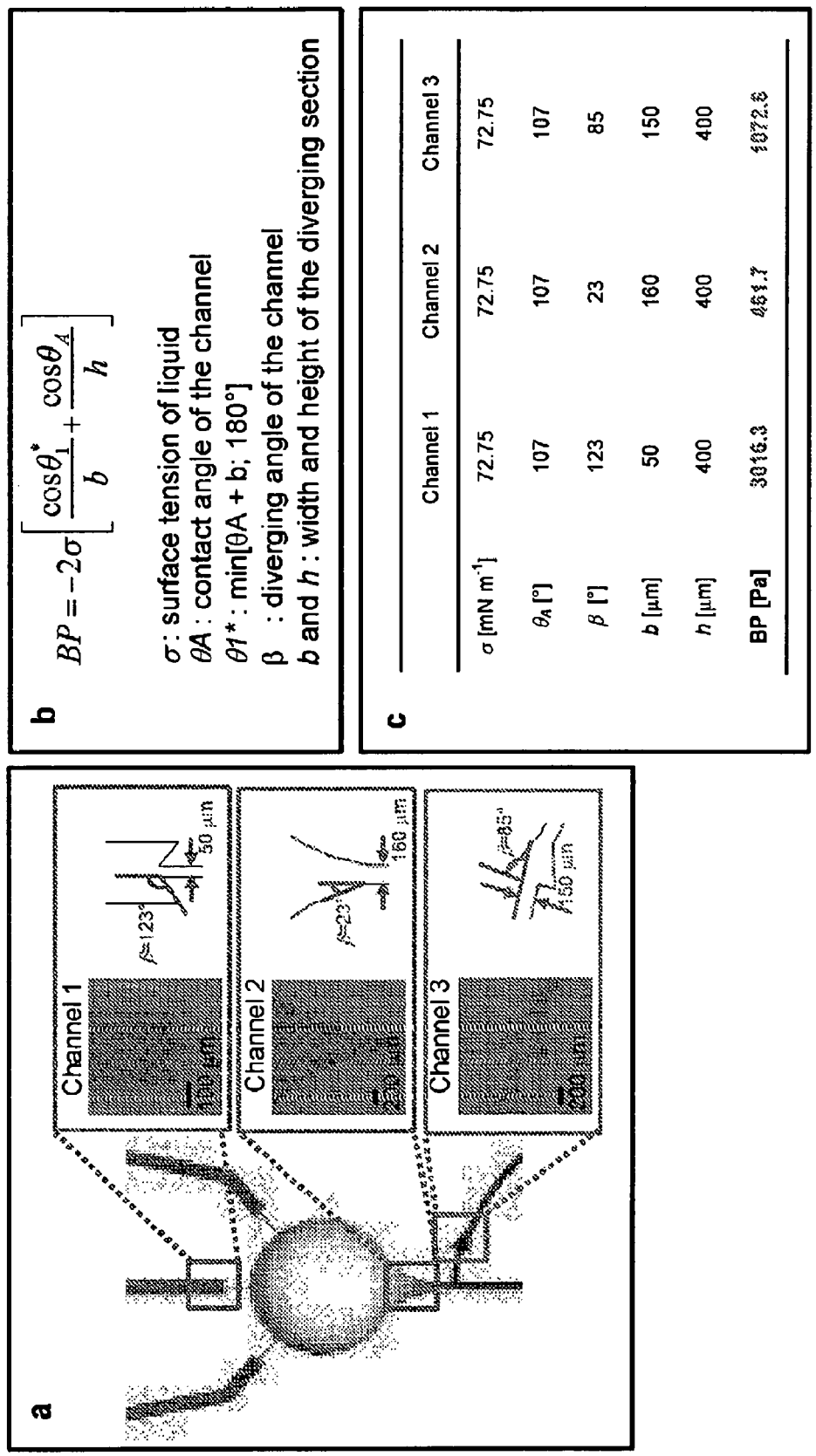

FIG. 32. Description of the design of the micro-fluidic channel. (Panel a) Detailed schematic illustration of a unit cell in a sweat device with a reservoir and three capillary bursting valves. (Panel b) The Young-Laplace equation for calculating the bursting pressures (BP) of the valves. (Panel c) Calculated BP of the three valves and the required parameters for the calculation.

Figure 33:
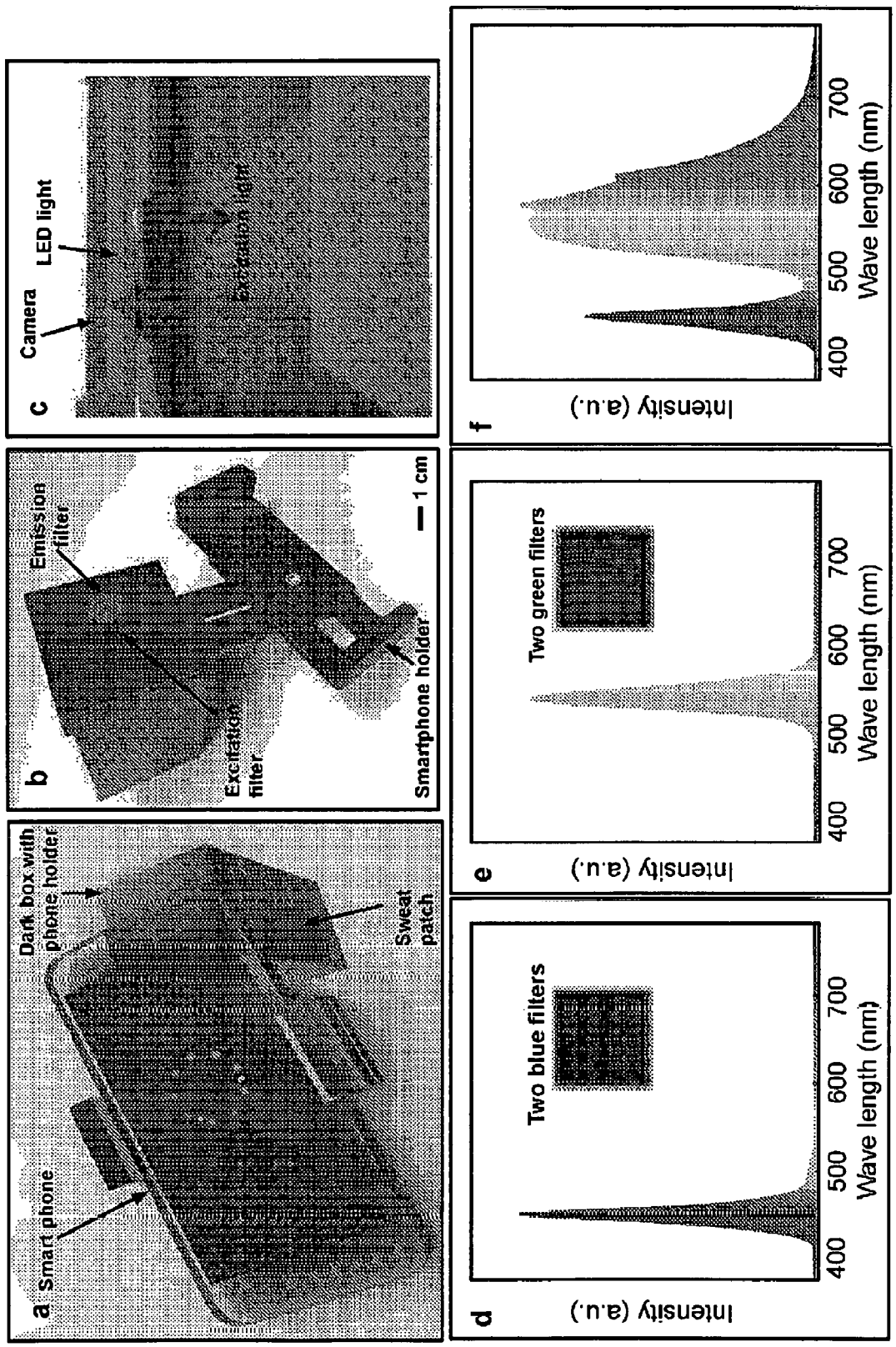

FIG. 33. Description of the design of the smartphone based fluorometric imaging system. (Panel a) Image illustrating the overall concept of fluorescence-imaging system with a smartphone-attached accessory. (Panel b) Image of the photographed of smartphone attachment with the dark box and excitation/emission filters. (Panel c) Image illustrating the fluorometric imaging system in the interfaces of smartphone and the filters. Spectra of smartphone LED light with excitation filters (two dark blue transparent filters) (Panel d) and without filter (Panel e).

Figure 34:
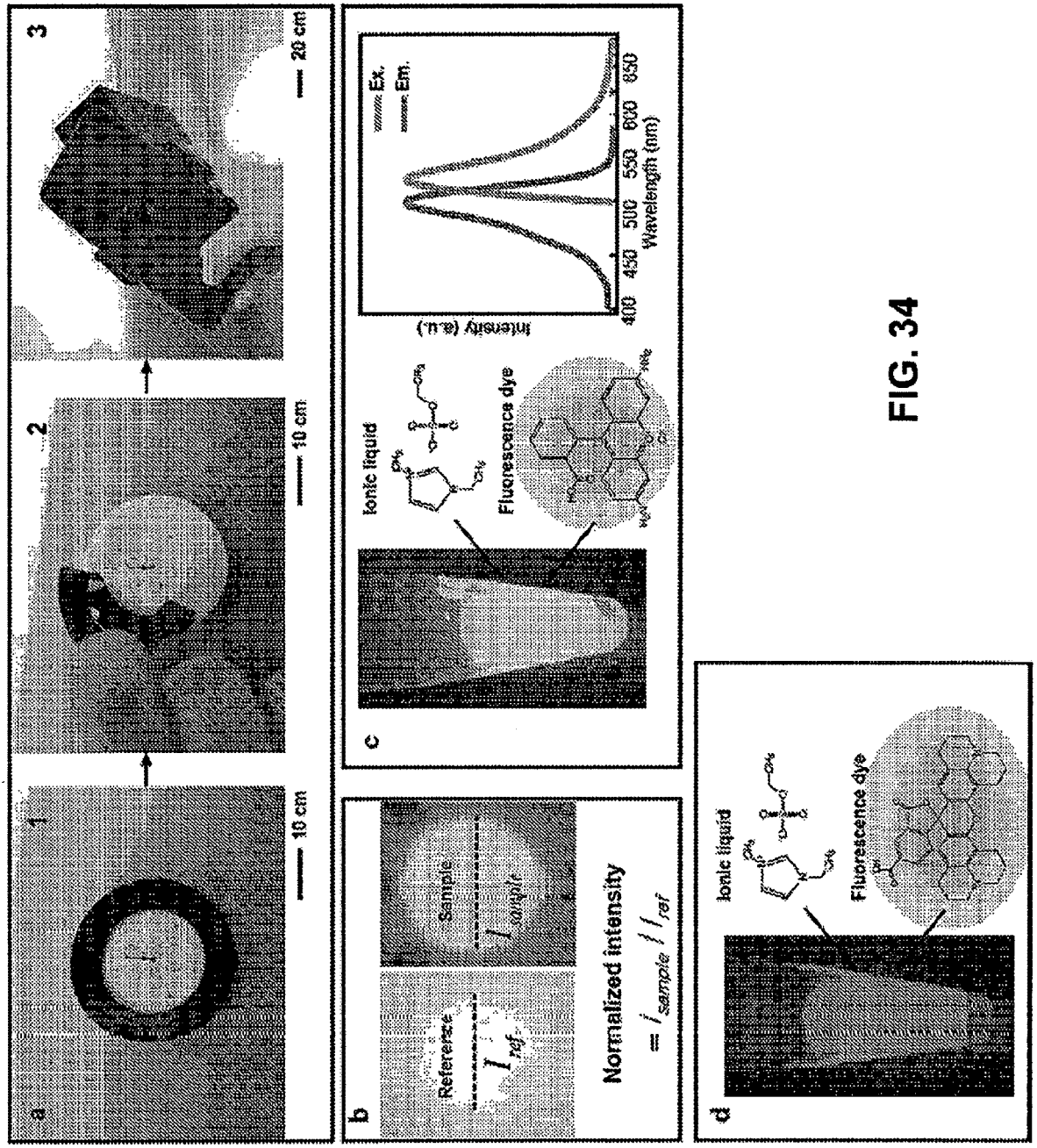

FIG. 34. (Panel a) Procedure of the fluorometric assay: 1. Collection of sweat using a sweat device 2. Peeling the black shield 3. Taking a photo of the device using a smartphone attached accessory. (Panel b) Method of fluorescence calibration. Fluorescence reference material consisting of an ionic liquid and a green fluorescence dye (Panel c) and red reference dye (Panel d).

Figure 35:
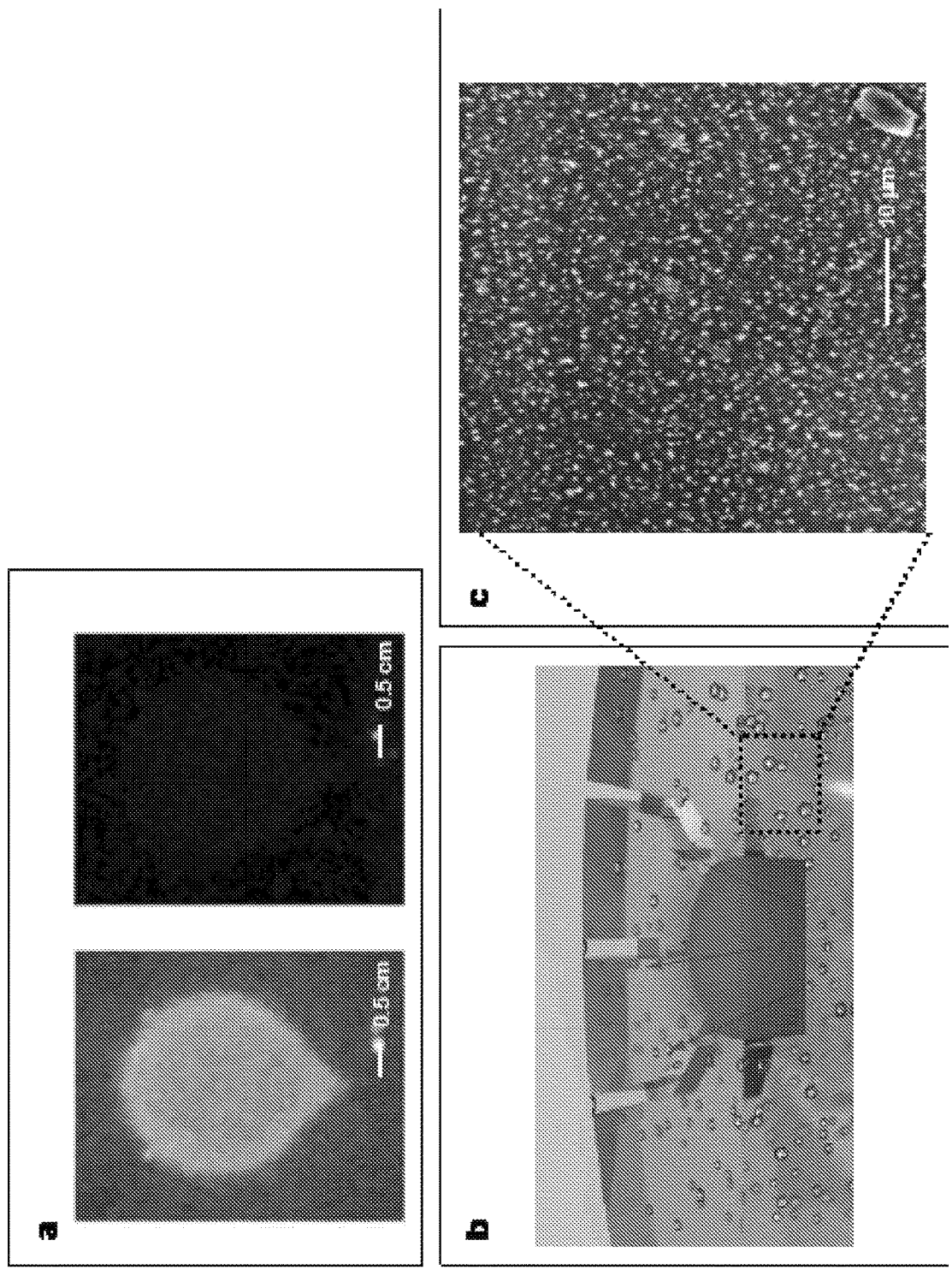

FIG. 35. Effect of white PDMS on fluorescence intensity. (Panel a) Difference of the fluorescence image between white and transparent PDMS devices. (Panel b) Schematic illustrating the reflection of fluorescence by the titanium oxide particles included in the white PDMS. (Panel c) SEM image of a white PDMS.

Figure 36:
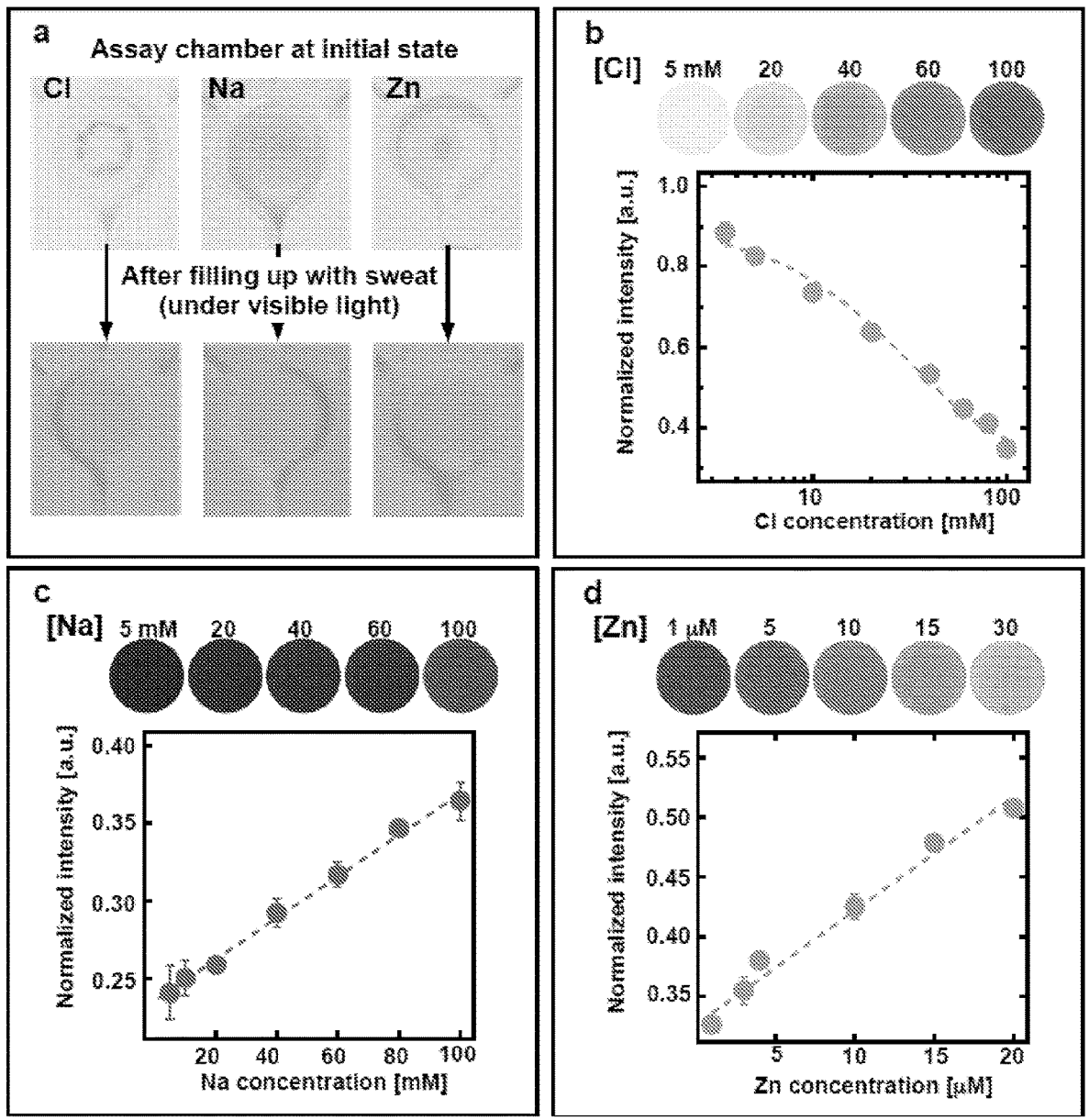

FIG. 36. Fluorescence images of chloride, zinc, and sodium assays and its light intensity dependence on the concentration. (Panel a) Image illustrating the micro reservoirs for the assays before (upper) and after (lower) filled up with sweat under visible light. Changes of the fluorescence and its normalized intensity at various concentrations of (Panel b) chloride, (Panel c) sodium, and (Panel d) zinc.

Figure 37:
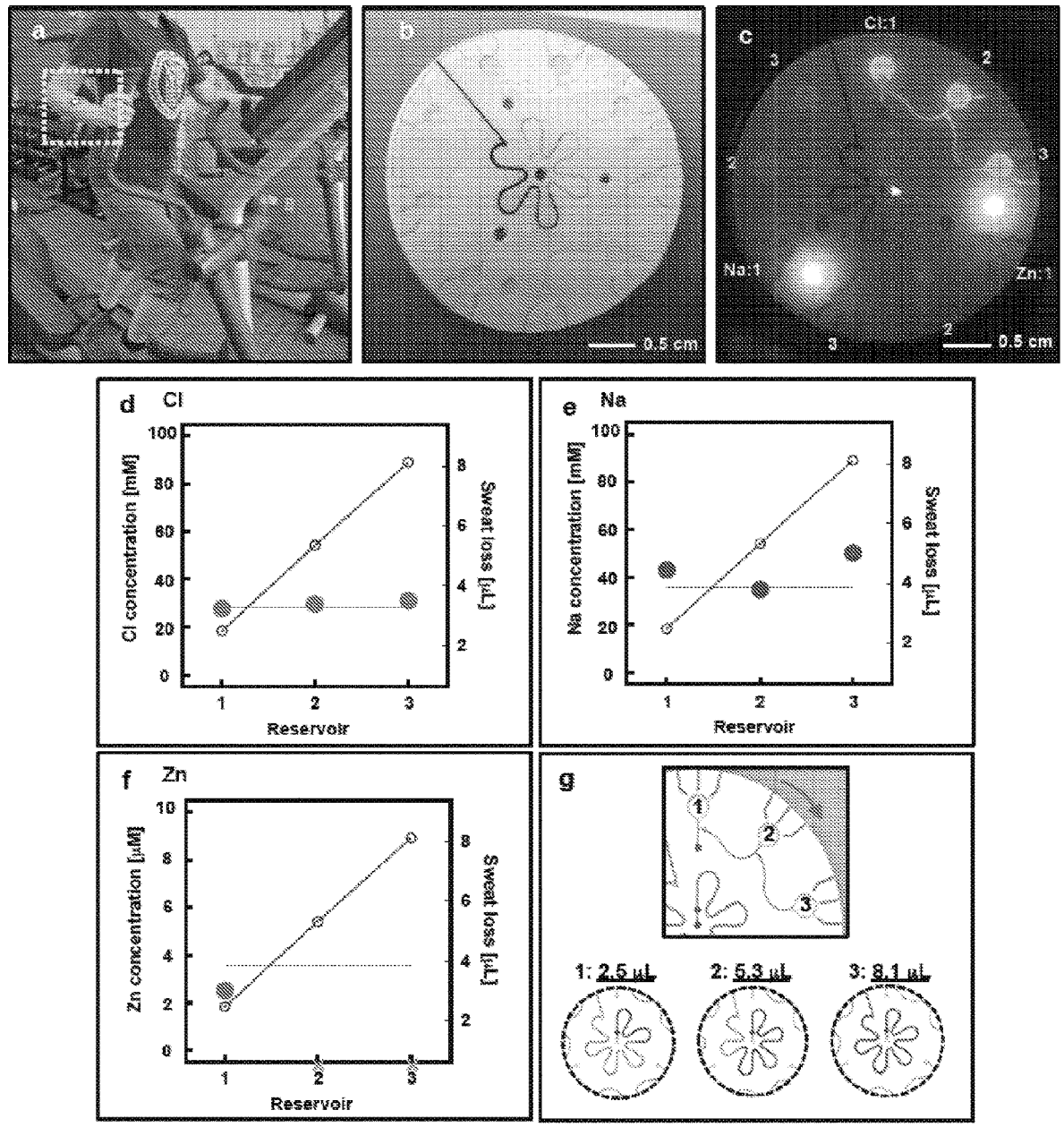

FIG. 37. (a) Photograph of a subject wearing a microfluidic patch during sweat testing. Images of the sweat patch without the black shield after sweat collection under (Panel b) visible light and (Panel c) the blue light emitted by a smartphone. (Panel d) Calculated concentrations of sweat (Panel d) chloride (green closed circles), (Panel e) sodium (blue closed circles), and (Panel f) zinc (pink closed circles) with the estimated sweat loss. The solid green, blue, and pink lines indicate the concentrations measured by ion chromatography for chloride, ICP-MS for zinc, and atomic absorption spectrometry for sodium in the sweat. (Panel g) Changes of estimated sweat loss with being filled up the micro reservoirs and center microchannel structure.

Figure 38:
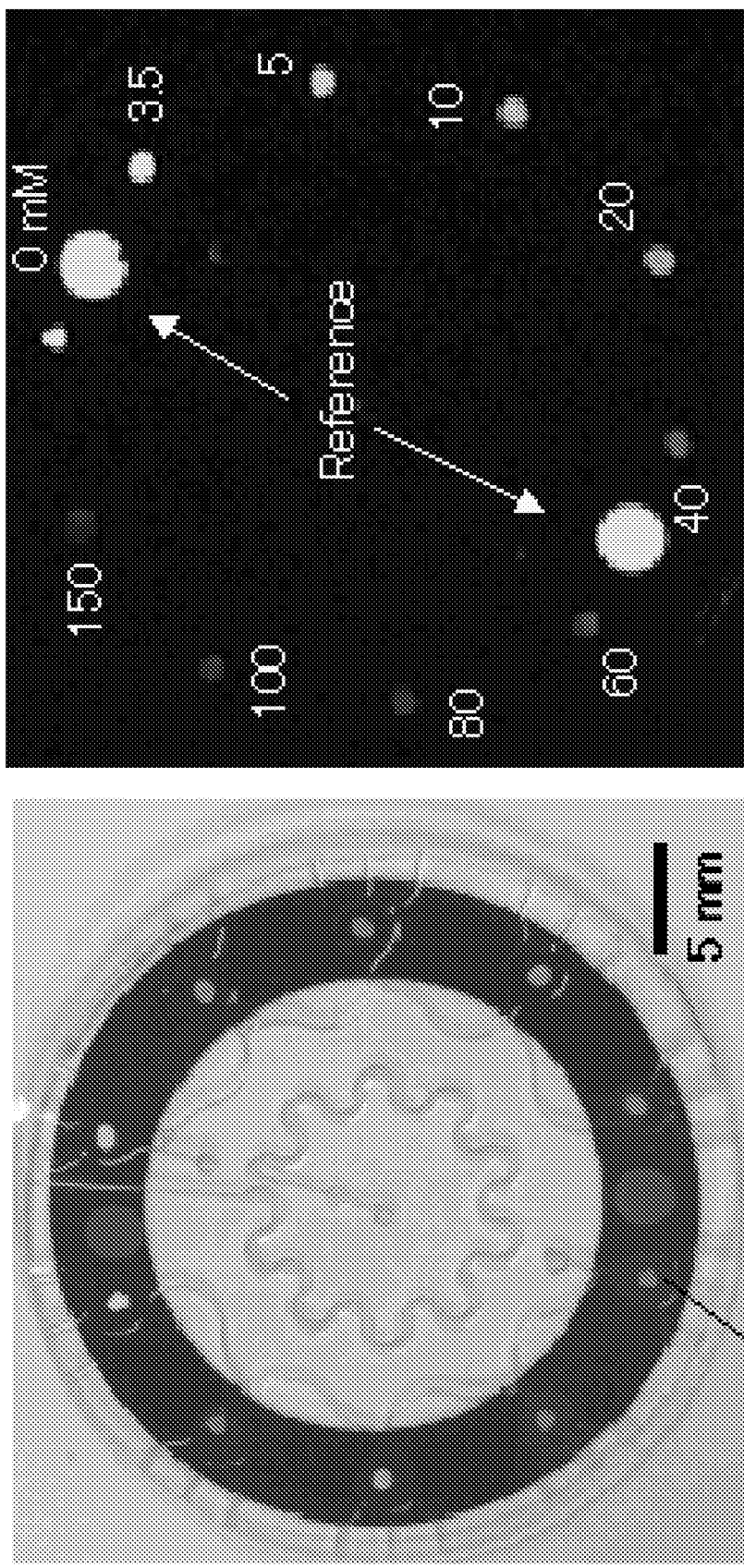

FIG. 38. (Left) Light image and (right) dark image corresponding to fluorometric chloride assay using 0.3 µL of artificial sweat containing 0-150 mM chloride.

Figure 39:
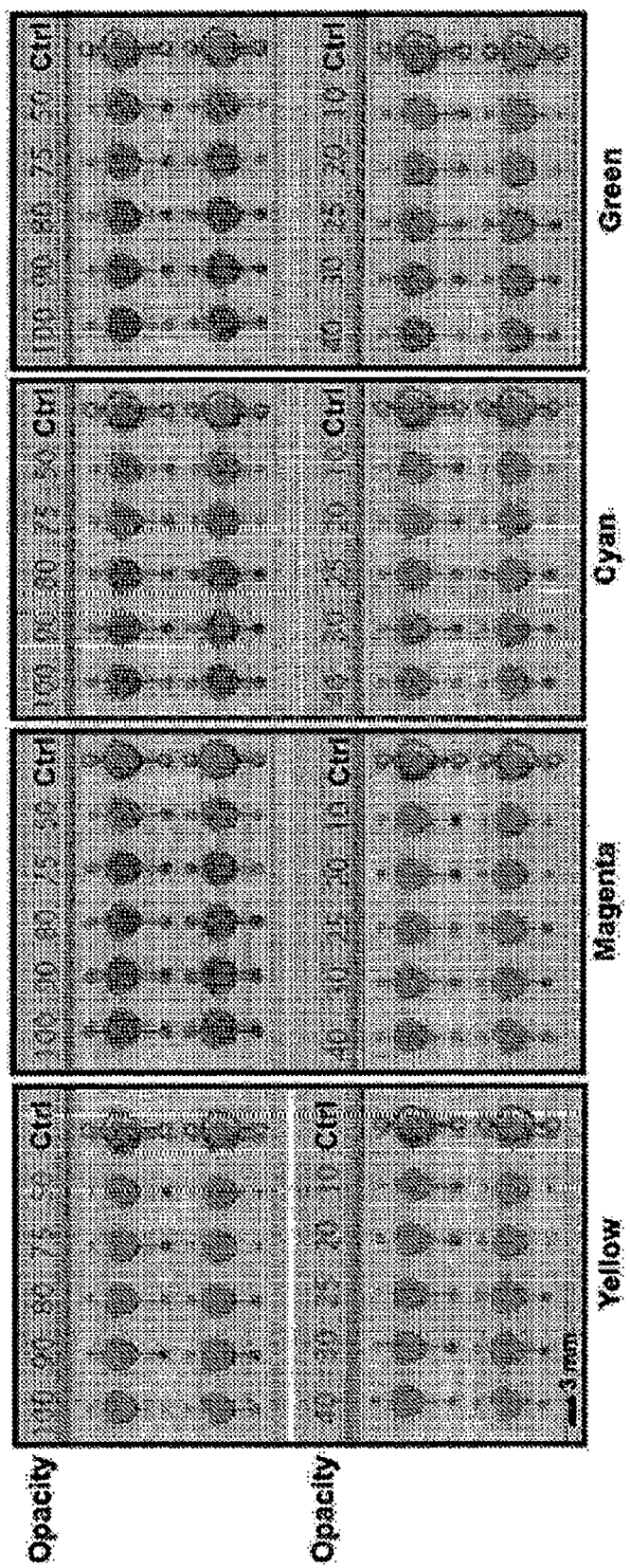

FIG. 39. Sample analysis wells with overprinting colors (Yellow, Magenta, Cyan, Green) at different opacities (100, 90, 80, 75, 50, 40, 30, 25, 20, 10) and two control points per pattern. Control points have no printing, but contain printed overlay material (PET) to eliminate path length variations. Duplication of each row eliminates channel height variation. Colorimetric assay is silver chloranilate for a 75 mM concentration test solution.

Figure 40:
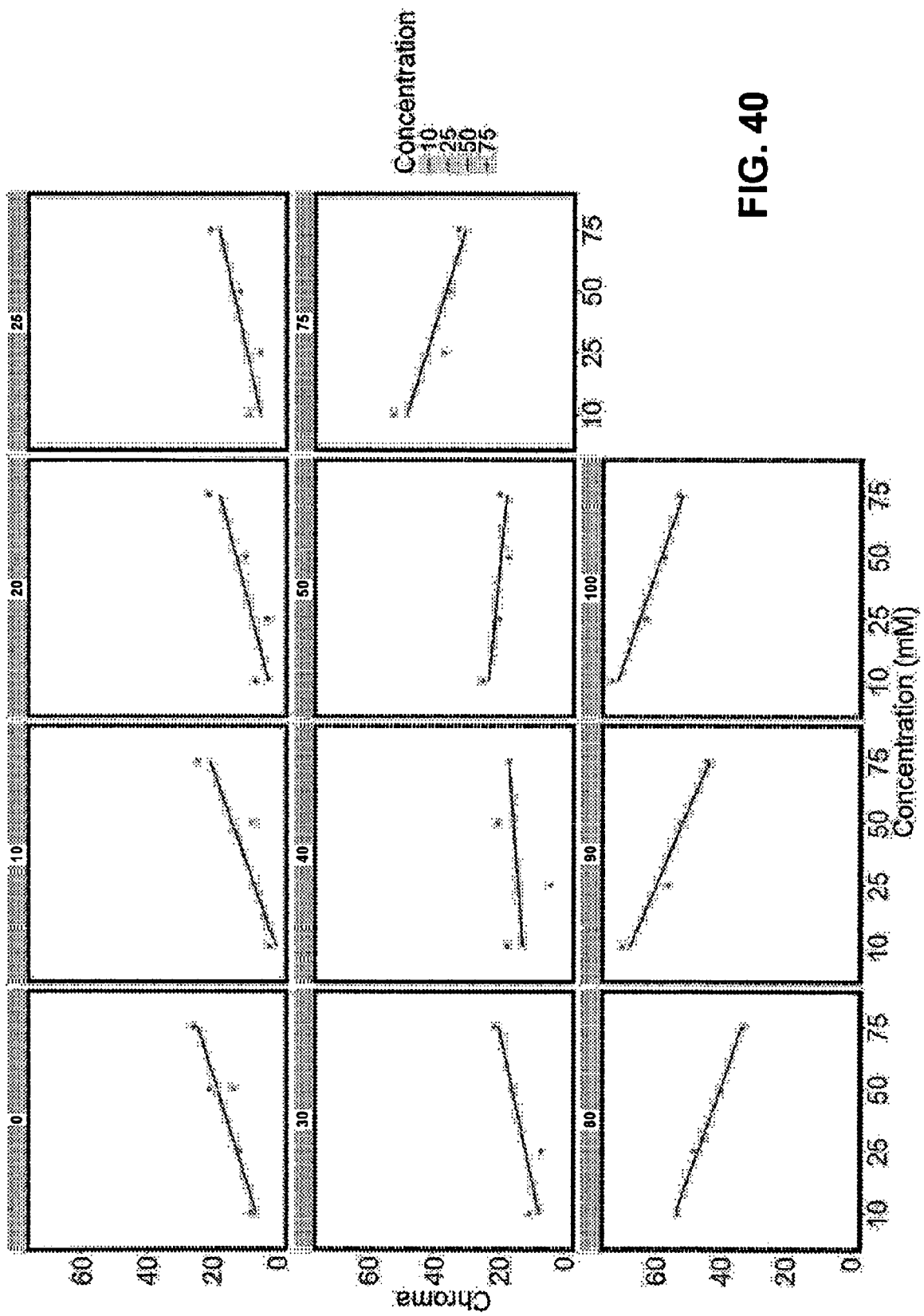

FIG. 40. Facet plot of the color Green of measured chroma values versus concentration (known). The facets represent the different opacities. The overprints were made via laser printer.

Figure 41:
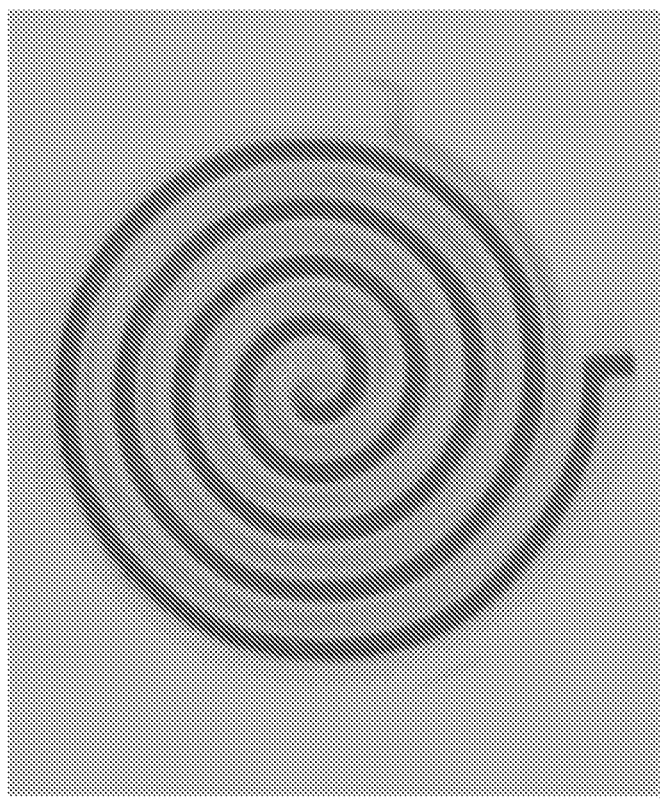
Figure 41:
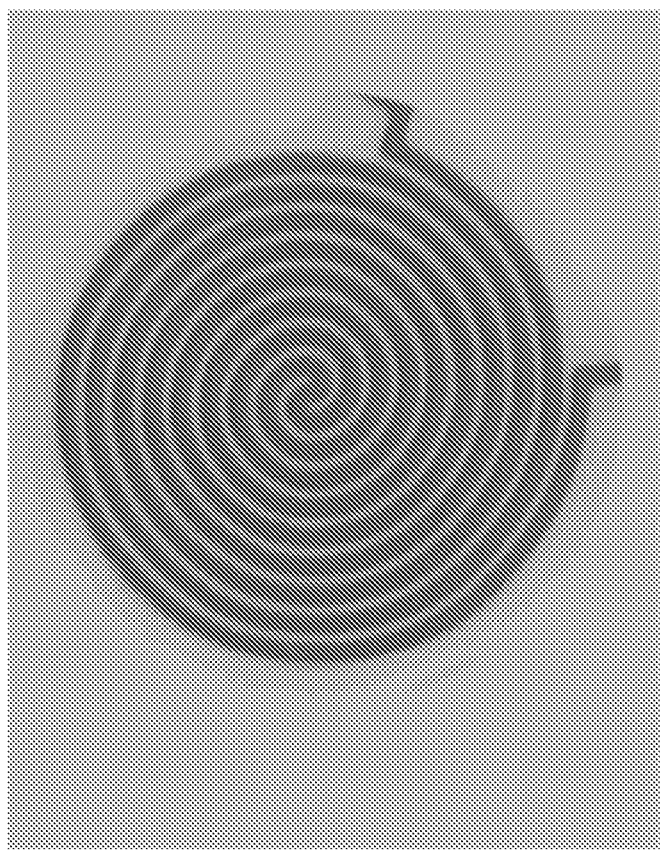

FIG. 41. Microfluidic channels forming a "reservoir" that spatially holds 5 µL of fluid. When halfway full, the direction of fill changes thereby indicating both visually and via motion the current volume of collected fluid with respect to the total volume.

Figure 42:
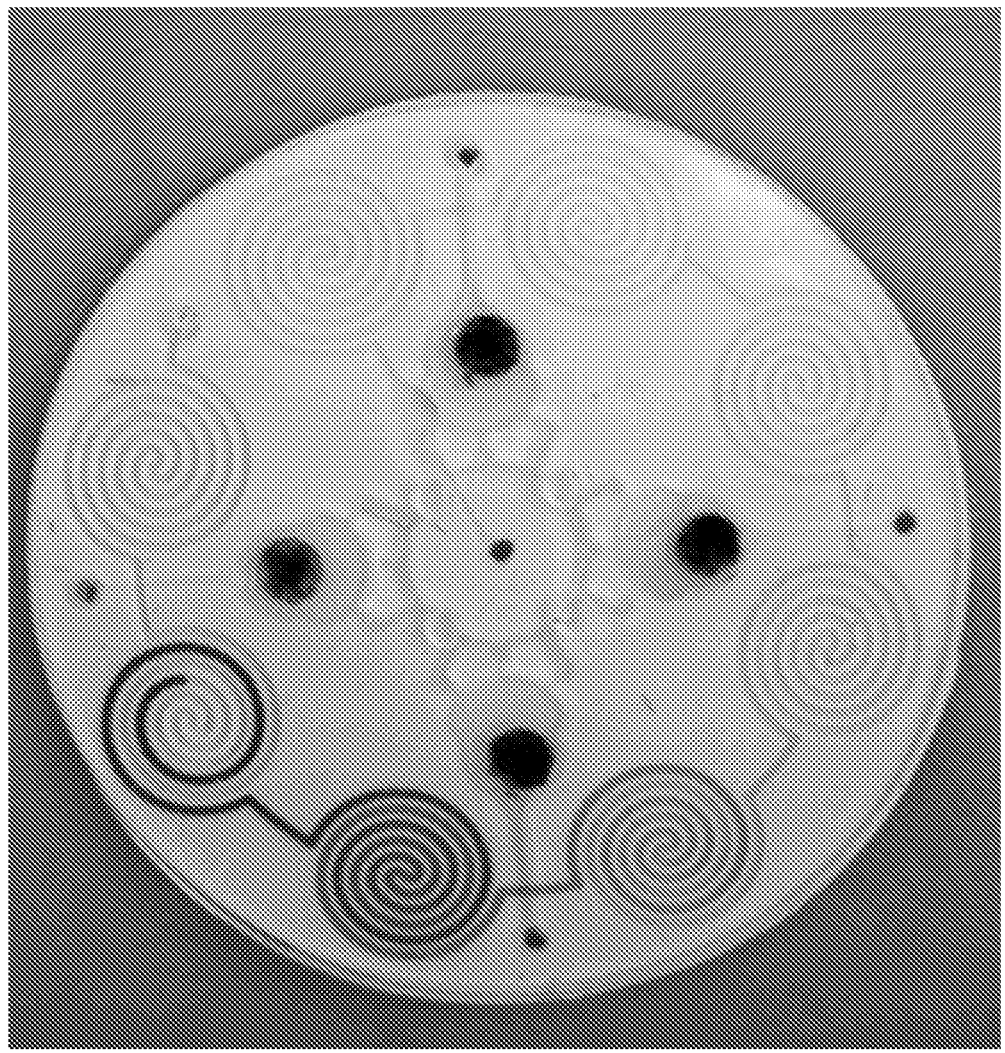

FIG. 42. A representative device showing a network of channel "reservoirs" that hold a larger volume of collected sweat with a "digital" indication of the total volume of collected sweat.

Figure 43:
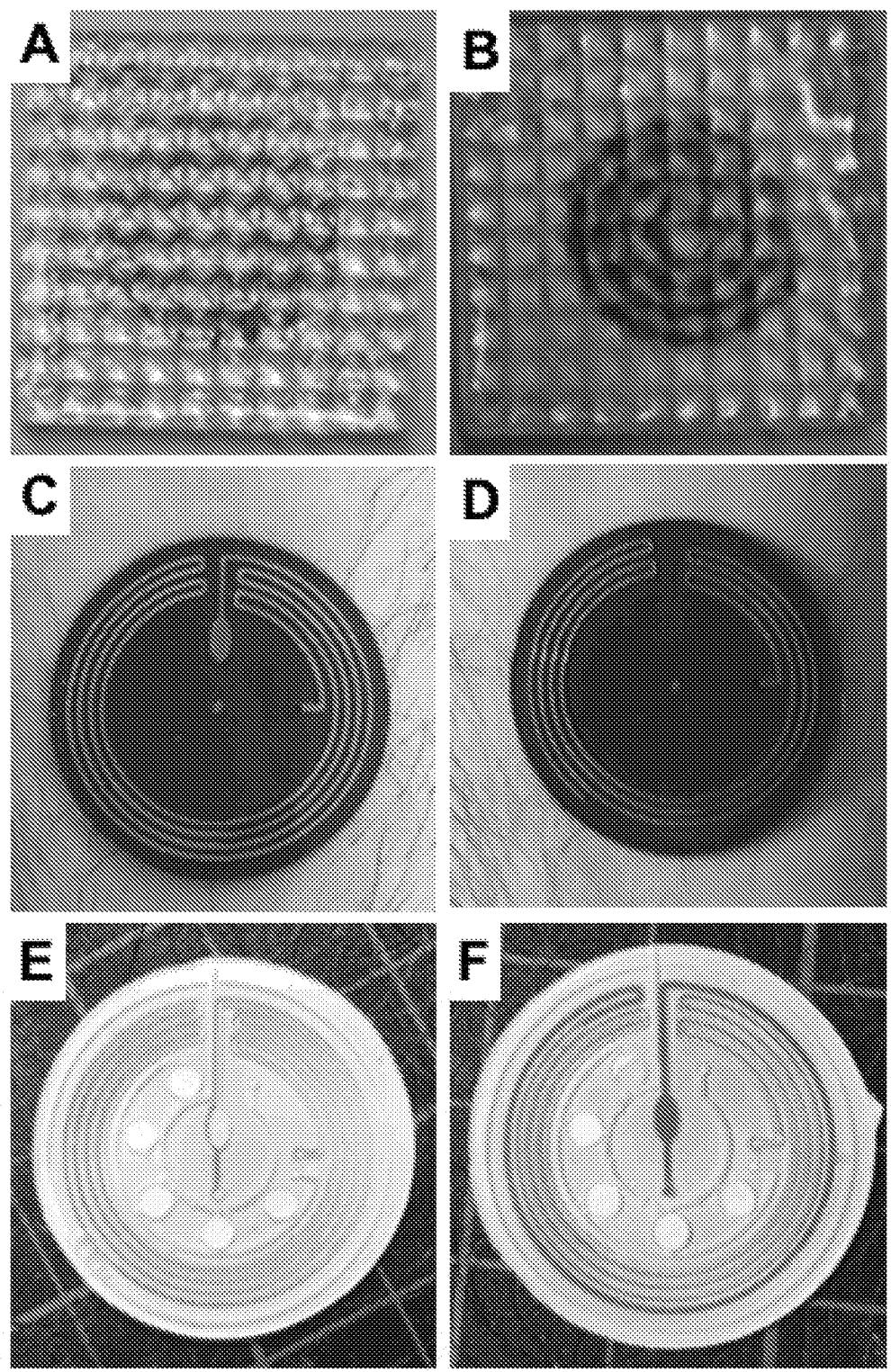

FIG. 43. Representative images of lens structures (Panels A, B), surface roughness (Panels C, D), and embedded particles (Panels E, F) with underlaid color structures in the absence (Panels A, C, E) and presence (Panels B, D, F) of sweat.

Figure 44:
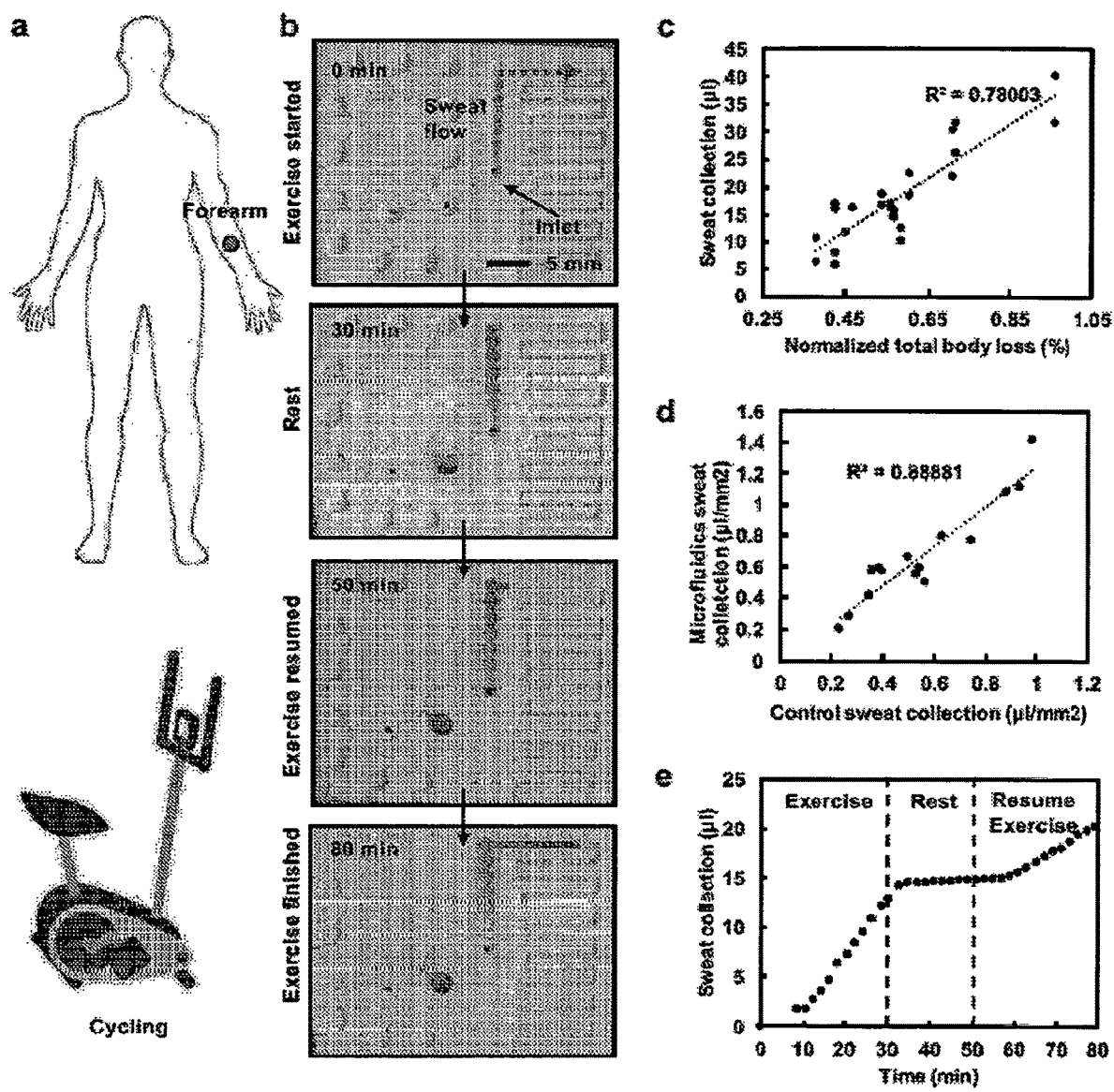

FIG. 44. Panel a: Schematic illustration of mounting position of sweat collection device on the body at forearm and type of exercise. Panel b: Optical image of microfluidic device spotted with blue dye that mixes with sweat. The extent of blue dye in the channel during sweat provides a measure of total sweat volume at any given instant in time. Panel c: Correlation of sweat collection for a microfluidic device from the anterior forearm versus the normalized total body loss (based on initial weigh-in and final weigh-out with no fluid intake or restroom use during exercise). Panel d: Correlation of sweat collection for a microfluidic device versus an absorbent patch. Panel e: Cumulative local sweat loss versus time measured from the forearm with a microfluidic device during exercise, while at rest, and during a subsequent exercise session.

Figure 45:
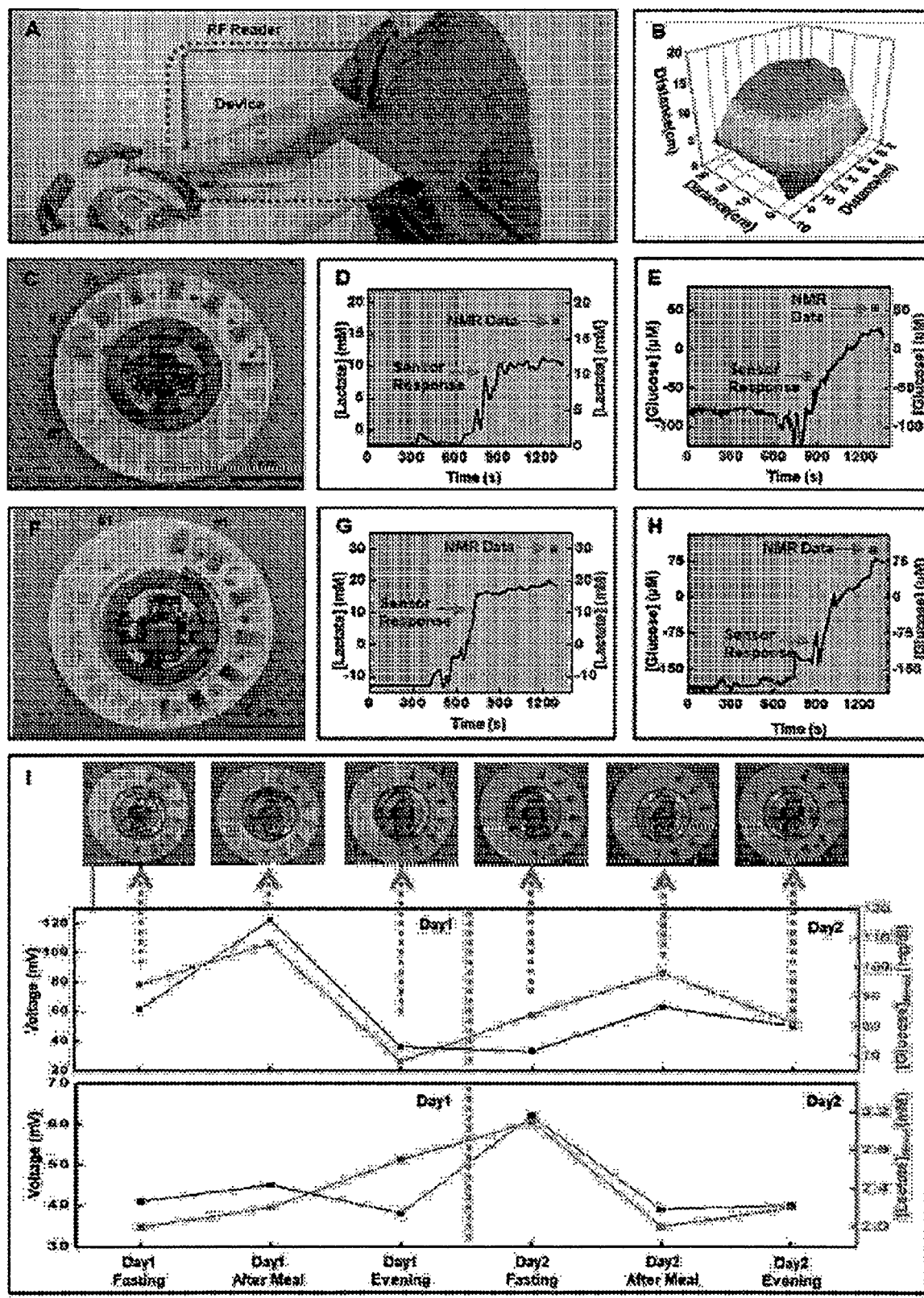

FIG. 45. Human trials. (Panel A) Photograph of a subject adorning the wireless battery-free hybrid sensor system. (Panel B) Reading distance of device with large NFC antenna. (Panel C) Image of complete system captured after a bout of cycling by a subject. Real-time wirelessly acquired sweat concentration levels for (Panel D) lactate and (Panel E) glucose. (Panel F) Image of complete system captured after a bout of cycling by a subject. Real-time wirelessly acquired sweat concentration levels for (Panel G) lactate and (Panel H) glucose. (Panel I) Correlation of data acquired from biofuel cell-based glucose and lactate sweat sensors with that acquired from blood glucose and lactate meter over a period of two days for subject #1. (Panels D, E, G and H) Blue region represents no sweat while green indicates sweating of the human subjects.

Figure 46:
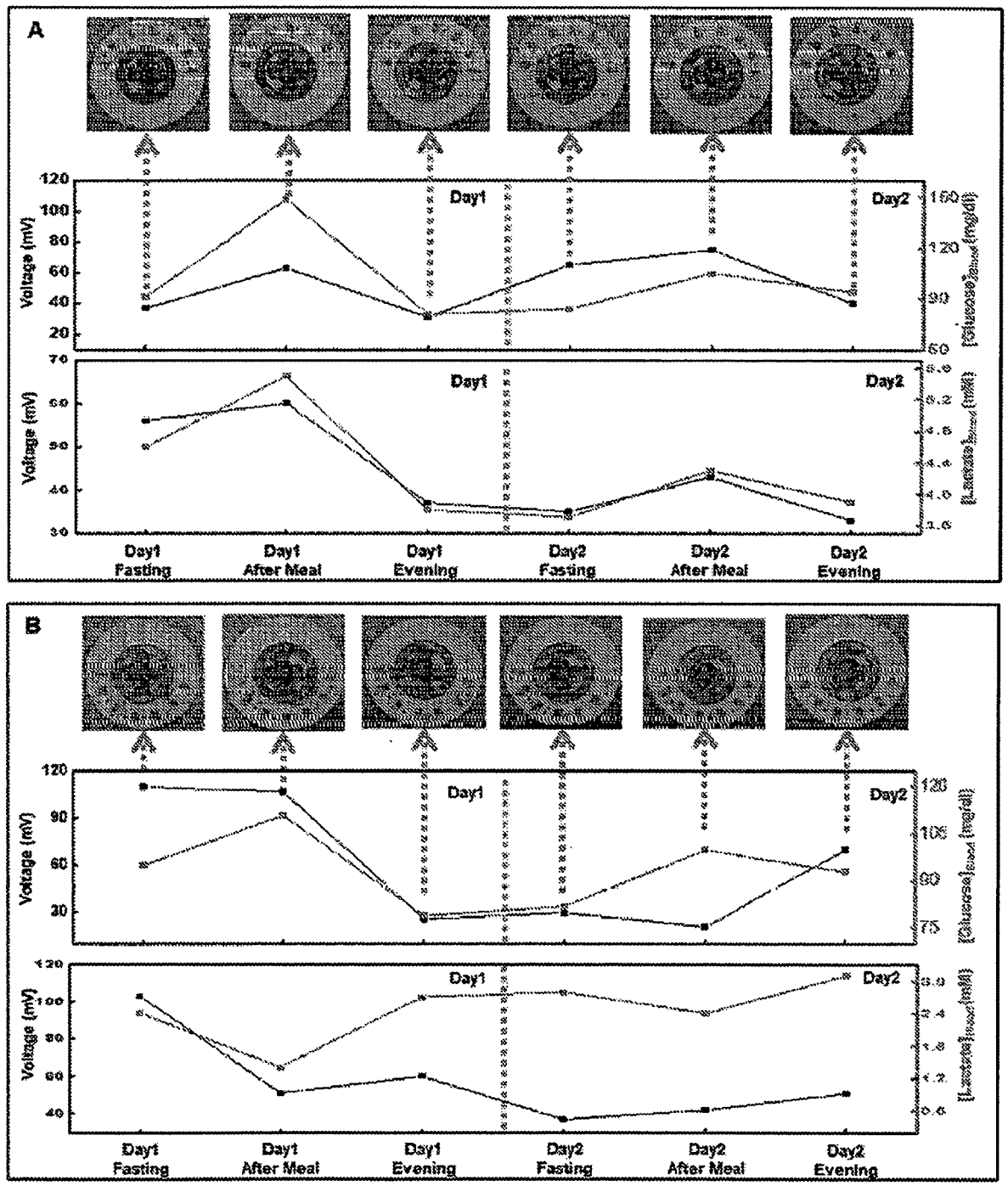

FIG. 46. Correlation of data acquired from biofuel cell-based glucose and lactate sweat sensors with that acquired from blood glucose and lactate meter over a period of two days for (Panel A) subject #2 and (Panel B) subject #3.

Figure 47:
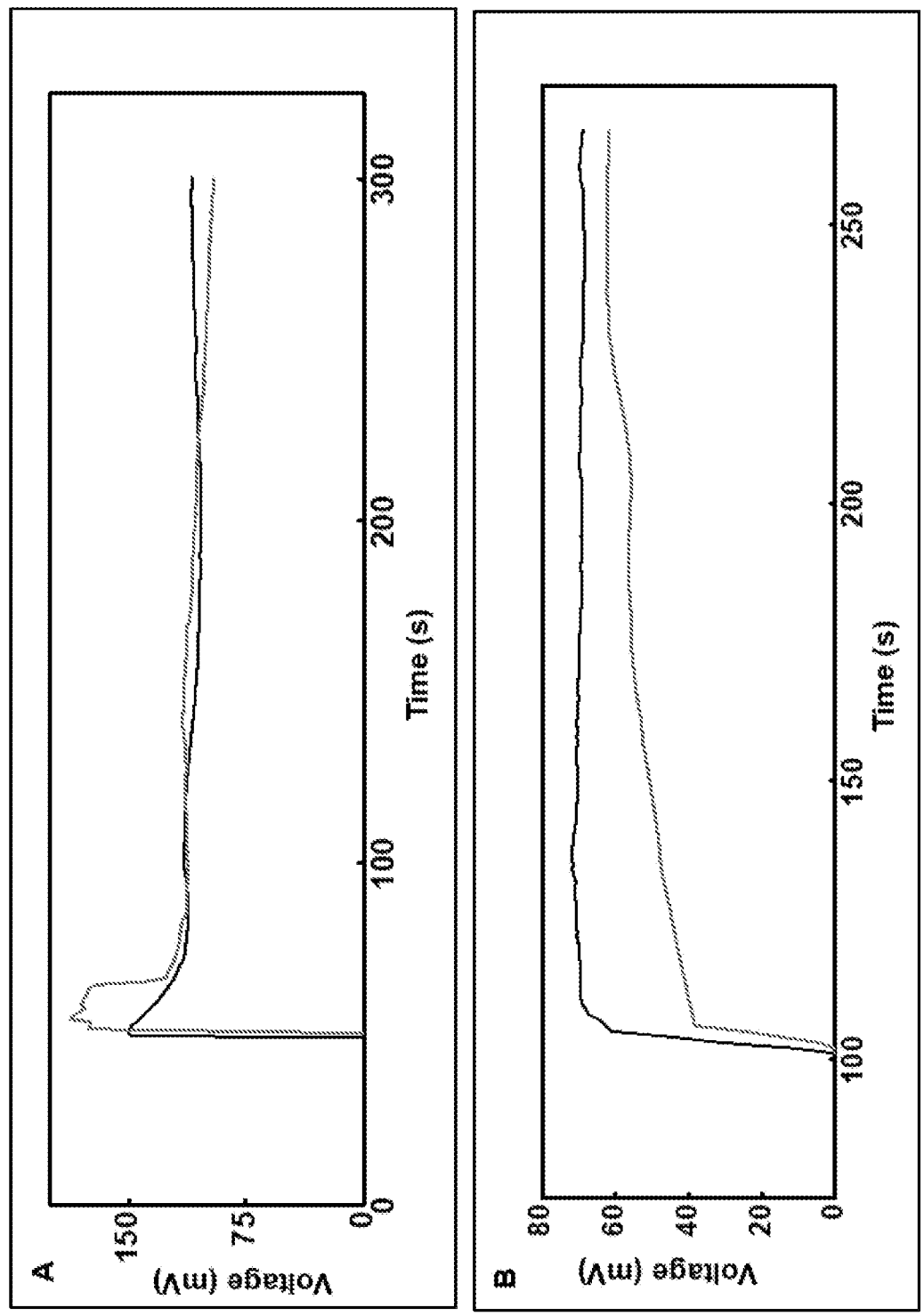

FIG. 47. (A) Comparison of signal of fresh, unused glucose sensor (black) with that obtained from one after two-day human trial (red) when exposed to 300 µM glucose solution. (B) Comparison of signal of fresh, unused lactate sensor (black) with that obtained from one after two-day human trial (red) when exposed to 10 mM lactate solution.

Figure 48:
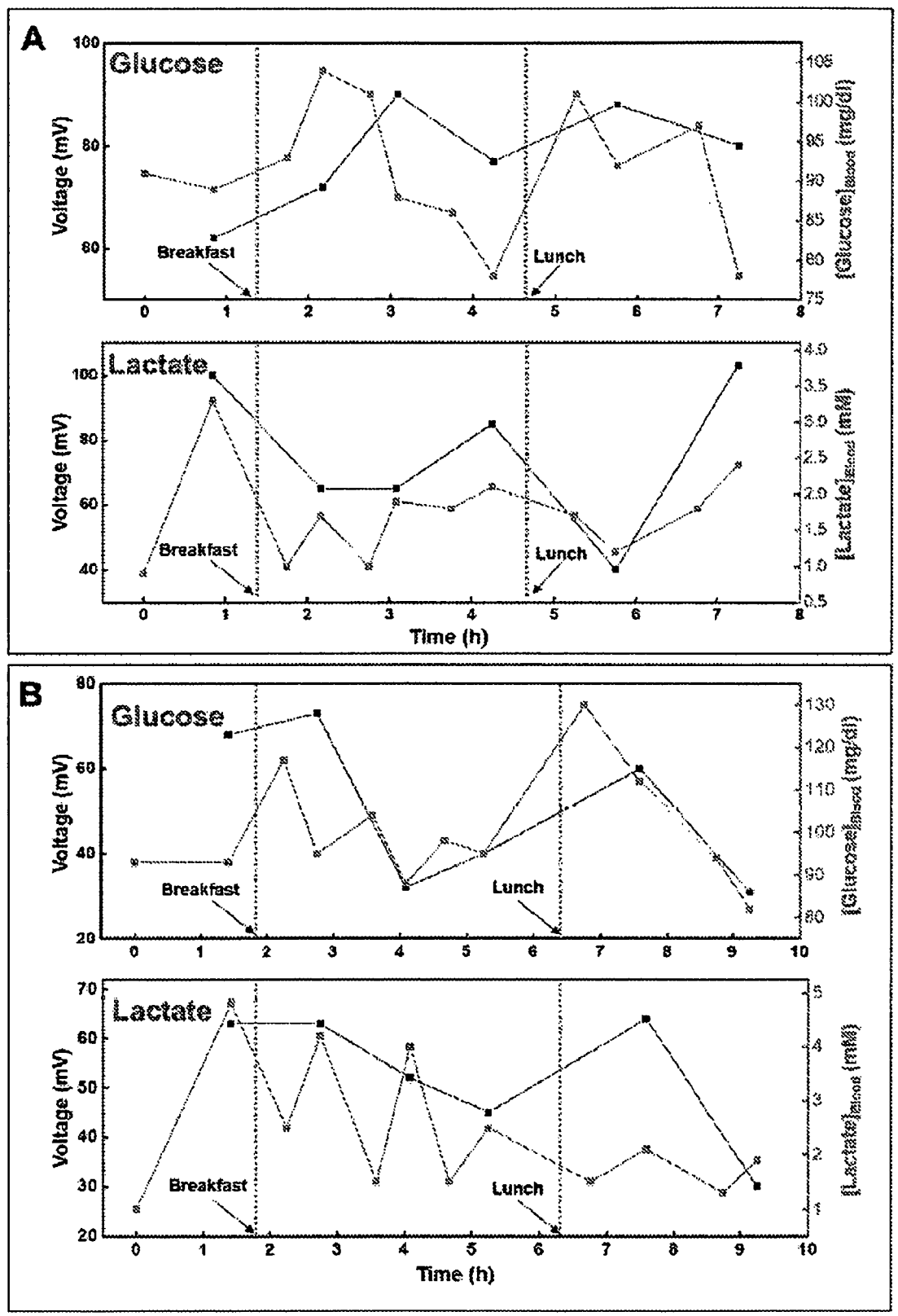

FIG. 48. Correlation of data acquired from biofuel cell-based glucose and lactate sweat sensors with those acquired from blood glucose and lactate meters over a period of one day for (A) subject #1 and (B) subject #2.

Figure 49:
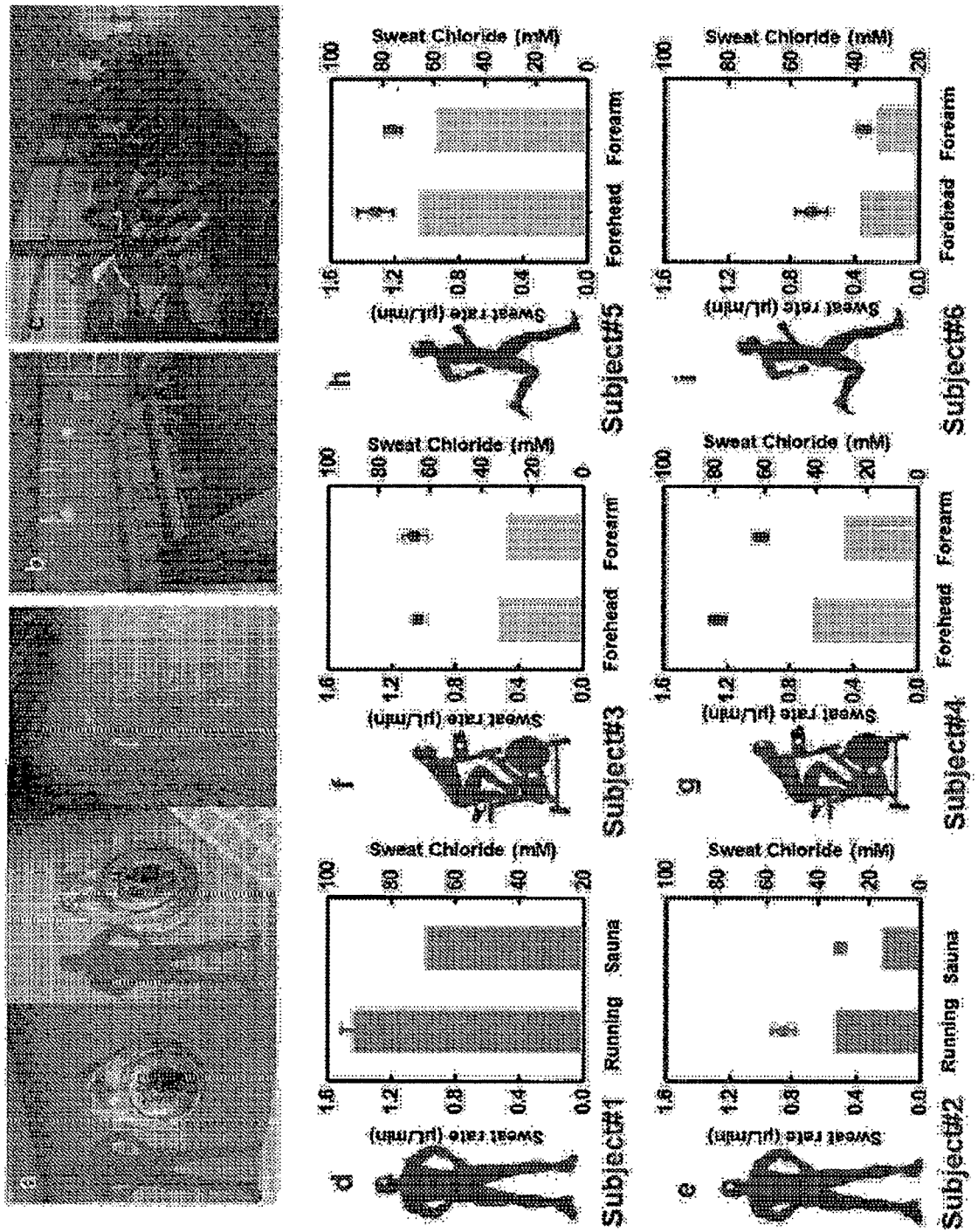

FIG. 49. Human tests. Panel a: Various location on which the device is placed for the human tests. Panel b: The sauna environment for thermal sweat test. Panel c: The gym environment for exercise sweat test. Panels d and e: The comparison of sweat excretion rate and sweat chloride concentration at running and sauna conditions with subject #1 and subject #2. Panels f-i: The comparison of sweat excretion rate and sweat chloride concentration at the device location, placed on forehead and forearm with subject #3, subject #4, subject #5, and subject #6.

Figure 50:
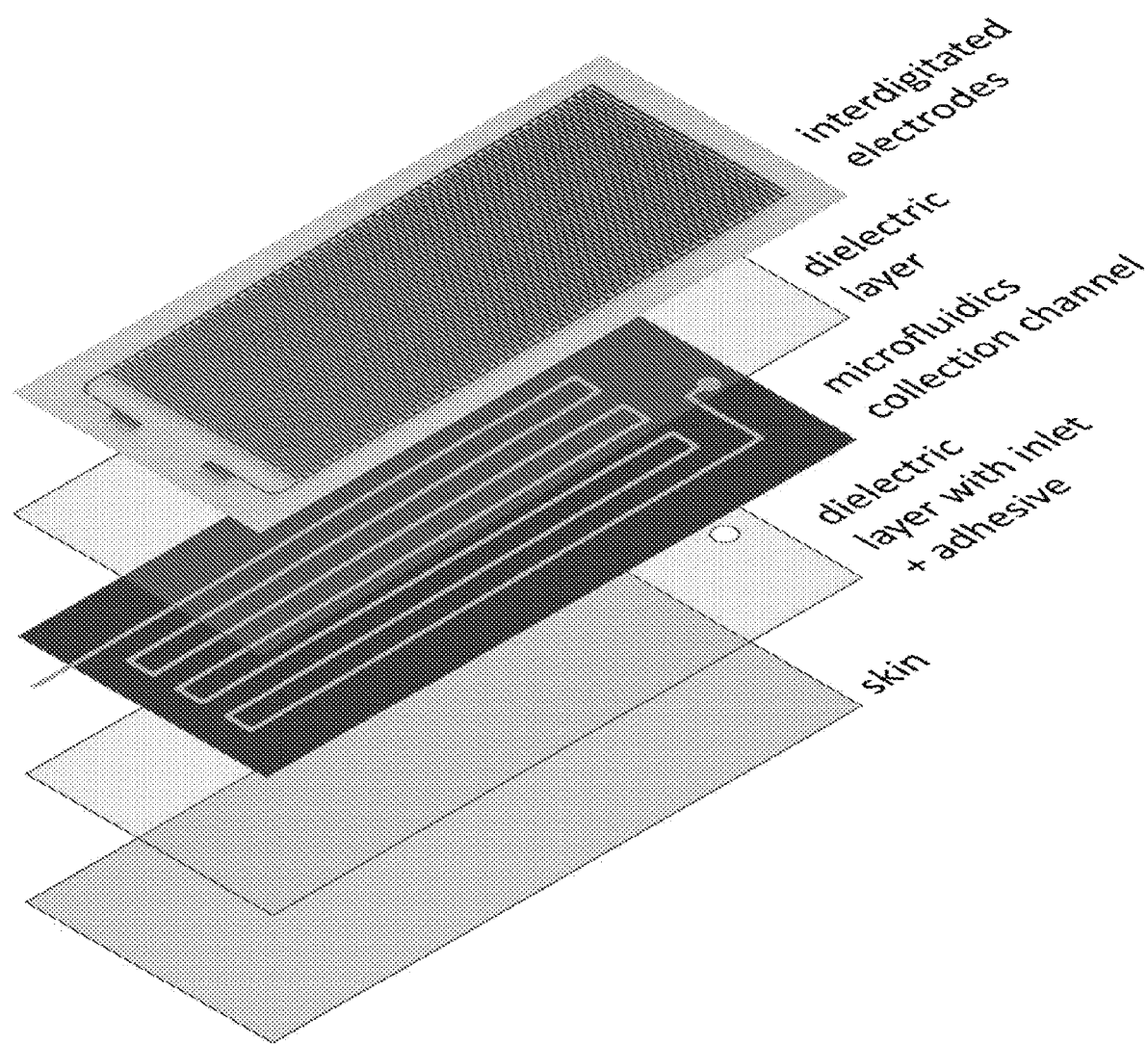

FIG. 50: Exploded illustration of one possible composition of a device involving interdigitated electrodes (technique (i) of Example 15). Interdigitated electrodes would be connected to a NFC or bluetooth capacitance measurement and transmission platform. A frequency sweep could be applied to obtain dielectric spectroscopy data. The electrodes are separated from the microfluidics channel by a thin dielectric layer (thickness below 100 microns). The microfluidics platform can be separated from the skin with a second dielectric layer and adhesive to stick to the skin. An inlet allows filling of the microfluidics platform.

Figure 51:
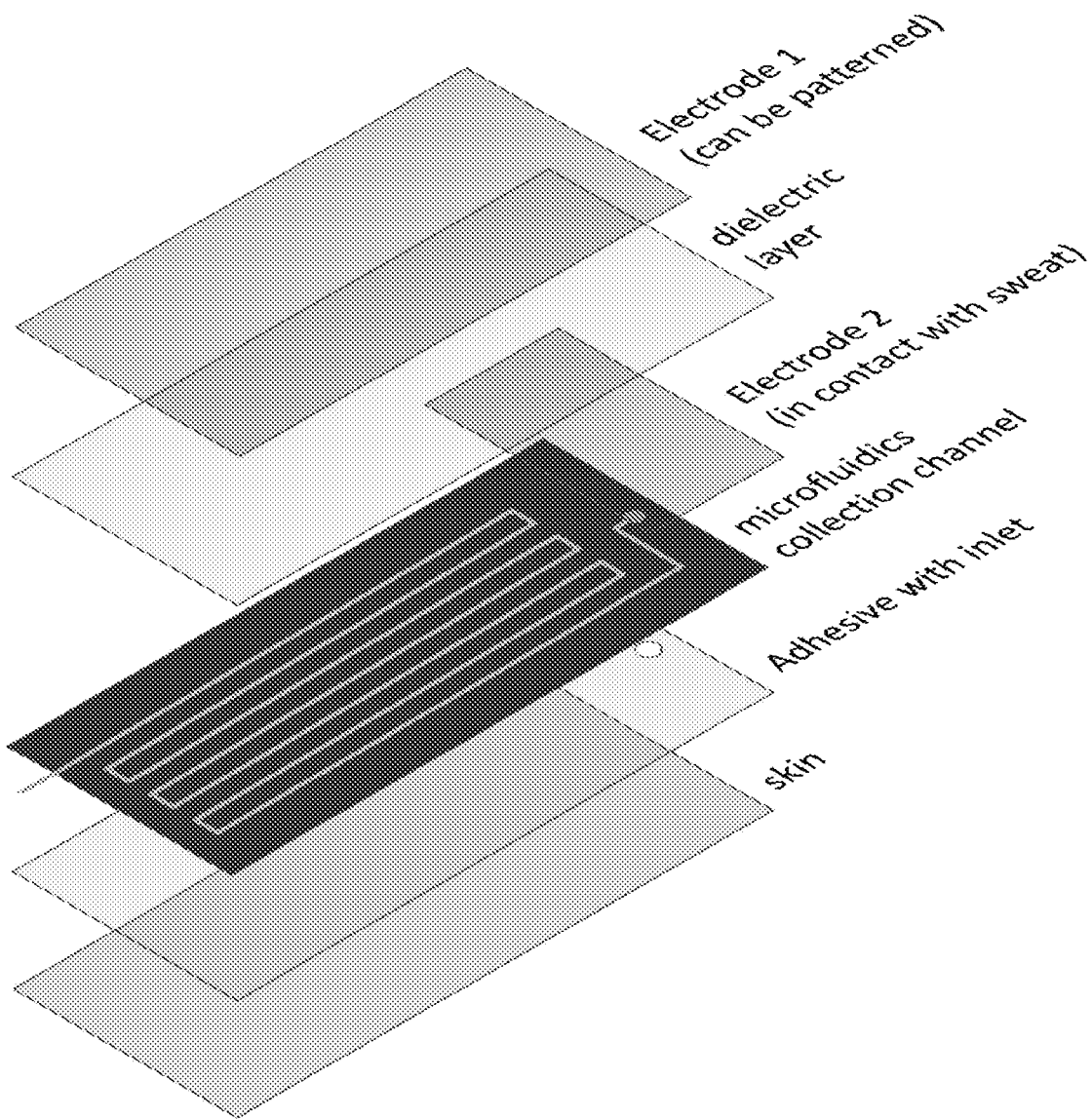

FIG. 51: Exploded illustration of an example of a configuration where sweat could be used as a conductor, to quantify sweat rate, referred to as technique (ii) in Example 15.

Figure 52:
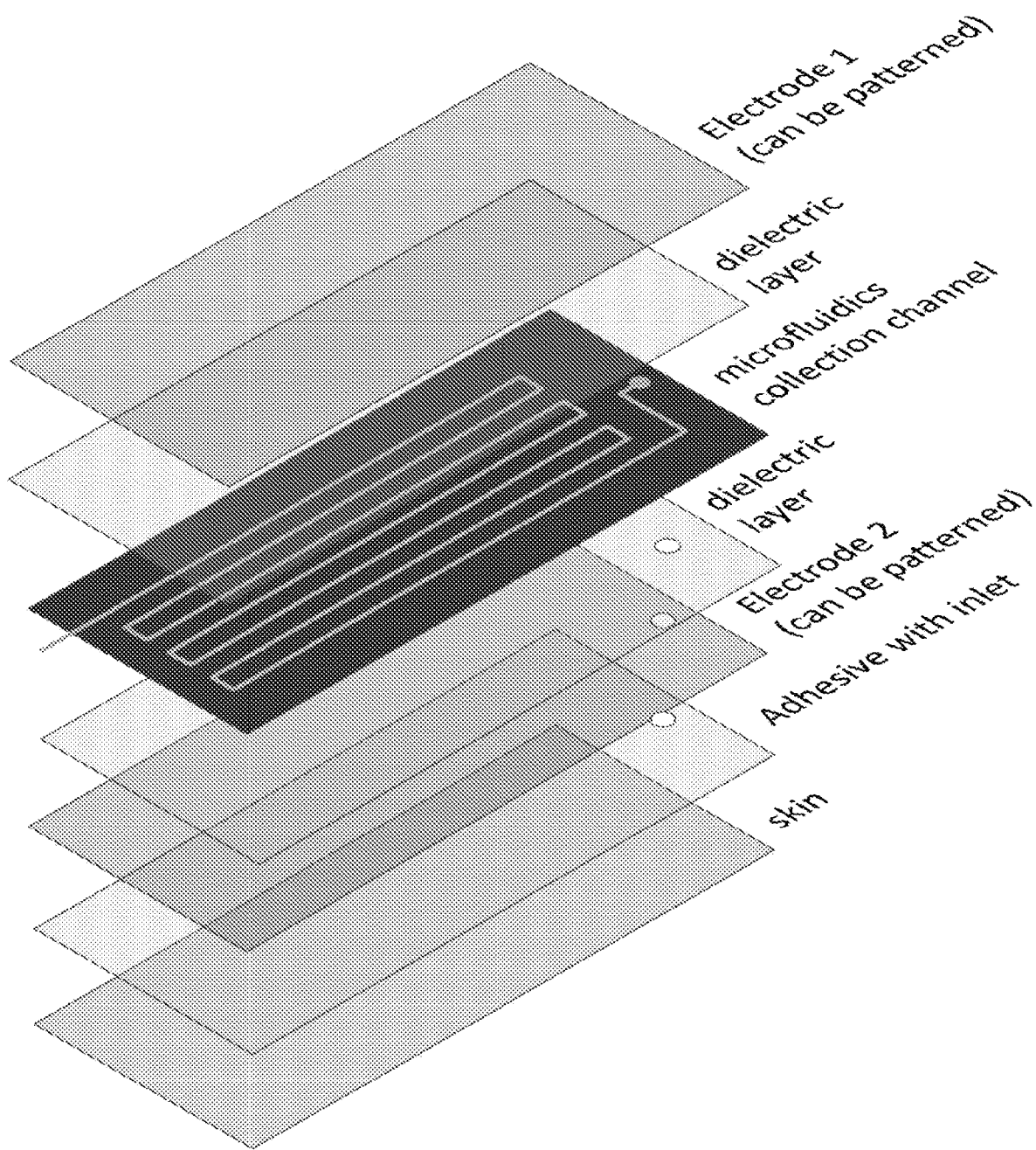

FIG. 52: Exploded illustration of an example of a configuration where two electrodes could be used on top and on the bottom of the microfluidics channels, referred to as technique (iii) in Example 15.

Figure 53:
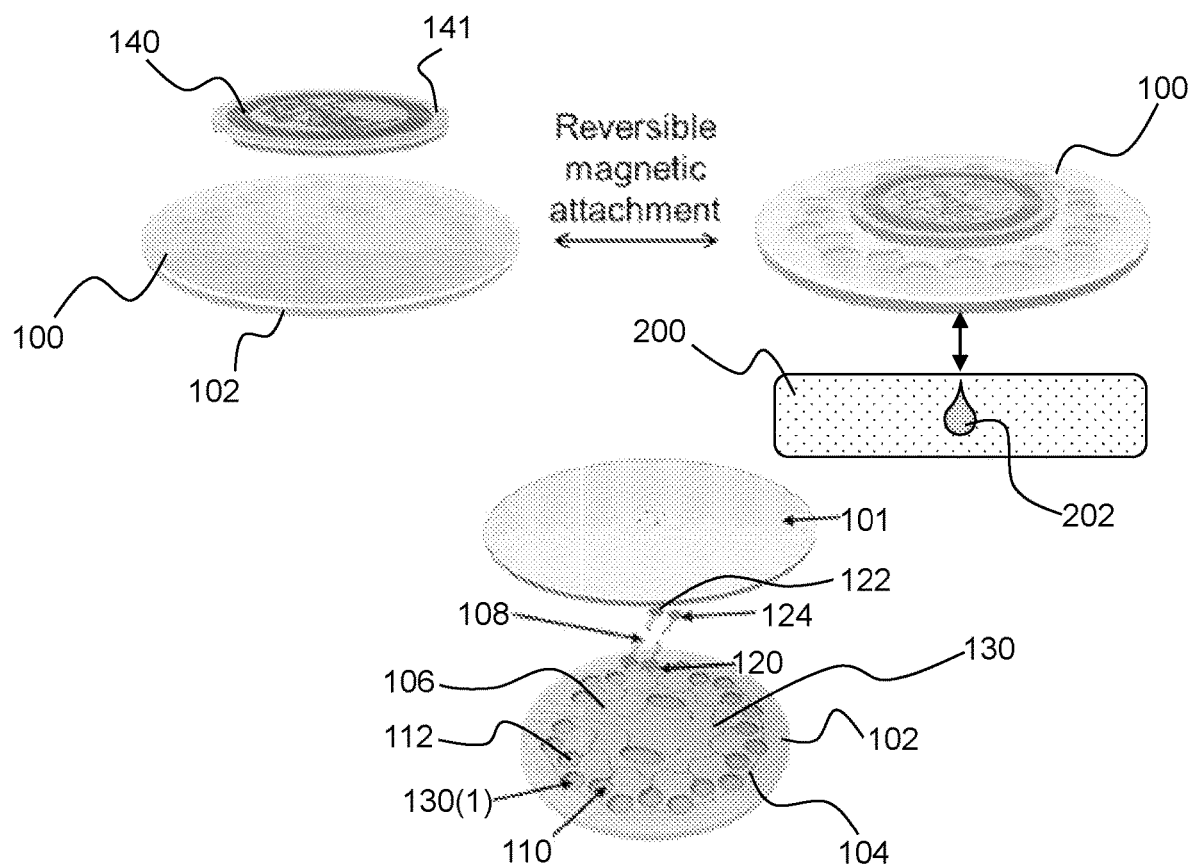

FIG. 53. Schematic of an exemplary microfluidic device in accordance with the present invention.

STATEMENTS REGARDING CHEMICAL COMPOUNDS AND NOMENCLATURE

In general, the terms and phrases used herein have their art-recognized meaning, which can be found by reference to standard texts, journal references and contexts known to those skilled in the art. The following definitions are provided to clarify their specific use in the context of the invention.

"Microfluidic device" refers to a system, device or device component containing liquid constrained in at least one physical dimension generally of the order of nanometers to millimeters, optionally nanometers to microns. Microfluidic devices may include structures for collecting, extracting, transporting, storing, analyzing and/or outputting fluids, including biofluids. In some embodiments, the liquid is constrained to a lateral dimension selected over the range of 1 nm and 1 cm, such as a lateral dimension (e.g., depth) selected over the range of 1 nm to 5 mm, 100 nm to 1000 µm or 500 nm to 100 µm, and a lateral dimension (e.g., width) selected over the range of 1 nm to 1 cm, 10 µm to 2 mm or 1 µm to 10 mm. In embodiments, an axial (e.g., flow) direction in a microfluidic system, device or device component can be long, for example on the order of meters, but will more commonly be 0.1 cm to 100 cm or 1 cm to 50 cm. Microfluidics are distinguished herein from macrofluidics. In some embodiments, the invention provides tissue mounted, optionally skin mounted, microfluidic devices. Microfluidic devices of some embodiments are capable of determining the composition of a biofluid such as sweat, for example, the presence, absence, and/or amount of one or more biomarkers, optionally as a function of time. Microfluidic devices of some embodiments are capable of determining one or more physical parameters characteristics of a biofluid, such as amount, volume, release rate and/or absorption rate, optionally as a function of time.

"Tissue-mounted" refers to systems, devices or device components having at least one surface capable of being supported, directly or indirectly, by a tissue surface, for example in a configuration providing fluidic communication and/or conformal contact. Epidermal systems and devices are a subset of tissue-mounted systems wherein the system, device or device component has at least one surface capable of being supported, directly or indirectly, by a surface of the skin, for example in a configuration providing fluidic communication and/or conformal contact. The invention provides tissue-mounted devices, such as epidermal systems, capable of collection, storage, treatment, processing, handling and/or analysis of biofluids such as sweat.

The expression "at least partially embedded in" refers to a configuration wherein an element, such as a microfluidic network or component thereof, is at least partially, and optionally wholly, integrated on or within a layer and/or device component, such as a substrate. In an embodiment, for example, "at least partially embedded in" refers to a configuration wherein an embedded element, such as a microfluidic element such as an inlet, outlet, passage, channel, and/or reservoir, at least partially comprises one or more surfaces, recessed features, relief features or any combination thereof, within or on a layer or device component it is at least partially embedded in. In an embodiment, for example, "at least partially embedded in" refers to a configuration wherein an embedded element, such as an inlet, outlet, passage, channel, and/or reservoir, at least partially comprises features molded or embossed on or into a layer or device component it is at least partially embedded in. In an embodiment, for example, "at least partially embedded in" refers to a configuration wherein an embedded element, such as an inlet, outlet, passage, channel, and/or reservoir, at least partially comprises features at least partially comprising surfaces (e.g., top, bottom, walls, etc.) of a layer or device component it is at least partially embedded. In an embodiment, for example, "at least partially embedded in" refers to a configuration wherein an embedded element, such as an inlet, outlet, passage, channel, and/or reservoir, is at least partially covered or encapsulated by another device component, such as a top layer or barrier layer.

"Substrate" refers to a device component, such as a layer, having a surface that is capable of supporting, accommodating, embedding or otherwise integrating a structure, including a microfluidic structure, optical structure, electronic structure, thermal structure or any combination of these. Substrates in some embodiments are capable of supporting, accommodating, embedding or otherwise integrating a device component such as microfluidic device component, optical device component, electronic device component, structural device component or any combination of these. In some embodiments, a substrate is capable of at least partially forming an interface with the tissue of a subject, such as with the epidermis or other organ of a subject. In an embodiment, a substrate of the present devices, systems and methods is a biocompatible and/or bioinert material. In an embodiment, a substrate of the present devices, systems and methods is a polymer or elastomer material. Substrates of the invention include "functional substrates" which refers to a substrate component for a device having at least one function or purpose in addition to providing mechanical support for a component(s) disposed on or within the substrate such as a microfluidic functionality, a mechanical functionality, optical functionality or a thermal functionality. In an embodiment, a functional substrate has at least one skin-related function or purpose. In an embodiment, a functional substrate of the present devices and methods exhibits a microfluidic functionality, such as providing transport of a bodily fluid through or within the substrate, for example via spontaneous capillary action or via an active actuation modality (e.g. pump, etc.). In an embodiment, a functional substrate has a mechanical functionality, for example, providing physical and mechanical properties for establishing conformal contact at the interface with a tissue, such as skin. In an embodiment, a functional substrate has a thermal functionality, for example, providing a thermal loading or mass small enough so as to avoid interference with measurement and/or characterization of a physiological parameter, such as the composition and amount of a biological fluid. In an embodiment, a functional substrate of the present devices and method is biocompatible and/or bioinert. A functional substrate may facilitate mechanical, thermal, chemical and/or electrical matching of the functional substrate and the skin of a subject such that the mechanical, thermal, chemical and/or electrical properties of the functional substrate and the skin are within 20%, or 15%, or 10%, or 5% of one another. Devices and systems of the invention may have more than one substrate, for example, such as embodiments having a bottom substrate capable of establishing an interface with skin and an upper substrate layer, such as a barrier layer providing an interface with an ambient environment. For example, the invention includes devices and systems having a multilayer geometry including a substrate and barrier layer.

In some embodiments, a substrate is mechanically matched to a tissue, such as mechanically matched to skin. In an embodiment, a mechanically matched substrate is optionally capable of providing an interface for establishing fluid communication and/or conformal contact with a surface of the tissue, such as skin. Devices and methods of certain embodiments incorporate substrates comprising soft materials, for example exhibiting flexibility and/or stretchability, such as polymeric and/or elastomeric materials. In an embodiment, a mechanically matched substrate has a modulus less than or equal to 100 MPa, and optionally for some embodiments less than or equal to 10 MPa, and optionally for some embodiments, less than or equal to 1 MPa. In an embodiment, a mechanically matched substrate has a thickness less than or equal to 0.5 mm, and optionally for some embodiments, less than or equal to 1 cm, and optionally for some embodiments, less than or equal to 3 mm. In an embodiment, a mechanically matched substrate has a bending stiffness less than or equal to 1 nN m, optionally less than or equal to 0.5 nN m.

In some embodiments, a mechanically matched functional substrate is characterized by one or more mechanical properties and/or physical properties that are within a specified factor of the same parameter for an epidermal layer of the skin, such as a factor of 10 or a factor of 2. In an embodiment, for example, a functional substrate has a Young's Modulus or thickness that is within a factor of 20, or optionally for some applications within a factor of 10, or optionally for some applications within a factor of 2, of a tissue, such as an epidermal layer of the skin, at the interface with a device of the present invention. In an embodiment, a mechanically matched functional substrate may have a mass or modulus that is equal to or lower than that of skin.

In some embodiments, a functional substrate that is thermally matched to skin has a thermal mass small enough that deployment of the device does not result in a thermal load on the tissue, such as skin, or small enough so as not to impact measurement and/or characterization of a physiological parameter, such as a characteristic of a biological fluid (e.g. composition, rate of release, etc.). In some embodiments, for example, a functional substrate that is thermally matched to skin has a thermal mass low enough such that deployment on skin results in an increase in temperature of less than or equal to 2 degrees Celsius, and optionally for some applications less than or equal to 1 degree Celsius, and optionally for some applications less than or equal to 0.5 degree Celsius, and optionally for some applications less than or equal to 0.1 degree Celsius. In some embodiments, for example, a functional substrate that is thermally matched to skin has a thermal mass low enough that it does not significantly disrupt water loss from the skin, such as avoiding a change in water loss by a factor of 1.2 or greater. Therefore, the device does not substantially induce sweating or significantly disrupt transdermal water loss from the skin.

In an embodiment, the functional substrate may be at least partially hydrophilic and/or at least partially hydrophobic.

In an embodiment, the functional substrate may have a modulus less than or equal to 100 MPa, or less than or equal to 50 MPa, or less than or equal to 10 MPa, or less than or equal to 100 kPa, or less than or equal to 80 kPa, or less than or equal to 50 kPa. Further, in some embodiments, the device may have a thickness less than or equal to 5 mm, or less than or equal to 2 mm, or less than or equal to 100 µm, or less than or equal to 50 µm, and a net bending stiffness less than or equal to 1 nN m, or less than or equal to 0.5 nN m, or less than or equal to 0.2 nN m. For example, the device may have a net bending stiffness selected from a range of 0.1 to 1 nN m, or 0.2 to 0.8 nN m, or 0.3 to 0.7 nN m, or 0.4 to 0.6 nN m.

A "component" is used broadly to refer to an individual part of a device.

"Sensing" refers to an action of detecting the presence, absence, amount, magnitude and/or intensity of one or more physical and/or chemical properties or characteristics. Sensor refers to a device or component thereof that is capable of sensing. Useful device components for sensing include, but are not limited to electrode elements, chemical or biological sensor elements, pH sensors, colorimetric sensors, electrochemical sensors, temperature sensors, strain sensors, mechanical sensors, position sensors, optical sensors and capacitive sensors.

"Actuating" refers to stimulating, controlling, or otherwise affecting a structure, material or device component. Actuator refers to a device or component thereof that is capable of actuating. Useful device components for actuating include, but are not limited to, electrode elements, electromagnetic radiation emitting elements, light emitting diodes, lasers, magnetic elements, acoustic elements, piezoelectric elements, chemical elements, biological elements, and heating elements. In the context of communications, actuating may refer to a NFC chip useful in providing communication capability to and/or from the electronics portion of any of the devices provided herein.

The terms "directly and indirectly" describe the actions or physical positions of one component relative to another component. For example, a component that "directly" acts upon or touches another component does so without intervention from an intermediary. Contrarily, a component that "indirectly" acts upon or touches another component does so through an intermediary (e.g., a third component).

"Encapsulate" refers to the orientation of one structure such that it is at least partially, and in some cases completely, surrounded by, or embedded in, one or more other structures, such as a substrate, adhesive layer or encapsulating layer. "Partially encapsulated" refers to the orientation of one structure such that it is partially surrounded by one or more other structures, for example, wherein 30%, or optionally 50%, or optionally 90% of the external surface of the structure is surrounded by one or more structures. "Completely encapsulated" refers to the orientation of one structure such that it is completely surrounded by one or more other structures.

"Dielectric" refers to a non-conducting or insulating material.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are useful for some applications. Polymers useable in the methods, devices and components disclosed include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin, polydimethylsiloxane, polysodiumacrylate or any combinations of these.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. Exemplary elastomers include, but are not limited to silicon containing polymers such as polysiloxanes including poly(dimethyl siloxane) (i.e., PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt a useful contour profile, for example a contour profile allowing for conformal contact with a surface having surface features, e.g., relief or recessed features. In certain embodiments, a desired contour profile is that of skin.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface.

"Young's modulus" is a mechanical property of a material, device or layer which refers to the ratio of stress to strain for a given substance. Young's modulus may be provided by the expression:

$$E = \frac{(\text{stress})}{(\text{strainn})} = \left(\frac{L_0}{\Delta L}\right)\left(\frac{F}{A}\right), \tag{I}$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \tag{II}$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100

MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components having a low Young's modulus. In an embodiment, a device of the invention has an overall low Young's modulus.

"Low modulus" refers to materials having a Young's modulus less than or equal to 10 MPa, less than or equal to 5 MPa or less than or equal to 1 MPa. In some embodiments, the functional substrate is a low modulus material, such as a low modulus elastomer.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

The terms "flexible" and "bendable" are used synonymously in the present description and refer to the ability of a material, structure, device or device component to be deformed into a curved or bent shape without undergoing a transformation that introduces significant strain, such as strain characterizing the failure point of a material, structure, device or device component. In an exemplary embodiment, a flexible material, structure, device or device component may be deformed into a curved shape without introducing strain larger than or equal to 5%, for some applications larger than or equal to 1%, and for yet other applications larger than or equal to 0.5% in strain-sensitive regions. A used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 10000 microns, optionally less than 1000 microns and optionally less than 100 micron) and device geometries such as thin film and mesh geometries.

"Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. A used herein, stretchable structures may also be flexible. Some stretchable structures (e.g., device components) are engineered to be able to undergo compression, elongation and/or twisting so as to be able to deform (and optionally operate) without fracturing. Stretchable structures include structures comprising stretchable materials, such as elastomers; and bent, coiled or serpentine structures capable of elongation, compression and/or twisting motion.

Devices of the present invention may optionally include one or more barrier layers. As used herein "barrier layer" refers to a device component spatially separating two or more other device components or spatially separating a device component from a structure, material, fluid or ambient environment external to the device. In one embodiment, a barrier layer encapsulates one or more device components. In embodiments, a barrier layer separates one or more device components from an aqueous solution, a biological tissue and/or a biological environment. In some embodiments, a barrier layer is a passive device component. In some embodiments, a barrier layer is a functional, but non-active, device component. In a specific embodiment, a barrier layer is a moisture barrier. As used herein, the term "moisture barrier" refers to a barrier layer which provides protection to other device components from bodily fluids, ionic solutions, water or other solvents. In one embodiment, a moisture barrier provides protection to an external structure, material or fluid, for example, by preventing leakage current from escaping an encapsulated device component and reaching the external structure, material or fluid.

"Biofluid" refers to fluid generated by, extracted from or otherwise derived from the tissue of a subject, such as an organ of a subject. Biofluids include sweat, tears, saliva, gingival crevicular fluid, interstitial fluid, blood and combinations thereof.

As used herein, the term "fluidically connected" refers to the configuration of two or more components such that a fluid (e.g., a gas or a liquid) is capable of transport, flowing and/or diffusing from one component to another component, without adversely impacting the functionality of each of the components. Components may be in fluid communication with each other via one or more intervening elements such as channels, valves, tubes, containment structures, reservoirs, pumps or any combinations of these. Components in fluid communication may be in direct fluid communication wherein fluid is capable of moving directly from one component to another. Components in fluid communication with each other may be in indirect fluid communication wherein fluid is capable of transport indirectly from one component to another via one or more intervening structures that physically separate the components. The phrases "fluidically connected to", "in fluid communication with", and "in fluidic communication with" may be used interchangeably.

The term "operably connected" refers to a configuration of elements, wherein an action or reaction of one element affects another element, but in a manner that preserves each element's functionality. In an illustrative example, an electrochemical sensor operably connected to an electronic device providing for wireless power harvesting refers to the ability of the electrochemical sensor to be connected to the electronic device in such a way as to receive wireless power without adversely impacting the functionality of the electrochemical sensor and the electronic device. In another illustrative example, a sensor (e.g., capacitive sensor) operably connected to a microfluidic network refers to the sensor's ability to sense one or more parameters of a biofluid, or component thereof, which is being transported by the microfluidic network, without adversely impacting the functionality of the sensor or of the microfluidic network. The connection may be by a direct physical contact between elements. The connection may be indirect, with another element that indirectly connects the operably connected elements. For example, a capacitive sensor may be indirectly connected to the microfluidic network, with a dielectric layer physically separating the sensor and the microfluidic network, for example.

The terms "electrical contact" and "electronic contact" refers to the ability of two or more materials and/or structures that are capable of transferring charge between them, such as in the form of the transfer of electrons or ions. The terms "electrical contact" and "electronic contact" may refer to a configuration of two or more components such that an electronic signal or charge carrier can be directly or indirectly transferred from one component to another. As used herein, the terms "electrical contact" and "electronic contact" include one way and two way electrical communication. In some embodiments, components in electrical contact or electronic contact are in indirect electrical communication wherein an electronic signal or charge carrier is indirectly transferred from one component to another via one or more intermediate structures, such as circuit elements, separating the components.

As used herein, the term "electrical load" may refer to voltage or current applied to electrodes, sensors or other device components. The term "electrical response" or "electrical parameter" may refer to a voltage, current, or impedance response of the electrodes or sensors to the electrical load. For example, applying a current between two electrodes (electrical load) may induce a voltage drop between the two electrodes (electrical response). The electrical load may be a DC or an AC load.

The term "BLE" refers to a Bluetooth low energy system.

The term "functionalized" may refer to modification of a material or layer surface to add chemical, physical, electrical, optical or electrochemical functionality. In an embodiment, biological molecules or reagents may be deposited onto an electrode in a process of forming an electrochemical sensor.

The term "wet environment" may refer to the system being in a high-humidity environment or being at least partially surrounded by a liquid. The term "high-humidity" refers to the relative humidity of the surroundings being >70%.

DETAILED DESCRIPTION OF THE INVENTION

In the following description, numerous specific details of the devices, device components and methods of the present invention are set forth in order to provide a thorough explanation of the precise nature of the invention. It will be apparent, however, to those of skill in the art that the invention can be practiced without these specific details.

Figure 6:
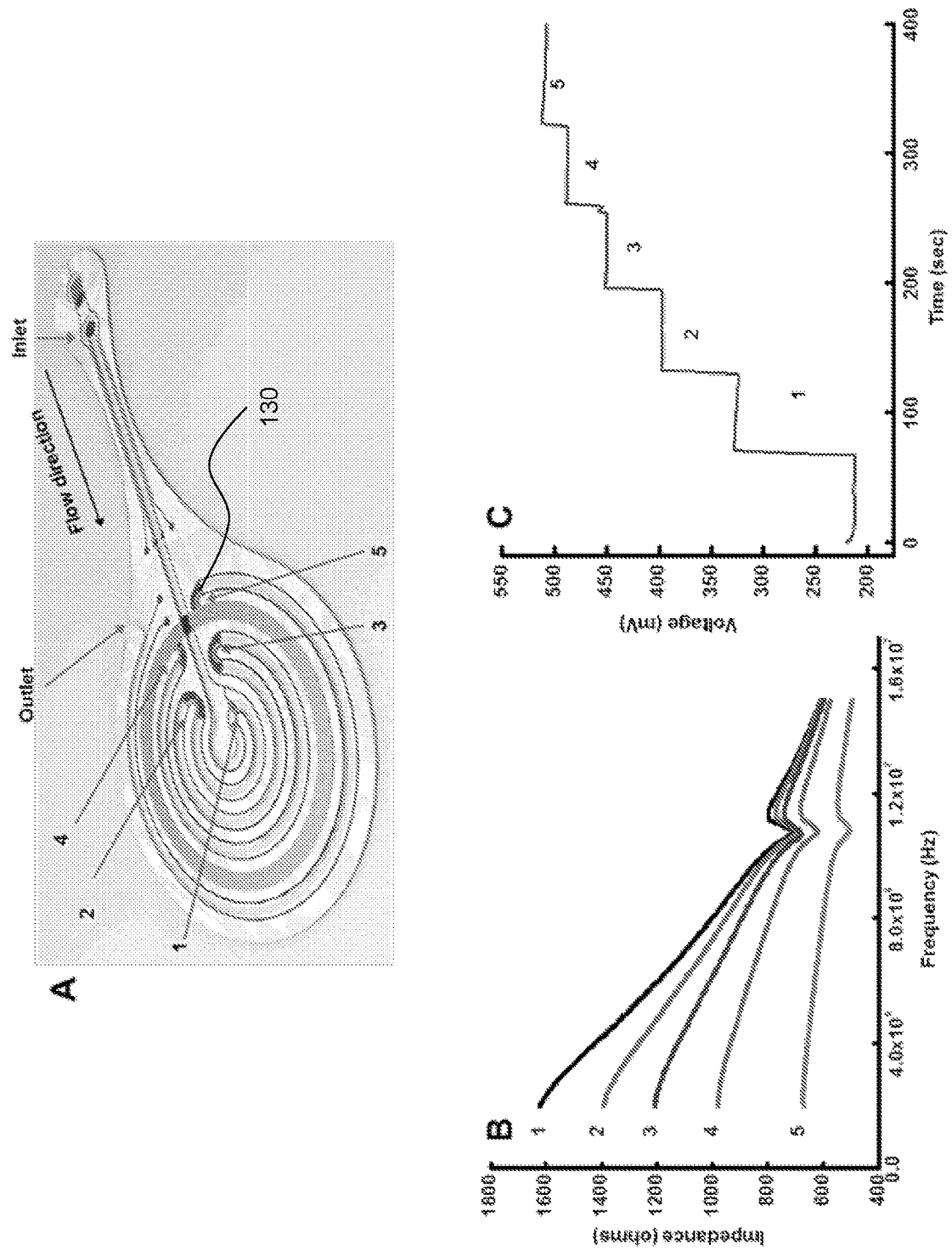
FIG. 6. Panel A is a schematic of an example battery-free NFC-based sweat rate sensor. Panel B is a plot of impedance spectra (impedance vs. frequency) obtained from the device with increasing levels of filling of the channel with buffer. Panel C is a plot showing voltage (mV) vs. time (seconds) data from wireless NFC electronics for the device with increasing levels of filling of the channel with buffer. Data in Panels B and C was recorded when the channel was filled with buffer up to specific points as illustrated in Panel A.

FIG. 53 are schematics of microfluidic device 100, an exemplary microfluidic device in accordance with the present invention. Microfluidic device 100 may be mounted onto a skin surface 200 of a subject, such as a human subject. Microfluidic device 100 comprises a flexible substrate 102 and a microfluidic network 104. Microfluidic network 104 is at least partially embedded in or supported by substrate 102. A biofluid inlet 106 is fluidically connected to microfluidic network 104 to transport a biofluid 202 from skin surface 200 to microfluidic network 104. It will be understood from the description herein that microfluidic devices of the present invention may include one or more sensors supported by the flexible substrate. Microfluidic system 100 comprises an optical sensor 110, an electrochemical sensor 120, an electronic sensor 130, and an electronic device 140, each of which is independently supported by substrate 102. Optical sensor 110 may be, but is not limited to, a colorimetric sensor. Optical sensor 110 comprises one or more integrated optical structures 112. Electrochemical sensor 120 comprises a cathode 122 and an anode 124. Another example of electronic sensor 130 is also depicted in FIG. 6. Electronic device 140 may be or may comprise, for example, an NFC and/or Bluetooth electronics module. Microfluidic system 100 may comprise a cover 101. Microfluidic system 100 may comprise one or more coupling elements 108, such as magnetic elements.

The invention can be further understood by the following non-limiting examples.

Example 1: Battery-free Near-field Communication-based Soft, Wearable Microfluidic Sweat Sensors Real-time monitoring of sweat rate and physiologically relevant sweat constituents can provide valuable information about a person's well-being and fitness level. Absorbent pads may be attached to the skin for collecting sweat followed by off-site analysis at centralized laboratories to estimate concentration levels of the chemical constituents. Unfortunately, the latter approach may fail to provide the necessary transient concentration profiles. Challenges include a time lag between sweat collection and analysis that can lead to degradation of a sample and thus result in inaccurate tests. There have been a handful of demonstrations of wearable chemical sensors for sweat analysis to address this issue, but those are fundamentally deficient in that they require bulky electronics that cannot be easily mated with the soft, stretchable human epidermis. Additionally, those can detect only certain metabolites and electrolytes in the sweat. The present example, in contrast, pertains to a soft, stretchable multi-parameter sweat sensor for monitoring sweat rate and sweat constituents, such as, metabolites, electrolytes, vitamins, amino acids, drugs and proteins. In certain embodiments, each device has a unique code for accurately logging the sensor data for a user thus enabling easy data mining. The device may be realized by combining microfluidics, wireless electronics, electrochemical and/or colorimetric sensors, and are useful for a range of applications, including real-time analysis of sweat constituents; sweat rate monitor; and skin temperature sensor.

Advantages of the present devices, systems and methods include: soft, conformal device; battery-free sensing of metabolites, vitamins, amino acids, drugs and proteins; and single platform combining colorimetric and electrochemical sensors.

The devices and methods provided herein pertain to the development of a soft, skin-like wearable battery-free multi-parameter sweat sensor for real-time, simultaneous monitoring of sweat chemical constituents and/or sweat rate. Each sensor may have a unique code for accurately logging the sensor data for a user thus enabling easy data mining.

Figure 1:
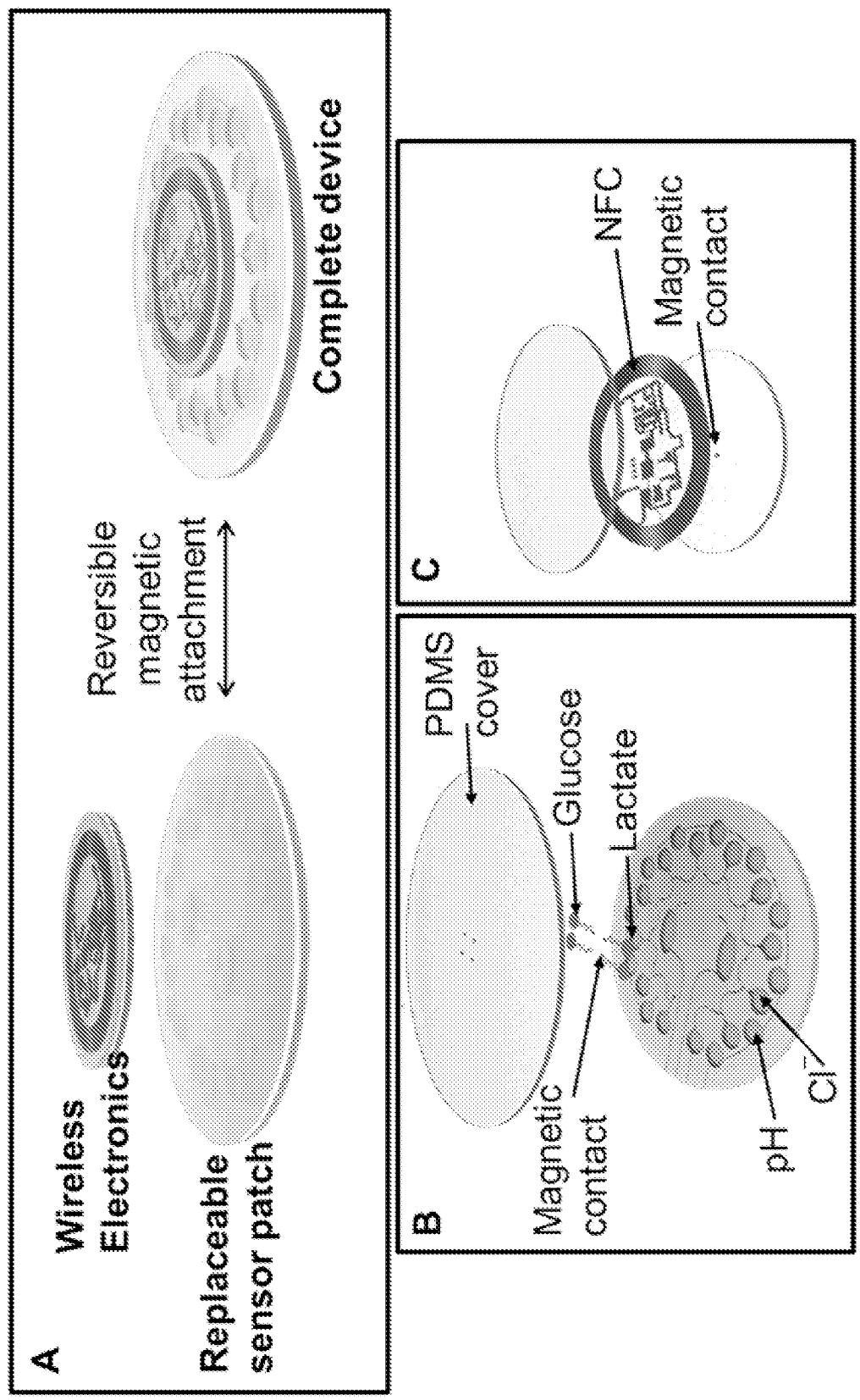
FIG. 1. Panel A is a schematic representation of an example battery-free multi-analyte sweat sensing device. The example of panel A illustrates that the electronic device ("wireless electronics") may be reversibly affixed to the microfluidic system via, for example, magnets. Panel B is an exploded view illustration of the components of an exemplary replaceable microfluidic system having microfluidic features, sensors, and electrodes for detecting the pH, chloride concentration, glucose concentrations, and lactate concentrations. Panel C is an exploded view illustration of the components of a reusable wireless battery-free electronic device that employs NFC electronics.

Thin, Soft Microfluidic Battery-free Devices for Sweat Rate and Chemical Sensing and User Identification: FIG. 1 is a schematic representation of (panel A) of an example battery-free multi-analyte sweat sensing device. The example in FIG. 1 panel A illustrates that the electronic device ("wireless electronics") may be reversibly affixed to the microfluidic system via, for example, magnets. FIG. 1 panel B is an exploded view illustration of the components of an exemplary replaceable microfluidic system having microfluidic features, sensors, and electrodes for detecting the pH, chloride concentration, glucose concentrations, and lactate concentrations. FIG. 1 panel C is an exploded view illustration of the components of a reusable wireless battery-free electronic device that employs NFC electronics.

Figure 2:
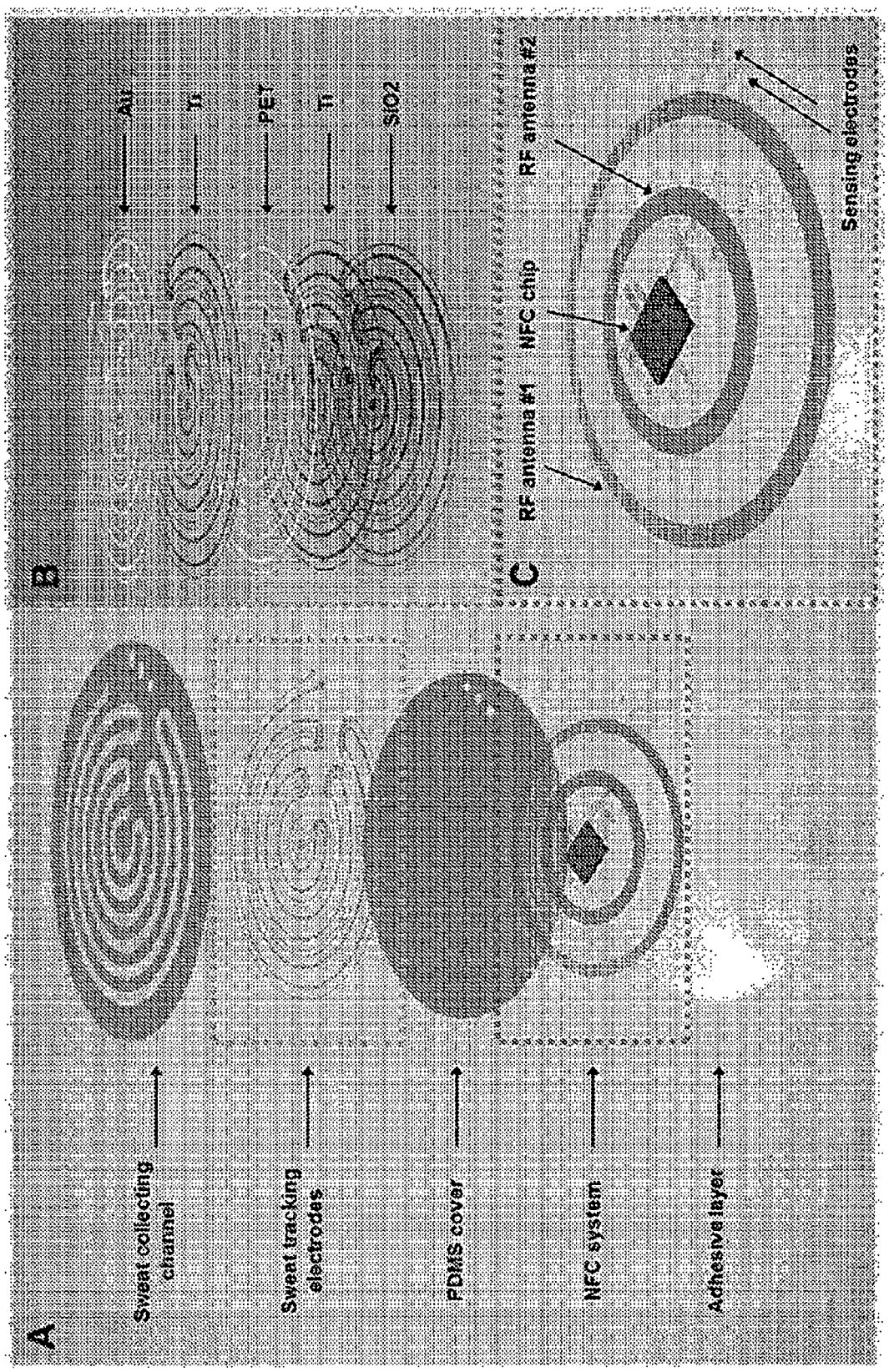
FIG. 2. Panel A illustrates an exploded view of certain components of a battery-free NFC-based sweat rate (biofluid) sensor, including the substrate having a sweat collecting channel, the sweat tracking electrodes, a cover layer, an electronic device having NFC electronics, and an adhesive layer. Panel B is an exploded view of example layers of the sweat tracking electrodes. Panel C illustrates exemplary components of the electronic device with NFC wireless electronics.

FIG. 2 (panel A) illustrates an exploded view of certain components of a battery-free NFC-based sweat rate (biofluid) sensor, including the substrate having a sweat collecting channel, the sweat tracking electrodes, a cover layer, an electronic device having NFC electronics, and an adhesive layer. FIG. 2 (panel B) is an exploded view of example layers of the sweat tracking electrodes. FIG. 2 (panel C) illustrates exemplary components of the electronic device with NFC wireless electronics.

Figure 3:
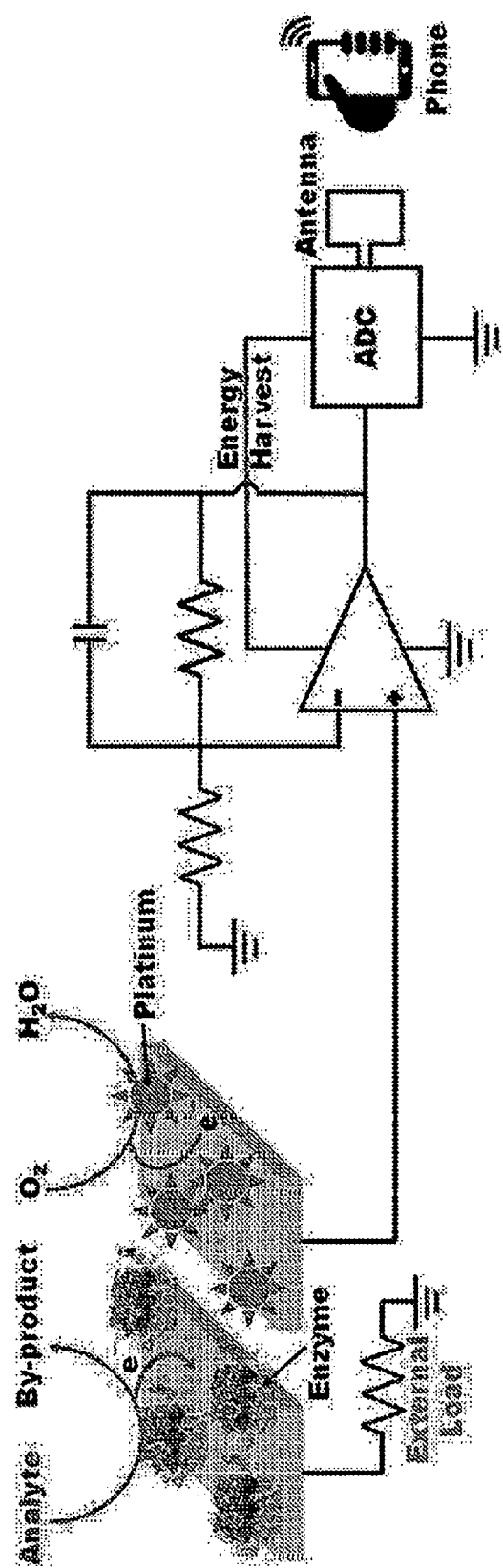
FIG. 3 illustrates exemplary features of an electrochemical sensor and electronic device. The electrochemical sensor has a functionalized anode and a cathode. The electronics of the electronic device, in combination with a remotely held controller, such as a mobile phone, detects an electrical output from the sensor that is proportional to a biofluid property, such as analyte concentration.

FIG. 3 illustrates exemplary features of an electrochemical sensor and electronic device. The electrochemical sensor has a functionalized anode and a cathode. The electronics of the electronic device, in combination with a remotely held controller, such as a mobile phone, apply an electrical load to the electrochemical sensor and detects an electrical output from the sensor that is proportional to a biofluid property, such as analyte concentration.

Figure 4:
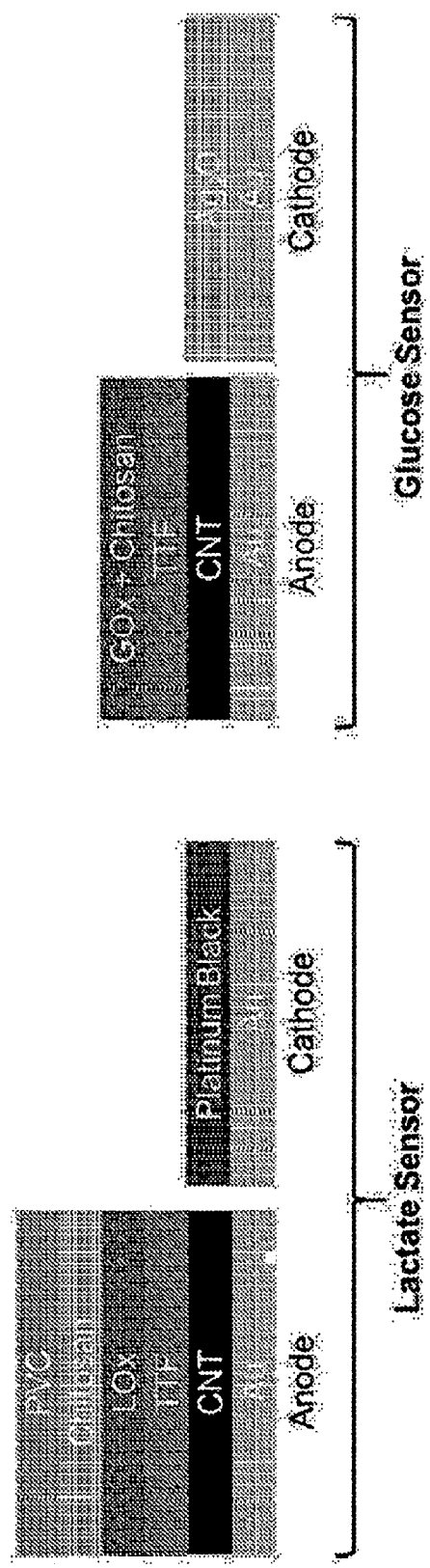
FIG. 4 Illustrates certain layers of the anode and cathode of an electrochemical sensor for detecting lactate (left) and for detecting glucose (right).

FIG. 4 Illustrates certain layers of the anode and cathode of an electrochemical sensor for detecting lactate (left) and for detecting glucose (right).

Figure 5:
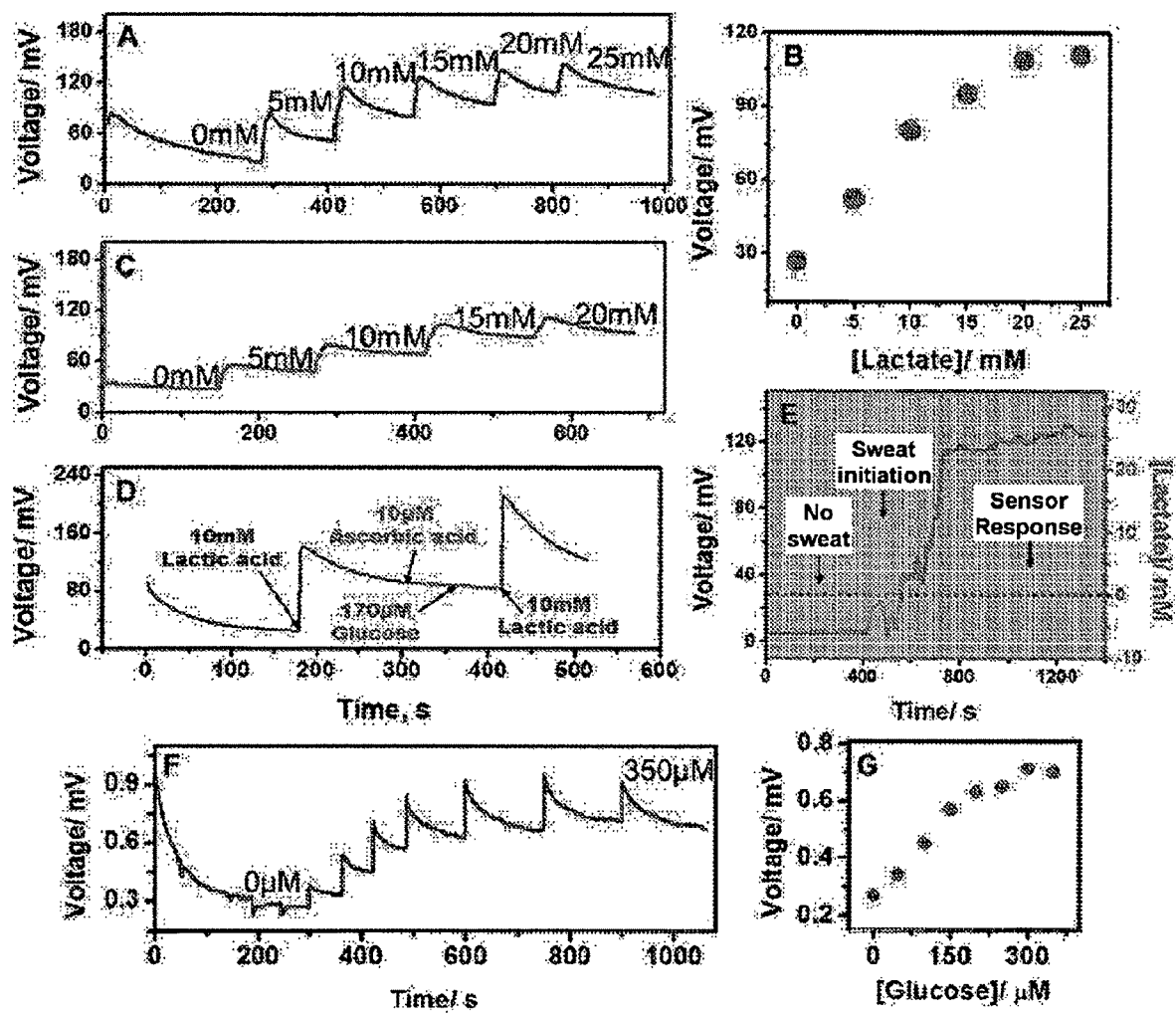
FIG. 5 shows data for: (Panel A) voltage (mV) vs. time (seconds) corresponding to real-time sensor response to increasing lactate concentration at T=25° C.; (Panel B) voltage (mV) vs. lactate concentration (mM) corresponding to calibration plot for lactate sensor at T=25° C.; (Panel C) voltage (mV) vs. time (seconds) corresponding to real-time sensor response to increasing lactate concentration at T=37° C.; (Panel D) voltage (mV) vs. time (seconds) corresponding to effect of common interferrents on lactate sensor; (Panel E) voltage (mV) vs. time (seconds) and lactate concentration (mM) vs. time (s) corresponding to real-time monitoring of sweat lactate obtained from a perspiring human subject; (Panel F) voltage (mV) vs. time (seconds) corresponding to real-time sensor response to increasing glucose concentration at T=25° C., and (Panel G) voltage (mV) vs. glucose concentration (µM) corresponding to calibration plot for glucose sensor at T=25° C.

FIG. 5 shows data for: (Panel A) Real-time sensor response to increasing lactate concentration at T=25° C.; (Panel B) Calibration plot for lactate sensor at T=25° C.; (Panel C) Real-time sensor response to increasing lactate concentration at T=37° C.; (Panel D) Effect of common interferrents on lactate sensor; (Panel E) Real-time monitoring of sweat lactate obtained from a perspiring human subject; (Panel F) Real-time sensor response to increasing glucose concentration at T=25° C.; and (Panel G) Calibration plot for glucose sensor at T=25° C.

FIG. 6 shows: (Panel A) Schematic of an example battery-free NFC-based sweat rate sensor; (Panel B) Impedance spectra obtained from the device with increasing levels of filling of the channel with buffer; and (C) Data from wireless NFC electronics for the device with increasing levels of filling of the channel with buffer. (Panels B,C) data was recorded when the channel was filled with buffer up to specific points as illustrated in (Panel A)

A schematic representing certain embodiments is shown in FIG. 1, panel A. The example device comprises an example disposable microfluidic system (FIG. 1, panel B) and an example reusable wireless electronic board (FIG. 1, panel C). The soft microfluidic system has inlets, outlets, channels and chambers for separate and concurrent detection of desired chemical analytes present in a biofluid such as sweat. The electrodes for electrochemical sensing as well as reagents for colorimetric sensing may be embedded within the microfluidic system. The sensing modality employed for detecting a particular analyte may depend on the ease of its integration with the wearable platform, accuracy, detection range and stability. For example, colorimetric assays may be exploited for detecting certain analytes and parameters of interest, including but not limited to, sweat pH, chloride and electrochemical transducers for monitoring others, such as but not limited to, lactate and glucose. The contact pads of the electrodes and that of the wireless electronic board may have conductive permanent magnets, such as, but not limited to NdFeB for reversible attachment between the two. Chrono-colorimetric detection of analytes may be achieved by relying on capillary burst valve features within the microfluidic channels for time sequential filling of chambers with colorimetric assays. The sequential microfluidic architecture may also be exploited for electrochemical sensing. The sequential filling of the chambers may also serve as a sweat rate sensor. A dedicated battery-free sweat rate sensor may be integrated within the microfluidic system. FIG. 2 illustrates an example of a battery-free sweat rate sensor.

Near-field communication (NFC) technology and dedicated smartphone Apps may be employed for battery-free electrochemical detection of chemical analytes while concentration data generated by colorimetric assays may be captured via a smartphone camera. Thus, in certain embodiments, the user may only need a smartphone to obtain data from the electrochemical and colorimetric sensors present within the sensor patch. Each electronic system may possess a unique code for differentiating a particular user from others. Thus, data recorded for each individual may be easily mined for personalized health and fitness analysis. In certain embodiments, Bluetooth Low Energy (BLE) protocol may be used for continuous, autonomous data acquisition. Electronics and the microfluidic systems may also be combined into a single component device. The device fabrication may be easily scalable for mass production with commercially established techniques, such as, but not limited to roll-to-roll lamination with die or laser cut capability and injection molding with lamination.

Chemical sensors: Electrochemical sensors are successful forms of chemical sensors due to their accuracy, precision, ease of use, ability to be miniaturized and cost-effectiveness. The electronics required by conventional amperometric, voltammetric and impedimetric electrochemical sensors are quite bulky and transforming it into a soft, stretchable, battery-free version is challenging. In order to address this issue, new sensing principles are exploited herein. Battery-free NFC-based potentiometric sensors for voltage measurement may require minimal electronic components, thus allowing miniaturization. Conventional potentiometric sensors exist only for a limited selection of analytes. Therefore, non-conventional wearable sensing platforms are disclosed herein for the detection of other relevant sweat analytes, such as, metabolites, proteins, amino acids, drugs, vitamins wherein the sensor may generate a voltage signal proportional to the analyte concentration. The present disclosure exploits an electrochemical sensor and an electronic device, such as a biofuel cell setup, to achieve this, for example. The current generated by the electrochemical sensor (e.g., biofuel cell) may be directly proportional to the analyte concentration. Thus, by applying an external load, the voltage drop across the electrochemical sensor is proportional to the analyte concentration. A schematic illustrating an exemplary electrochemical (e.g., biofuel cell) based battery-free sensor is shown in FIG. 3.

An electrochemical (e.g., biofuel cell) based battery-free electrochemical sensing of lactate and glucose is described. Each sensor may comprise an anode and a cathode (FIG. 4). A carbon nanotube buckypaper or carbon fiber paper coated with carbon nanotubes may be first bonded to the anode to increase its net surface area. Thereafter, the anode may be functionalized with tetrathiafulvalene (redox mediator) and enzyme (lactate oxidase or glucose oxidase). Protective biocompatible polymeric membranes of chitosan and polyvinyl chloride may be coated over the electrode for obviating leaching and for increasing the detection range. The cathode may be realized by incorporating oxygen reducing catalysts, such as platinum black, platinum on carbon, ruthenium, manganese oxide, iodine or silver oxide.

Data comprising sensor calibration at 25° C. and 37° C., interference study and real-time on-body measurement of sweat lactate is performed as illustrated in FIG. 5.

The constituents of the sensors are not limited to the above reagents and other mediators, such as, methylene blue, ferrocene, and naphthoquinone, enzymes, such as, pyruvate oxidase, amino acid oxidase, and urease, and polymers, such as, polyols, acrylates, silicones, and urethanes may be included for developing sensors for other analytes. Similarly, affinity based receptors, such as, antibodies, aptamers, DNA (polynucleotides) can also be included to develop anodes that detect specific analytes. Cathodes may be used that incorporate enzymes, such as, bilirubin oxidase, laccase, non-precious oxygen reducing catalysts, manganese oxides, etc.

Sweat rate sensors: A battery-free NFC-based sweat rate sensor (FIG. 6, panel A) may work on the principle of impedance variation due to presence of sweat. The sensor may comprise a long meandering microfluidic channel with a pair of electrodes running parallel within it. The electrodes may be connected to a NFC-based electronic system that may measure impedance variation between the two electrodes. The dielectric constant of the electrodes' surrounding changes when the sweat enters the channel and covers the electrodes. The deviation of the impedance depends on the area of the electrodes submerged under the sweat. Thus, by monitoring the variation in the impedance, one may determine or estimate the sweat rate. FIG. 6, panel B illustrates impedance spectra for increasing levels of filling of a channel with buffer measured using an impedance analyzer highlighting the viability of this device to measure sweat rate. The microfluidic system may be connected to a NFC electronic device that measures voltage as a function of the impedance across the two electrodes, thus allowing battery-free monitoring of sweat rate. FIG. 6, panel C demonstrates data acquired from a NFC electronic device for increasing levels of channel filling.

Additional Examples: Provided herein are representative examples of various systems and methods. For example, Example 1a is directed to a microfluidic patch and associated electronics and electrochemical sensors:

Example 1a. A microfluidic system for monitoring a biofluid, comprising: a flexible substrate; a microfluidic network at least partially embedded in or supported by the substrate; an electrochemical sensor supported by the substrate and fluidically connected to the microfluidic network; a biofluid inlet fluidically connected to the microfluidic network to transport a biofluid from a skin surface, during use, to the electrochemical sensor; and an electronic device in electronic contact with the electrochemical sensor to detect an electronic output from the electrochemical sensor.

The systems may be described in terms of the relationship of electrochemical sensor and the associated electronic device, including as outlined below in Examples 2a-5a:

2a. The microfluidic system of example 1, wherein the electronic device is configured to apply an electrical load to the electrochemical sensor to generate an electrical output from the electrochemical sensor that is proportional to a biofluid property.

3a. The microfluidic system of example 2a, wherein the electrical output is a voltage change.

4a. The microfluidic system of examples 2a or 3a, wherein the biofluid property is selected from the group consisting of biofluid volume, a biofluid analyte concentration or amount, temperature, and any combination thereof.

5a. The microfluidic system of example 4, wherein the microfluidic system measures the biofluid property as a function of time.

The systems may be described in terms of the structure of the electrochemical sensors, including as outlined below in Examples 6a-13a:

6a. The microfluidic system of any of examples 1a-5a, wherein the electrochemical sensor comprises: an anode having an anode conductive layer; an anode reactive layer supported by the anode conductive layer; and a cathode, having a reductant or a reducing catalyst, such as, an oxygen reducing catalyst.

7a. The microfluidic system of example 6a, the cathode further comprising a cathode conductive layer supporting the oxygen reducing catalyst.

8a. The microfluidic system of examples 6a or 7a, wherein the anode reactive layer comprises a redox mediator.

9a. The microfluidic system of any of examples 6a-8a, the anode reactive layer comprising a selective chemical agent.

10a. The microfluidic system of any of examples 6a-9a, the anode further comprising a protective layer that covers the anode reactive layer.

11a. The microfluidic system of any of examples 7a-10a, wherein the anode conductive layer and the cathode conductive layer each independently comprise a metal.

12a. The microfluidic system of any of examples 7a-11a, wherein the anode conductive layer, the cathode conductive layer, or the combination thereof comprise a high surface area layer.

13a. The microfluidic system of any of examples 1a-12a, comprising a plurality of electrochemical sensors.

The systems may be described in terms of the composition of the electrochemical sensor layers, including specific layer compositions suited for an application of interest, including as outlined below in Examples 14a-21a:

14a. The system of example 10a, wherein the protective layer comprises a biocompatible polymer.

15a. The system of examples 10a or 14a, wherein the protective layer is selected from the group consisting of polyvinyl chloride and chitosan.

16a. The system of example 11a, wherein the metal is selected from the group consisting of gold, silver, platinum, tungsten, titanium, carbon and any combination thereof.

17a. The system of example 12a, wherein the high surface area layer is selected from the group consisting of carbon nanotubes, buckypaper, carbon fibers, carbon fiber paper, metallic nano/micro-particles, ceramic nano/mirco-particles and any combination thereof.

18a. The system of example 8a, wherein the redox mediator comprises tetrathiafulvalene.

19a. The system of example 9a, wherein the selective chemical agent is: an enzyme selected from the group consisting of lactate oxidase, glucose oxidase, pyruvate oxidase, amino acid oxidase, urease, bilirubin oxidase, laccase, and any combination thereof; a reactive polymer selected from the group consisting of polyols, acrylates, silicones, urethanes, and any combination thereof; a biological compound selected from the group consisting of an antibody, an aptamer, a polynucleotide, and any combination thereof; a reagent selected from the group consisting of methylene blue, ferrocene, naphthoquinone, and any combination thereof; or any combination thereof.

20a. The system of any of examples 6a-19a, the cathode further comprising one or more enzymes.

21a. The system of example 6a, wherein the oxygen reducing catalyst is selected from the group consisting of platinum, platinum black, silver oxide, manganese oxide, and any combination thereof.

The systems may be described in terms of the structure of the electronic device, including as outlined below in Examples 22a-30a:

22a. The system of any of examples 1a-21a, wherein the electronic device is configured to receive, generate, or both receive and generate a radiofrequency signal, a magnetic field, heat, electromagnetic radiation, acoustic energy, and any combinations thereof.

23a. The system of example 22a, wherein the electronic device comprises electronic components selected from the group consisting of a radiofrequency antenna, a capacitor, an integrated circuit chip, a resistor, an operational amplifier, an analog-to-digital converter, and any combinations thereof.

24a. The system of example 2a3, wherein the electronic device further comprises: an NFC chip to receive and/or generate an NFC signal; or a BLE chip to receive and/or generate a BLE signal.

25a. The system of any of examples 22a-24a, the electronic device further comprising electronic device memory configured to store an identification code assigned to a user of the system.

26a. The system of example 25a, the electronic device memory further configured to store health data comprising an electrical response from the electrochemical sensor.

27a. The system of any of examples 22a-26a, the electronic device further configured to wirelessly transmit the identification code, the health data, or both.

28a. The system of any of examples 1a-27a having a skin facing surface, wherein the electronic device is permanently or reversibly affixed to the substrate at a surface that is opposed to the skin facing surface and separated from the skin facing surface by a thickness of the flexible substrate.

29. The system of any of examples 1-28, further comprising magnetic pads positioned at one or the combination of the electronic device and the substrate, thereby reversibly affixing the electronic device to the substrate.

30a. The system of any of examples 22a-29a, wherein the electronic device is configured to be read-out actively, passively, or both actively and passively.

Any of the systems may further include colorimetric sensors, including as outlined below in Examples 31a-33a:

31a. The system of any of examples 1a-30a, further comprising a colorimetric sensor fluidically connected to the microfluidic network, wherein the colorimetric sensor has one or more color-responsive reagents each configured to react with a biofluid analyte.

32a. The system of example 31a, wherein the colorimetric sensor is configured to quantify a biofluid property selected from the group consisting of: a biofluid volume, a biofluid flow rate, a biofluid composition, and any combination thereof.

33a. The system of example 31a, wherein the one or more color-responsive reagents are selected from the group consisting of $CoCl_2$, glucose oxidase, peroxidase, potassium iodide, lactate dehydrogenase, diaphorase, formazan dyes, 2,4,6-tris(2-pyridiyl)-s-triazine (TPTZ) complexed with mercury ion or iron ion, a 2,2'-bicinchoninic acid, 1,10-phenanthroline, a universal pH indicator and any combinations thereof.

34. The microfluidic system of any of examples 1-33, wherein the substrate is characterized by a Young's modulus that is within a factor of 20 of an effective skin surface Young's modulus of skin underlying the substrate, and wherein the substrate is capable of conformal contact to the skin surface.

35a. The microfluidic system of example 34a, wherein the Young's modulus of the substrate is less than or equal to 100 MPa.

36a. The microfluidic system of any of examples 1a-35a, wherein the biofluid is sweat.

37a. The system of any of example 4a-36a, wherein the biofluid analyte is selected from the group consisting of an electrolyte, a metabolite, a vitamin, an amino acid, a drug, a protein, and any combination thereof.

38a. The system of any of examples 1a-37a, the microfluidic network further comprising an outlet and a microchannel network, the microchannel network fluidically connected to the biofluid inlet and to the outlet, the outlet configured to reduce backpressure in the microfluidic network to facilitate biofluid introduction to the microchannel network.

Also provided herein are systems having specially configured and positioned electrodes in and extending along a microfluidic channel, including as outlined below in Examples 39a-61a:

39a. A microfluidic system for monitoring a biofluid, the microfluidic system comprising: a flexible substrate; a microfluidic channel at least partially embedded in or supported by the substrate; a biofluid inlet configured to introduce biofluid from the skin surface to the microfluidic channel during use; an outlet fluidically connected to the microfluidic channel and configured to reduce backpressure in the microfluidic channel; at least two biofluid tracking electrodes positioned along the microfluidic channel and spatially separated from each other by a microfluidic channel lumen; and an electronic device in electronic contact with the at least two biofluid tracking electrodes to measure a biofluid property of a biofluid introduced to the microfluidic channel.

40a. The system of example 39a, wherein the electronic device is configured to apply an electrical load to the biofluid tracking electrodes to generate an electrical output from the biofluid tracking electrodes having a value proportional to the biofluid property.

41a. The microfluidic system of example 40a, wherein the electrical load is an alternating current.

42a. The microfluidic system of examples 40a or 41a, wherein the electrical output is a voltage change.

43a. The microfluidic system of examples 40a or 41a, wherein the electrical output is electrical impedance.

44a. The microfluidic system of example 42a, wherein the voltage change detected by the electronic device is a function of impedance between the biofluid tracking electrodes.

45a. The microfluidic system of any of examples 39a-44a, wherein the biofluid property is selected from the group consisting of biofluid volume, a biofluid flow rate, a biofluid analyte concentration or amount, temperature, and any combination thereof.

46a. The microfluidic system of example 45a, wherein the microfluidic system measures the biofluid property as a function of time.

47a. The system of any of examples 39a-46a, wherein the biofluid is sweat.

48a. The system of any of examples 39a-47a, wherein the electronic device is further configured to receive, generate, or receive and generate a radiofrequency signal, a magnetic field, heat, electromagnetic radiation, acoustic energy, and any combination thereof.

49a. The system of example 48a, wherein the electronic device comprises electronic components selected from the group consisting of a radiofrequency antenna, a capacitor, an integrated circuit chip, a resistor, an operational amplifier, an analog-to-digital converter, and any combinations thereof.

50a. The system of example 49a, wherein the electronic device further comprises:
an NFC chip to receive and/or generate an NFC signal; or a BLE chip to receive and/or generate a BLE signal.

51a. The system of any of examples 49a or 50a, the electronic device further comprising electronic device memory configured to store an identification code assigned to a user of the system.

52a. The system of example 51a, the electronic device memory further configured to store health data consisting of the electrical response from the biofluid tracking electrodes.

53a. The system of any of examples 39a-52a, the biofluid tracking electrodes having one or more electrode layers each selected from the group consisting of gold, titanium, polyethylene terephthalate, silica, and any combination thereof.

54a. The system of any of examples 39a-53a, further comprising a protective layer covering the biofluid tracking electrodes.

55a. The system of example 54a, the protective layer having a material selected from the group consisting of polydimethylsiloxane (PDMS), polyurethane, cellulose paper, cellulose sponge, polyurethane sponge, polyvinyl alcohol sponge, silicone sponge, polystyrene, polyimide, SU-8, wax, olefin copolymer, polymethyl methacrylate (PMMA) polycarbonate, and any combination thereof.

56a. The system of any of examples 39a-55a, further comprising an adhesive layer configured to reversibly affix the microfluidic system to a skin surface.

57a. The microfluidic system of example 39a, wherein the substrate is characterized by a Young's modulus that is within a factor of 20 of an effective skin surface Young's modulus of skin underlying the substrate, and wherein the substrate is capable of conformal contact to the skin surface.

58a. The microfluidic system of example 57a, wherein the Young's modulus of the substrate is less than or equal to 100 MPa.

59a. The system of example 40a, the system further comprising an electrochemical sensor having: an anode having an anode conductive layer; an anode reactive layer supported by the anode conductive layer, the anode reactive layer comprising a redox mediator and a selective chemical agent; a cathode having an oxygen reducing catalyst supported by a cathode conductive layer; wherein the electronic device is further configured to apply the electrical load to the electrochemical sensors to detect an electrical response from the electrochemical sensor; and wherein the microchannel is further configured to transport at least a portion of the biofluid to the electrochemical sensor.

60a. The system of any of examples 39a-59a, further comprising a colorimetric sensor having one or more color-responsive reagents each configured to react a biofluid analyte for quantification of a volume, flow rate, composition, or any combination of these of the biofluid; wherein the microchannel is further configured to transport at least a portion of the biofluid to the colorimetric sensor.

61a. The system of any of examples 39a-60a, wherein the microfluidic channel has a length, and each of the at least two biofluid tracking electrodes extend at least 70% of the microfluidic channel length.

Any of the systems may be used in a method of monitoring a biofluid property, including as outlined below in Examples 62a-68a:

62a. A method of monitoring a biofluid property, the method comprising the steps of: mounting a microfluidic system to a skin surface, wherein the microfluidic system has an electrochemical sensor comprising a biofluid working electrode and a counter-electrode to measure a biofluid property of a biofluid released from the skin surface; introducing a biofluid released from the skin surface to the electrochemical sensor; applying an electrical load to the biofluid working electrode; and detecting an electrical parameter with the biofluid counter-electrode, thereby monitoring the biofluid property.

63a. The method of example 62a, wherein the microfluidic system comprises any of the systems described herein.

64a. The method of example 62a, wherein the step of applying further comprises applying the electrical load to a functionalized working electrode.

65a. The method of example 64a, wherein the step of detecting further comprises detecting an electrical parameter at a counter electrode.

66a. The method of example 65a, wherein the functionalized working electrode is an anode.

67a. The method of example 66a, wherein the counter electrode is a cathode.

68a. The method of example 67a, wherein the electrical parameter has a value that is proportional to the biofluid property.

69a. Any of the systems and methods described herein, wherein the substrate is a functional substrate.

Example 2. Materials and Method for Creating High-Contrast, Non-Wicking Paper Microfluidic Sweat Loss Sensor Example 2 Abstract: Current methods for measuring sweat volume loss from the skin rely on absorbent pads taped to the skin, but do not offer the ease of use in sweat capture needed for quantitative or real time tracking. Here, a thin, soft, "skin-like" microfluidic platform is introduced that bonds to the skin to allow for collection and storage of sweat in a set of paper channels. Pressure induced by the sweat glands drives flow through a network of discrete paper segments, that incorporates intermittent air gaps designed to limit wicking to a predetermined length. Utilization of a water indicator tape which changes color from white to red enables high contrast, real time readout to the user.

Applications: The systems and methods herein provide real time sweat loss monitoring. The described systems have simple fabrication, e.g. they do not require photolithography. In some embodiments, the provided water contact indicator is high contrast and humidity stable (e.g. functional in wet environments).

Figure 7:
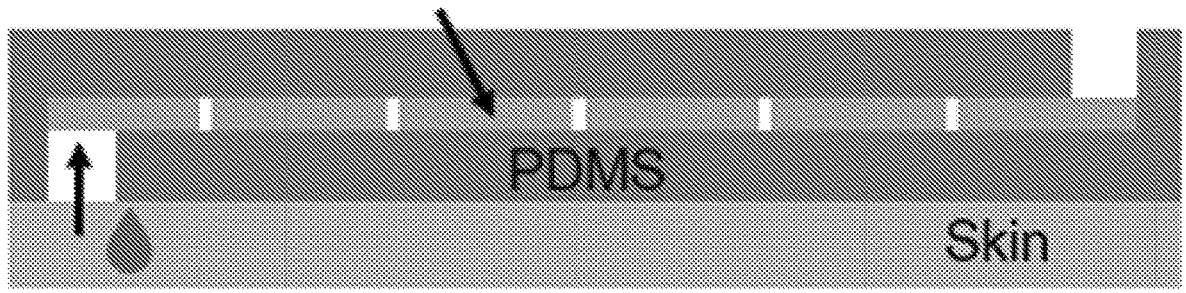
FIG. 7. Panel A is a schematic showing a side view of a microfluidic sweat loss sensor, such as one according to Example 2. Panel B is a schematic showing a cross sectional view of the exemplary sensor.
Figure 7:
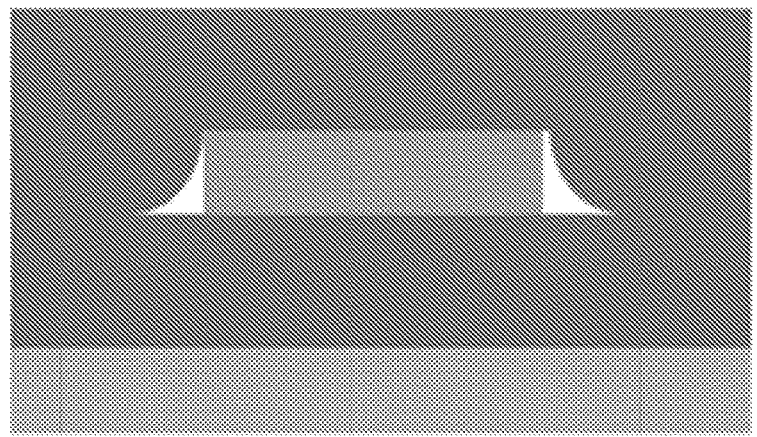

Sensor structure: The structure consists of a water contact indicator tape that is laminated between two polymer layers. These polymer layers may consist of a styrene block copolymer (SBC) such as styrene-ethylene-butadiene-styrene (SEBS), styrene-isoprene-styrene (SIS), or styrene-butadiene-styrene (SBS), and optionally a low molecular weight hydrocarbon such as mineral or paraffin oil. The mechanical properties (modulus and strain-to-failure) are able to be augmented by addition of the oil. The indicator paper is patterned into thin channels and serves as the conduit for water transport from a 1 mm input that is punched in the bottom layer (see FIG. 7, panel A). A 1 mm outlet for the relief of air pressure is punched at the opposite end of the channel in the top layer. The periodic segmentation of the indicator paper serves to minimize the effects of wicking in the paper, which allows for a more accurate measurement of sweat loss. As sweat is pushed into the channel it is wicked along the paper channel until it reaches a break (or gap) in the paper. Additional sweat volume is required to push the sweat past this boundary. This enables a readout which indicates volumetric information, which is not possible with a single paper channel which is susceptible to extensive wicking.

Transfer printing of indicator tape: Patterning of the indicator tape is performed by laser cutting or die plotting. The indicator paper consists of an indicator paper sticker on PET backing, and the cutting action is limited to the thickness of the indicator paper leaving the backing intact. The unused regions of the paper sticker are removed to prepare the patterned paper for transfer to the substrate. A transfer stamp comprised of an SBC, low molecular weight hydrocarbon, and tackifier is used to lift the sticker off the backing, as the stamp-paper interfacial adhesion is stronger than the paper-backing or stamp-backing interfaces. Lamination and light pressure enables bonding of the paper to the final substrate and the transfer stamp is slowly peeled away. The top polymer layer is bonded via heating to 75° C. and the application of light pressure. The temperature and pressure applied for bonding the top polymer layer dictate the cross sectional-geometry of the channel (FIG. 7, panel B) and can be modified to alter the channel volume.

Figure 8:
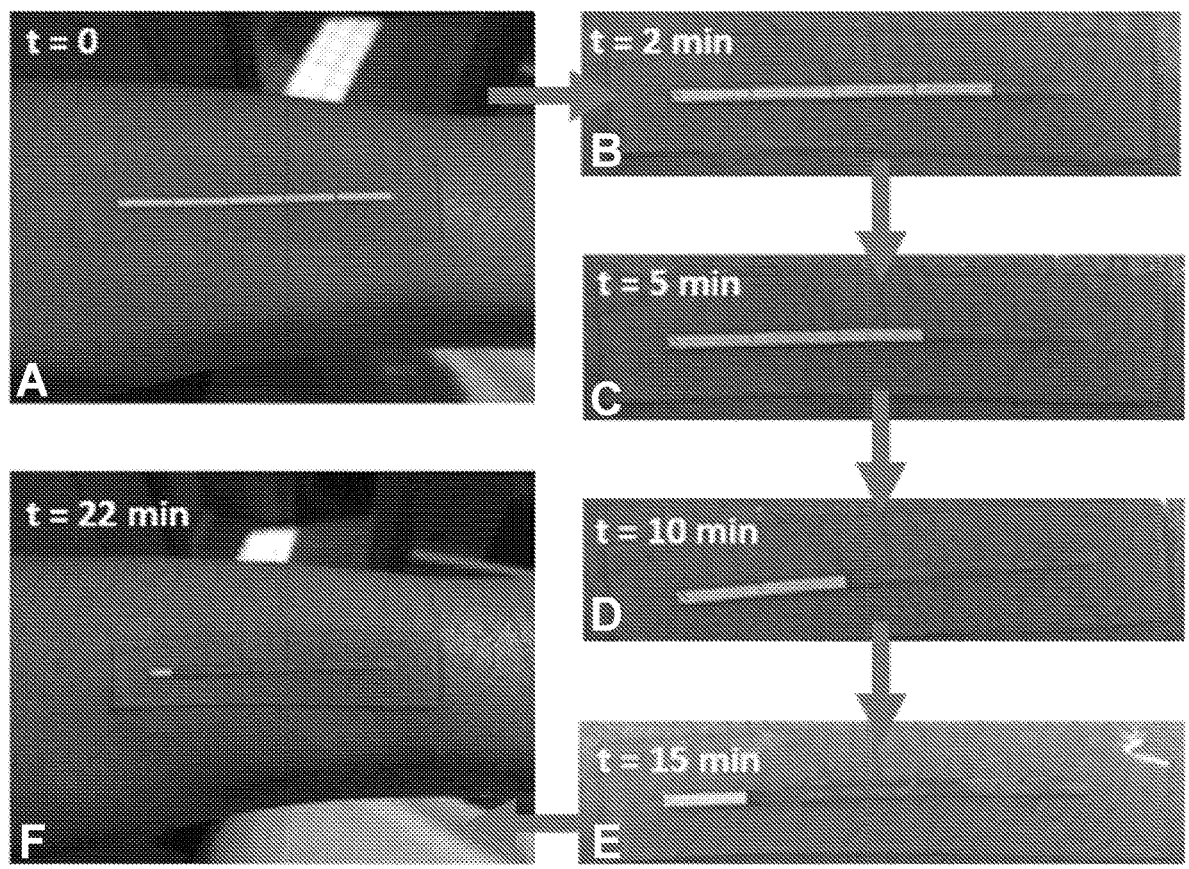
FIG. 8. Panels A, B, C, D, E, and F are time-sequential photographs of an exemplary biofluid monitoring device, such as one according to Example 2. Panels A, B, C, D, E, and F correspond to a time of 0 min, 2 min, 5 min, 10 min, 15 min, and 22 min, respectively.

FIG. 8 (panels A-F) illustrates the device being used by a subject and shows the sequential biofluid monitoring device over time-panels A, B, C, D, E, and F corresponding to a time of 0 min, 2 min, 5 min, 10 min, 15 min, and 22 min, respectively. This demonstrates as additional biofluid enters the system, additional segments of the indicator tape become wet and change color, allowing for a viewer to determine biofluid volume based on the number of wet segments.

Additional Examples

Provided herein are representative examples of various systems and methods.

Example 1b. An epidermal microfluidic system for measuring a characteristic of a biofluid from a skin surface comprising: a) a flexible substrate; b) a biofluid inlet embedded on or supported by the substrate for receiving the biofluid from the skin surface; and c) a microfluidic channel embedded in or supported by the flexible substrate and fluidically connected to the inlet to receive the biofluid; the microfluidic channel having an indicator comprising a series of indicator tape segments configured such that the biofluid is transported along the series by wicking, wherein each of the indicator tap segments in the series is independently separated from at least one adjacent tape segment by a gap such that additional sweat volume is required to transport the biofluid through the gaps in the series.

2b. A method for determining sweat loss comprising: a) providing an epidermal microfluidic system in contact with a skin surface of a subject, the system comprising: i) a flexible substrate; ii) a biofluid inlet embedded on or supported by the substrate for receiving the biofluid from the skin surface; and iii) a microfluidic channel embedded in or supported by the flexible substrate and fluidically connected to the inlet to receive the biofluid; the microfluidic channel having an indicator comprising a series of indicator tape segments configured such that the biofluid is transported along the series by wicking, wherein each of the indicator tap segments in the series is independently separated from at least one adjacent tape segment by a gap such that additional sweat volume is required to transport the biofluid through the gaps in the series; and determining the subject's sweat loss by measuring the number of indicator tape segments which have contacted sweat.

3b. A method for fabricating a real-time sweat loss monitoring system comprising the steps of: a) providing an indicator having an indicator paper and a backing; b) patterning the indicator into a plurality of indicator paper segments; c) removing the indicator paper segments using a transfer stamp; d) placing the indicator paper segments onto a first flexible substrate; e) removing the transfer stamp; f) placing a second flexible substrate on the first flexible substrate, wherein the first and second substrates are formed to generate a channel containing the indicator paper segments; g) heating, providing pressure, or heating and providing pressure to create a fluidic seal between the first and second flexible substrate thereby generating a microfluidic channel; h) generating a biofluid inlet in fluidic communication with the microfluidic channel, thereby producing a real-time sweat loss monitoring system.

4b. The system or method of any of examples 1b-3b, wherein the system is for measurement of sweat volume loss or sweat volume loss rate.

5b. The system or method of any of examples 1b-3b, wherein the system further comprises a fluid outlet fluidically connected to the microfluidic channel.

6b. The system or method of any of examples 1b-3b, wherein the flexible substrate is polydimethylsiloxane (PDMS).

7b. The system or method of any of examples 1b-3b, wherein the flexible substrate is a styrene block copolymer selected from the group consisting of: styrene-ethylene-butadiene-styrene (SEBS), styrene-isoprene-styrene (SIS), styrene-butadiene-styrene (SBS) and any combination thereof.

8b. The system or method of any of examples 1b-3b, wherein the substrate further comprises a low molecular weight hydrocarbon, mineral oil, paraffin oil or any combination thereof.

9b. The system or method of any of examples 1b-3b, wherein the system further comprises an adhesive layer.

10b. The system or method of example 9b; wherein the adhesive layer comprises an adhesive capable of reversibly adhering to the skin surface.

11b. The system or method of any of examples 1b-3b, wherein the flexible substrate has an average thickness selected from the range of 250 μm to 2 mm.

12b. The system or method of any of examples 1b-3b, wherein the indicator is a patterned indicator.

13b. The system or method of example 12b, wherein the patterned indicator is micropatterned or nanopatterned.

14b. The system or method of any of examples 1b-3b, wherein the indicator tape segments are water contact indicator tape segments.

15b. The system or method of any of examples 1b-3b, wherein the biofluid inlet has a diameter selected from the range of 500 μm to 5 mm.

16b. The system or method of example 5b, wherein the fluid outlet has a diameter selected from the range of 500 μm to 5 mm.

Example 3: Battery-Free, Skin-Interfaced Microfluidic/Electronic Systems for Simultaneous Electrochemical, Colorimetric and Volumetric Analysis of Sweat Recently reported technologies for analyzing sweat rely either on active, battery-powered electronics for electrochemical detection or passive, colorimetric chemistries for visual readout. Complex construction and large size/weight represent disadvantages of the former; semi-quantitative operation and limited scope of measurable biomarkers are limitations of the latter. In this Example, we introduce a unique, unconventional class of battery-free, wireless microelectronic platform that performs sensing via schemes inspired by the operation of biofuel cells. Combining these systems in a magnetically releasable manner with chrono-sampling microfluidic networks that incorporate assays based on colorimetric sensing yields thin, flexible, lightweight, skin-interfaced technologies with broad functionality in sweat analysis. Seamless merger of biofuel cells, colorimetrics, NFC electronics and microfluidics results in a wearable chemical sensor which is several orders lighter, cheaper and smaller than reported alternatives with no apparent effect on its performance. A demonstration device (FIG. 9) allows simultaneous monitoring of sweat rate/loss, along with quantitative measurements of pH and of lactate, glucose and chloride concentrations using biofuel cell and colorimetric approaches. Systematic studies of the electronics designs, the microfluidic systems and the integration schemes establish the key design considerations and performance attributes. Capabilities in measurements with short- and long-range wireless reader systems in the context of personalized fitness monitoring suggest a broad range of application possibilities. Human trials involving measurements of sweat glucose and lactate concentrations and comparisons to levels in the blood over a period of two days highlight the ability for long-term monitoring of sweat analytes as a potentially non-invasive means to track corresponding blood concentrations. These successful studies represent the first examples of skin-interfaced sweat sensors with multi-day operational use.

Exemplary Device Fabrication Protocols:
Fabrication of the microfluidic module.

The fabrication process begins with sequential cleaning of a 4" silicon wafer with isopropyl alcohol, acetone, deionized water, and a final rinse with isopropyl alcohol. Next, spin coating a 15 µm thick film of photoresist (KMPR 1010; Microchem, MA, USA) following by baking at 110° C. for 5 min on a hot plate prepares the system for photolithographic patterning to define the geometry of the microfluidics. Exposing the wafer to UV light through a photomask mounted on the wafer, followed by baking at 110° C. for 3 min in a closed chamber, and then for 2 min in an open setup patterned the photoresist. Immersing the substrate in developer solution (AZ 917 MIF; Integrated Micro Materials, TX, USA) completed the process. Subsequently, deep reactive ion etching (STS Pegasus ICP-DRIE, SPTS Technologies Ltd.) created 600 µm deep micro patterned trenches in the silicon wafer. Finally, spin coating poly(methylmethacrylate) (PMMA; Microchem, MA, USA) on the pattered silicon mold and baking at 180° C. for 3 min primed the mold to facilitate release of polydimethylsiloxane (PDMS; Sylgard 184, Dow corning, MI, USA) cast and cured on top, as described next.

Dispersing 5 wt % white silicone (Reynolds Advanced Materials, IL, USA) into a transparent PDMS precursor (10:1, Sylgard 184) yielded a thick liquid cast onto the mold by spin coating at 200 rpm. Curing at 70° C. for 1 h yielded a 700 µm thick, soft, white microfluidic structure. A mechanical punch tool defined 1-mm diameter inlet holes for the colorimetric channels and 3-mm diameter inlet holes for the electrochemical chambers. Pouring PDMS (10:1) on a PMMA coated silicon wafer then spin casting at 400 rpm and curing at 70° C. for 1 h produced a uniform, 200 µm thick slab as a cap for the microfluidic platform. An additional layer of PDMS (60:1) spin cast at 1000 rpm and cured for another 1 h at 70° C. formed a thin, tacky coating. Separately, a commercial laser printer (Konica Minolta C454 PS color, Tokyo, Japan) printed color reference markers on a 25 µm thick polyester (PET) film (FLX000464; FLEXcon, MA, USA), and a $CO_2$ laser (Universal Laser Systems, AZ, USA) defined sweat inlet holes in a skin adhesive membrane (PC2723U, ScapaHealthcare). Assembly of the microfluidic patch involved placing the colorimetric assays, electrochemical sensors, and neodymium magnets (D0105 Nickel; SuperMagnetMan, AL, USA) into their respective chambers and then laminating the sticky side of the capping layer onto the top of the microfluidic patch. Plasma treating a skin adhesive membrane, the color reference marker film and the microfluidic platform with a handheld corona generator yielded hydrophilic surfaces that allowed efficient bonding of the stack to complete the fabrication.

Development of colorimetric assays for chloride and pH.

The colorimetric chloride assay solution comprised 50 mg of silver chloranilate (MP Bioscience, CA, USA) dispersed in 200 µL of 2 wt % polyhydroxyethylmethacrylate (Sigma-Aldrich, MO, USA) methanolic suspension. Drop-casting 0.5 µL delivered this chloride assay cocktail in the chambers designated for chloride sensing. Suspending 4 mL of universal pH dye (Fisher Scientific, NH, USA), 274 mg of polyvinyl chloride (M.W. ~233,000; Sigma Aldrich, MO, USA), 635 µL of o-nitrophenyloctylether (Sigma Aldrich, MO, USA) and 508 µL of Aliquat (Sigma Aldrich, MO, USA) in 10 mL of tetrahydrofuran (Sigma Aldrich, MO, USA) yielded the pH assay solution. Dip-coating filter papers (Sigma Aldrich, MO, USA) in the pH cocktail for 10 s, and allowing them to dry at ambient conditions for 15 min formed the solid-state pH assay. Cutting the pH assay paper into circular pads using a metal punch (diameter, 2 mm) and placing them in each of the chambers designated for pH sensing completed the process.

Fabrication of Biofuel Cell-Based Electrochemical Sensors for Lactate and Glucose.

Electron beam evaporation (AJA International Inc., MA, USA) formed a thin film of chromium (thickness, 10 nm) as an adhesion layer, followed by a layer of gold (thickness, 100 nm) as a conductor on a 75-µm thick sheet of polyimide (Argon Inc., CA, USA). A UV laser (LPKF, Germany) patterned the gold coated polyimide sheet to define the circular current collector, serpentine interconnects, and contact pads. The first step in realizing a biofuel cell-based lactate sensor involved punching out circular pads (diameter, 2 mm) of CNT paper (Thin Film BA-01-145; Nano-TechLabs, NC, USA). Coating with 2 µL of 0.1M tetrathiafulvalene (Sigma Aldrich, MO, USA) solution prepared in acetone/ethanol (1:9 v/v) and 4 µL of lactate oxidase (Toyobo Chemicals, Japan), and allowing them to dry, yielded enzyme functionalized CNT pads. The enzyme solution resulted from dispersing the enzyme (60 mg/mL) in 0.1M phosphate buffer containing 0.25 wt % glutaraldehyde (Sigma Aldrich, MO, USA). Subsequently, drop-casting and drying 2 µL of chitosan (CAS Number 9012-76-4; Sigma Aldrich, MO, USA) suspension prepared in 0.1M acetic acid onto each pad formed a chitosan-based membrane. Dipping the dried pads into the chitosan solution for 5 s and then allowing to dry resulted in an additional chitosan membrane. Finally, dipping the pads for 5 s in 3 wt % polyvinyl chloride (PVC) (CAS Number 9002-86-2; Sigma Aldrich, MO, USA) suspension in tetrahydrofuran, and thoroughly air drying them formed the outer layer of PVC membrane. Conductive silver glue then bonded the pads to the gold current collectors to complete the anode functionalization process. The cathode for the lactate sensor resulted from drop casting 15 µL of 10 mg/mL platinum black (Sigma Aldrich, MO, USA) suspension prepared in deionized water, followed by applying 1 µL of Nafion®117 solution (Sigma Aldrich, MO, USA), onto the cathode designated gold current collector. Storing the sensors at 4° C. for at least 1 week before use allowed the chitosan and PVC membranes to stabilize. Fabrication of biofuel-cell based glucose sensors involved steps similar to those discussed for the lactate sensor with some modifications. The process began with drop-casting 1 µL of 0.1M tetrathiafulvalene solution onto CNT pads. Separately, preparing a 40 mg/mL solution of glucose oxidase in 0.1M phosphate buffer containing 10 mg/mL bovine serum albumin (Sigma Aldrich, MO, USA) and a 1 wt % suspension of Nafion® in 0.1M phosphate buffer and then mixing of the two suspensions in equal volumes yielded the enzyme coating suspension. Application of 2 µL of the enzyme coating suspension functionalized the tetrathiafulvalene coated CNT pads. Conductive silver glue bonded the pads to the gold current collectors to complete the anode. The glucose sensor cathode resulted from preparing a 10 mg/mL suspension of 10% platinum on carbon (Sigma Aldrich, MO, USA) in a 2 wt % ethanolic suspension of Nafion® followed by casting 5 μL of the suspension on each current collector. Storing the sensors at 4° C. for at least 1 week before use allowed the Nafion® membrane to equilibrate. Both the lactate and glucose sensors were stable for at least 6 months when store at 4° C. without any additional storing conditions. Prior to use exposure of glucose sensors to buffer solution resulted in stabilized signals for micromolar detection in sweat.

Fabrication of Battery-Free NFC-Based Electronics.

A LPKF U4 UV laser patterned a commercial substrate (Du pont Pyralux AP8535R) to form a flexible printed circuit board (PCB) for the wireless, battery-free electronics. Pulsed mode electroplating (LPKFContac S4) filled the vias with copper to form connections between the top and bottom layers of the device. The electronics assembly comprised soldering the microcontroller and NFC frontend combination (TI RF430FRL152H), zero crossover operational amplifier (Analog devices ADA4505-2) and various passive resistor and capacitor components in 0201 form-factor, using low temperature solder (Indium corp. In/Sn 90/10) paste. Finally, a 14 μm thick layer of parylene formed by chemical vapor deposition (SCS Labcoter®2 Parylene Deposition System, Specialty Coating Systems, IN) serves as a waterproof encapsulation for the entire system of NFC electronics.

Comments Regarding Working Principle of Biofuel-Cell Based Electrochemical Sensors:

A typical biofuel cell based electrochemical sensor comprises of an enzyme functionalized anode and an oxygen reducing cathode. The enzyme selectively catalyzes the oxidation of the desired analyte (e.g., lactate or glucose) and thus offers selectivity to the biofuel cell based sensors. In addition to the enzyme, the anode also includes a redox mediator for efficiently shuttle electrons from the enzyme's active site to the current collector. The cathode is fabricated by coating catalysts for oxygen reduction reaction. Oxidases and dehydrogenase enzymes are typically used for selectively oxidizing the desired analyte. Commonly used redox species, such as, but not limited to, tetratiafulvalene, quionones, redox dyes act as electron shuttles. Current collectors include, gold, platinum, stainless steel, carbon. Performance of the sensors can be increased by incorporating nanomaterials such as but not limited to, carbon nanotubes, graphene, metal nanoparticles, metal oxide nanoparticles, etc. The oxygen reducing cathodes include functionalizing current collectors with noble catalysts (platinum black, platinum on carbon, ruthenium on carbon), or enzymes such as laccase, bilirubin oxidase that reduce dissolved oxygen to water. Both anode and cathode are further coated with polymeric membranes to obviate leaching of chemical reagents, as permselective layer to reduce interference from other chemicals and extend the detection range of the sensor.

When exposed to the sample (e.g., sweat), the analyte (e.g., but not limited to, glucose and/or lactate) gets spontaneously oxidized at the anode while dissolved oxygen gets reduced at the cathode. These spontaneous reactions lead to a flow of current between the two electrodes whose magnitude is proportional to the concentration of analyte. By applying a fixed resistor between the anode and the cathode one can measure the output voltage (which is a function of concentration; $V=I*R$ and I a concentration) using NFC electronics.

Hybrid, battery-free, skin-mounted system for sweat sensing.

The platform includes two components: a disposable soft, microfluidic network, and a re-usable, thin NFC electronics module. An exploded view illustration of the overall construction of each of these sub-systems is in FIG. 9, panel A. A low-modulus (~1 MPa) silicone elastomer, patterned using soft lithographic techniques, defines a set of isolated chambers for colorimetric and electrochemical sensing, a ratcheted channel for quantifying sweat rate and total sweat loss, and a collection of interconnecting microchannels with passive, capillary bursting valves for routing sweat through the device. A patterned layer of skin-compatible adhesive enables robust attachment to the skin and it defines openings as interfaces between the skin and inlet ports in the bottom side of the microfluidic structure. The soft, flexible construction, as illustrated in FIG. 9, panel B, allows comfortable, water-tight, irritation-free mounting onto curved regions of the body.

Figure 9:
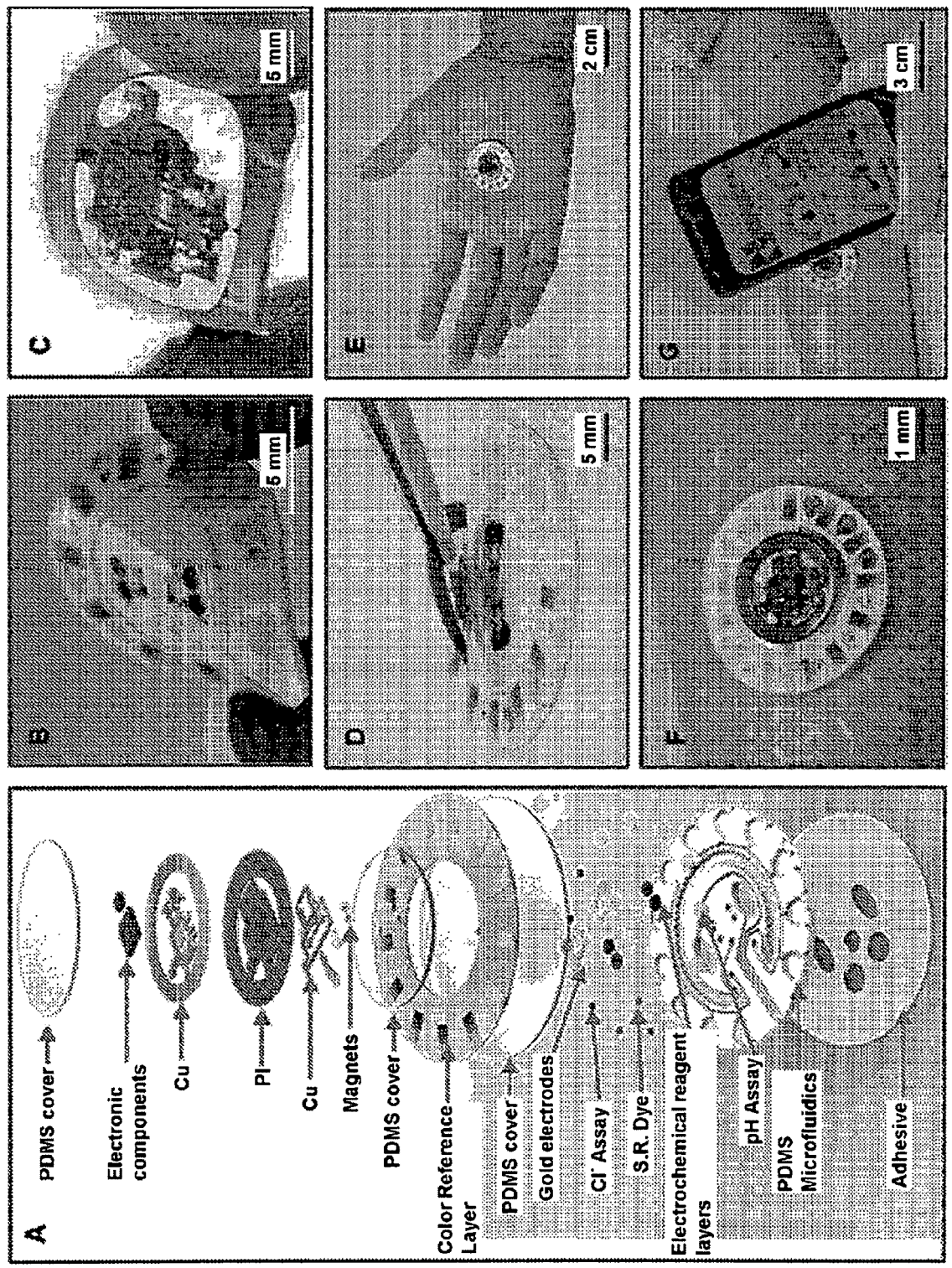
FIG. 9. Device concept schematics. Panel A is a schematic illustrating the exploded view of the complete hybrid battery-free system. Panel B is a close-up image of microfluidic patch with embedded sensors (Panel C) battery-free NFC electronics. Panel D is an image illustrating the reversible magnetic attachment of the NFC electronics to the micro-fluidic patch. Panel E is an image of the complete system. Panel F is an image illustrating device during sweating. Panel G is an image of a phone interface that illustrates wireless communication and image acquisition.

FIG. 9, panel C shows the electronics module, where the NFC interface supports both wireless power delivery and data transmission to any NFC-enabled consumer device, such as a smart phone, tablet or watch. The design exploits a two-layered flexible circuit with minimal component count and a battery-free configuration for real-time data acquisition from lactate and glucose sensors in a biofuel cell layout located in the microfluidic structure. The biofuel cell design involves a voltage amplifier with defined sensor element load implemented with a small footprint operational amplifier and miniature passive components. The circuit conditions the signal for digitalization within the integrated NFC chip (TI RF430FRL152H). The analog electronics are robust, with minimal susceptibility to external noise caused by the NFC electronics and fluctuations in the supply voltage.

To enable re-use, the electronics mount onto disposable microfluidic systems with a releasable electro-mechanical interface. For example: a set of thin, small-scale neodymium magnets (diameter, 1 mm; height, 0.5 mm) affixed with conductive adhesives to contact pads on the backside of the electronic platform and another set embedded in recessed wells underneath contact pads to the electrochemical sensors in the microfluidic platform enable reversible, mechanically robust and self-aligning attachment with low resistance electrical coupling (FIG. 9, panel D). FIG. 9, panel E shows a photograph of the complete system. In one example of use, the user first adheres the microfluidic system to the skin, then magnetically mounts the electronics on top. An NFC enabled portable device or a long-range reader placed in proximity initiates wireless, real-time data acquisition from the lactate and glucose biofuel cell sensors. Visual readout or analysis of digital images allows colorimetric quantification of chloride, pH, and sweat rate/loss. FIG. 9, panel F, shows a system attached to the forearm during sweating. In one example of use, the NFC functionality in a smartphone enables wireless data extraction and its camera permits digital colorimetric analysis, as illustrated in FIG. 9, panel G.

Figure 10:
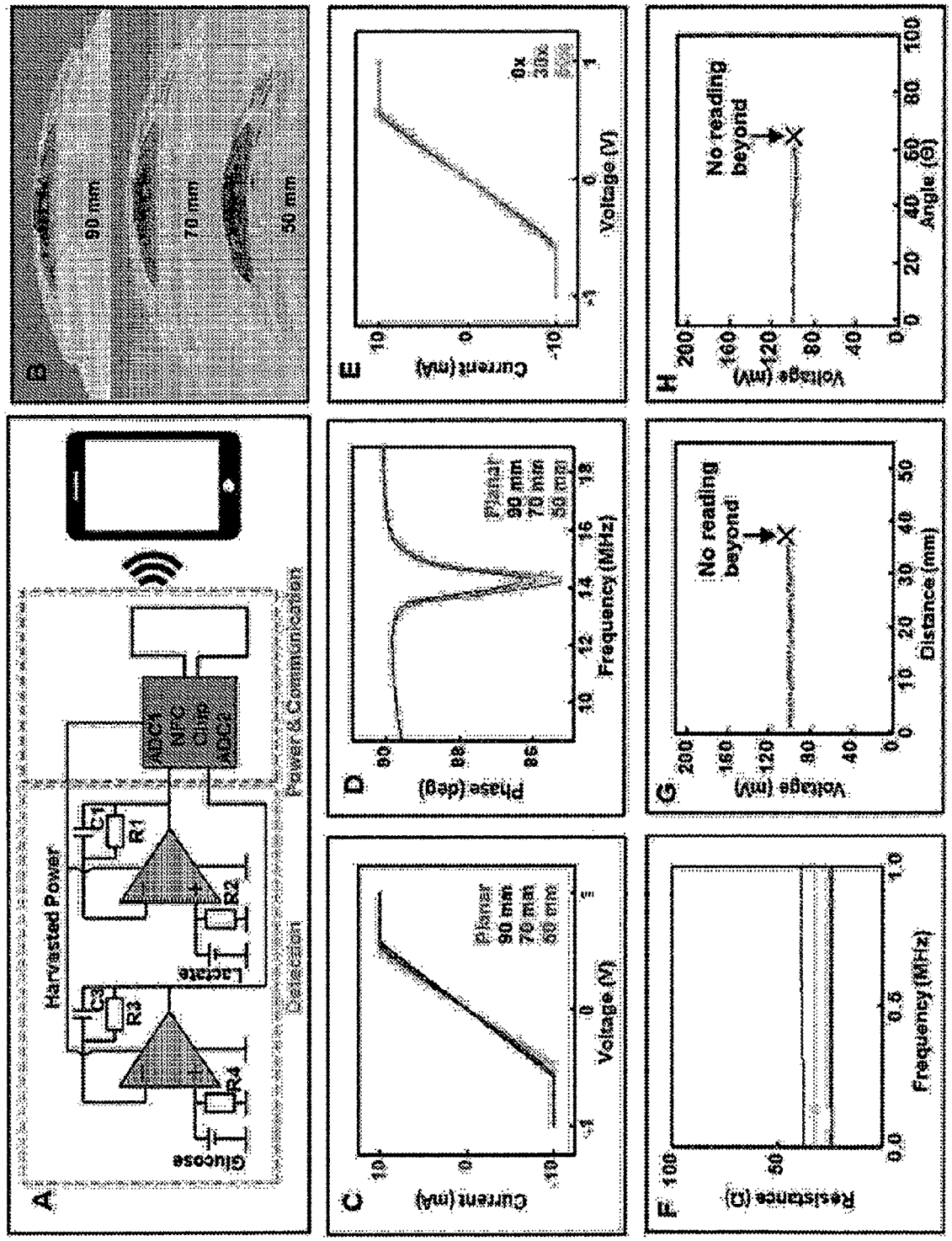
FIG. 10. Electrical characterization of NFC electronics. Panel A is a simplified schematic of electrochemical sensor readout. Panel B is an image illustrating the device bent at decreasing radii. Panels C is a plot showing I-V measurements of shorted sensors recoded with decreasing curvature radii. Panel D is a plot showing phase response measurements of NFC electronics with decreasing radii. Panel E is a plot showing I-V measurements of shorted sensors with repeated attachment and detachment of the electronics to the micro-fluidics. Panel F is a plot showing impedance of magnetic contacts over a wide range of frequencies. Panel G is a plot showing effect of distance and Panel H is a plot showing effect of angle between NFC reader and device on signal recording.

NFC Electronics:

FIG. 10, panel A, presents a simplified schematic illustration to highlight that amplification relies on a simple voltage follower design with a high frequency filter that eliminates fluctuations introduced by the electric field of the primary NFC antenna. This NFC electronics sub-system magnetically couples to electrochemical sensors embedded in a disposable microfluidic substrate. FIG. 10, panel B, shows a completed device adhered to surfaces with small radii of curvature to demonstrate the mechanical robustness of this coupling scheme. FIG. 10 (panels C and D) presents the corresponding current (I) vs voltage (V) curves associated with the magnetic connection and the variation in phase response for the antenna in response to bending. These results highlight stable antenna performance metrics (e.g., Q-factor and resonance peak position) even during mechanical deformations and under cyclical attachment/detachment conditions. FIG. 10 (panels E and F) displays recorded I-V curves and impedance characterization at frequencies up to 1 MHz collected at regular intervals during cyclic testing.

Robust operation follows from electrical working principles that are tolerant to fluctuations in supply voltage that can occur during weak NFC coupling to the reader antenna. Because a non-regulated harvesting circuit scheme may yield the highest possible coupling efficiency, the analog frontend could operate in a manner that is independent of voltage supply to allow for variances in magnetic resonant power transfer and, thus, stable operation in practical scenarios. This goal is accomplished by using a zero-crossover operational amplifier that amplifies the sensor signal regardless of supply voltage, without distortion.

Simulation Program with Integrated Circuit Emphasis (SPICE) software reveals the behavior of the biofuel cell-based lactate and glucose sensors signal conditioning when subject to varying supply voltage (FIG. 14). FIG. 14 (panels C and D) clearly confirms stable data acquisition over the entire range of supply voltages. FIG. 10 (panels G and H) show experimental validation through studies of the effect of distance and angle between the device and a hand-held reader with antenna size comparable to a smartphone (5×3 cm$^2$) on sensor signal quality for the case of a constant reference sensor signal (100 mV) applied to the circuit. FIG. 10, panel G, illustrates that the reader records stable signal from the device at a distance up to ~38 mm. FIG. 10, panel H, shows that the reader is capable of recording uninterrupted, constant signals from the device at angles up to 600. These results demonstrate the broad range of conditions for which reliable data can be acquired, thus highlighting the robust, practical operational capabilities.

Biofuel Cell-Based Electrochemical Sensors for Lactate and Glucose.

The biofuel cell design for the sensors is a critical feature of the systems. A scheme that illustrates different components of the lactate sensor is in FIG. 11, panel A, whereby the anode consists of circularly cut carbon nanotube (CNT) paper that provides a conductive, high surface area substrate to immobilize lactate oxidase (LOx) enzyme, for selectively catalyzing lactate oxidation, and the redox mediator tetrathiafulvalene, for shuttling electrons between the enzyme's active sites and the underlying CNT paper. A chitosan and polyvinyl chloride membrane coat the anode to minimize leaching of the mediator and enzyme, and to extend the linear detection range of the sensor. The cathode comprises of a functionalized current collector of gold with an overlayer of platinum black, all coated with a Nafion® membrane. The platinum black acts as a catalyst for oxygen reduction while the Nafion® membrane prevents leaching of platinum black. The fluoride backbone of the Nafion® polymer facilitates adsorption of dissolved oxygen onto the cathode's surface, thereby improving the kinetic rate of oxygen reduction. An optical photograph of the complete lactate sensor is in FIG. 11, panel B.

Figure 11:
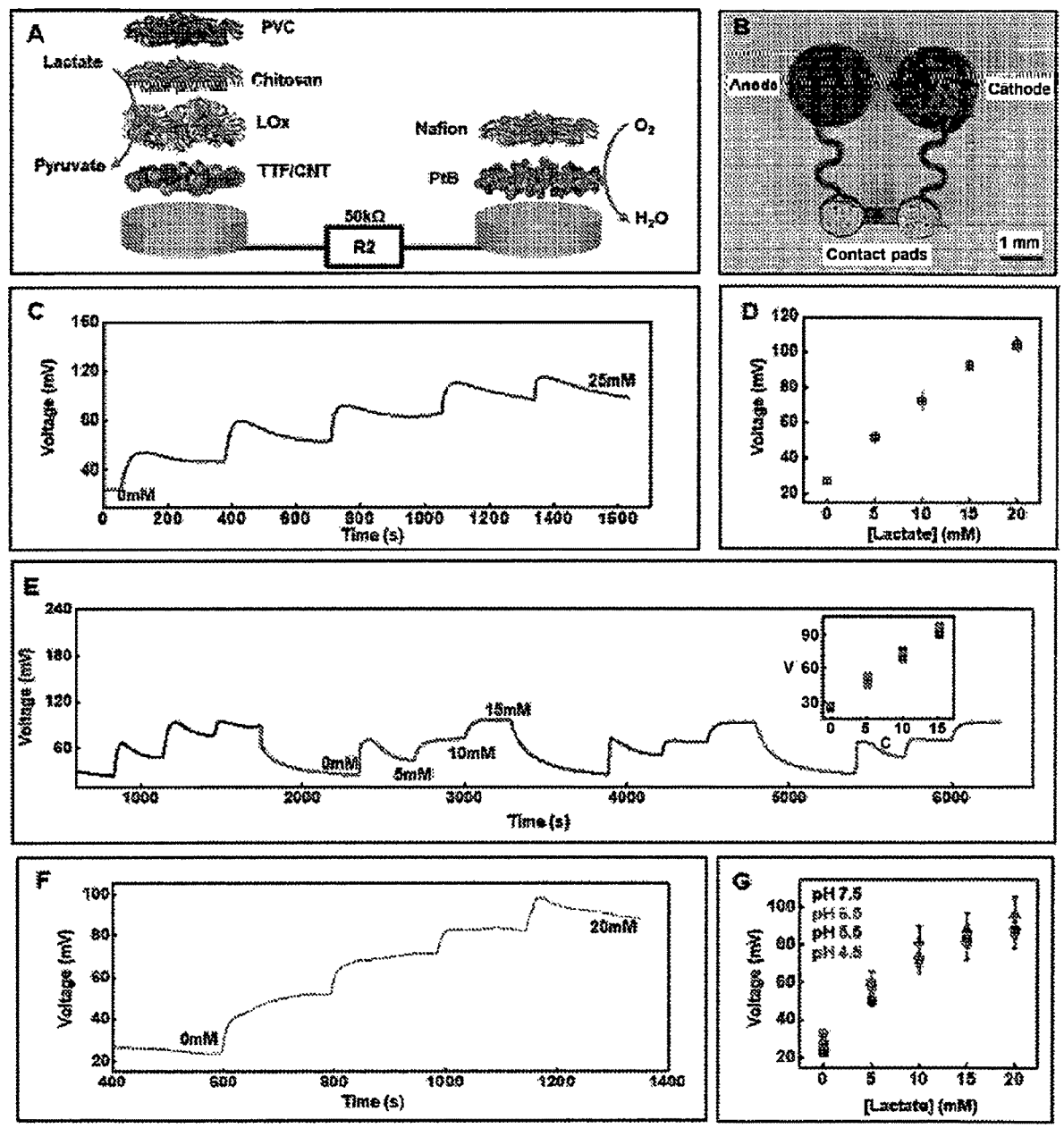
FIG. 11 Lactate sensor characterization. (Panel A) Exploded-view schematic visualizing layer makeup of the fuel cell-based lactate sensor. (Panel B) Image of the actual lactate sensor. (Panel C) Real-time sensor response to increasing lactate concentration in phosphate buffer (pH 7.0)

The anodic and cathodic reactions that generate electrical currents in the lactate sensor are proportional to the concentration of lactate. A resistor connected across the sensor transforms the current into a voltage-based signal for detection and wireless transmission via the NFC electronics. The response of the sensor with increasing lactate concentration, evaluated in phosphate buffer solution at ambient conditions, appears in FIG. 11, panel C. FIG. 11, panel D, shows the corresponding calibration plot, which indicates that the sensor signal stabilizes within 300 s and increases linearly with lactate concentration. This response is reversible (FIG. 11, panel E) as demonstrated in experiments that involve increasing the lactate concentration from 0 mM to 15 mM, reducing it to 0 mM, and then increasing it again in a step-wise fashion back to 15 mM for 4 consecutive cycles. The results highlight linear, reversible responses to time-varying concentrations of lactate concentrations with minimal hysteresis (FIG. 11, panel H) across a physiologically relevant range. FIG. 11 panel F displays response at 30° C. in artificial sweat at pH 5.5 while FIG. 11 panel G shows calibration plot for increasing lactate concentration in artificial sweat with different pH at 30° C.

A similar approach, applied with a few modifications, yields sensors for glucose. Here, glucose oxidase enzyme is directly dispersed in the Nafion® to ensure rapid interaction of glucose with the enzyme and consequent capabilities in detection of micromolar concentrations. The cathode involves a gold-based current collector coated with a suspension of platinized carbon in Nafion® solution. FIG. 12, panel A, illustrates the different components of the sensor and FIG. 12, panel B, presents an image. Comprehensive studies conducted in a manner similar to those for the lactate sensor define the response. FIG. 12, panel C, summarizes real-time measurements as a function of increasing concentrations of glucose in buffer at ambient conditions, with a corresponding calibration plot (FIG. 12, panel D). FIG. 12 panel E shows reversible nature of the sensor response. FIG. 12 F and G illustrate response of sensor in artificial sweat (pH 5.5, 30° C.) and effect of pH on sensor response respectively.

Colorimetric Assays and Microfluidics.

The disposable microfluidic substrate houses the electrochemical sensors, various colorimetric assays and it supports valves, channels and reservoirs for handling small volumes of sweat delivered into the system by the action of the glands themselves. For chloride concentration, the colorimetric assay relies on silver chloranilate, a chemical that complexes with chloride ions to generate a species with a distinct purple color. Mixing silver chloranilate with pHEMA solution creates a gel-like suspension that immobilizes the insoluble silver byproduct in the assay well. The result prevents migration of silver particulates during flow of sweat in the microfluidic channel, thereby eliminating their effects on color extraction. The extent of change in color determines the concentration of chloride through a linear calibration curve, as shown in FIG. 13, panel A. This chemical reaction provides a more reliable, accurate colorimetric response compared to previously reported alternatives for analysis of chloride in sweat. Similarly, paper pads coated with a pH sensitive dye and a phase transfer catalyst serve as a colorimetric means for determining pH. The evolution of color as a function of pH over a physiologically relevant range is in FIG. 13, panel B. Calibration plots reveal the linear relationship between the R value (of the RGB code) at different pH levels. FIG. 15 shows simple color reference bars developed for each of these calibration plots to facilitate visual or digital color extraction and conversion to concentration.

The part of the system designed to measure sweat rate/loss involves a simple, circular channel with a water-soluble dye located near the inlet (FIG. 13, panel C). The incoming sweat dissolves the dye as it flows past, thereby creating a visible, colored fluid with an easily identifiable filling front in the channel. The position of this front defines the local rate and loss of sweat from the corresponding location on the skin. FIG. 16 shows a linear correlation between data acquired from the sweat rate sensor to the normalized total, or full-body, sweat loss. In this particular design, the channel volume (~58 µL) and the dimensions of the inlet interface to the skin allow tracking of sweat loss for up to 6 hours based on an average sweat rate in the range of 12 to 120 mL/hr/cm$^2$.

Although these assays have an irreversible response, time dependent changes in sweat composition can be captured by using fluidic designs that enable time-sequential sampling (chrono-sampling) of sweat using passive valve constructs. The example in FIG. 17, panel A, uses collections of capillary bursting valves (CBVs) to enable sequential filling of a series of independent microreservoirs, each pre-impregnated with a colorimetric reagent. The left and right sides of the device provide chrono-sampling analysis of pH and chloride, respectively.

Since the electrochemical sensors for lactate and glucose are reversible, a single-chamber design with a single channel to divert sweat from this chamber to an outlet is sufficient. These two microfluidic structures flank either side of the patch. The sweat sensor channel resides in between the regions for electrochemical and colorimetric sensing. FIG. 17, panel B, and FIG. 13, panel D, highlight the multimodal microfluidic substrate and chrono-sampling features of the system. Circular holes (diameter, 1 mm) serve as inlets in the base of the microfluidic platform for the sweat rate, chloride and pH sensors while ellipsoidal shaped holes (major axis, 5 mm; minor axis, 3 mm) act as inlets for glucose and lactate sensors. The skin adhesive layer has corresponding circular (diameter of 3 mm) and ellipsoidal (major axis, 6 mm; minor axis, 4 mm) openings.

TABLE 1

Comparison of data acquired from sensor patch and conventional techniques during human trials

| Subject | Parameter | Hybrid Sensor Patch | Conventional technique |
|---|---|---|---|
| Subject #1 | Chloride | 62 ± 5 mM | 66 mM |
|  |  | 36 ± 5 mM | 43 mM |
|  | pH | 6.3 ± 0.05 | 6 |
|  |  | 6.2 ± 0.03 | 5.5 |
|  | Lactate | 10.4 ± 0.1 mM | 17.5 mM |
|  | Glucose | 23.2 ± 2.4 µM | 53 µM |
| Subject #2 | Chloride | 34 ± 2 mM | 40 mM |
|  | pH | 6.4 ± 0.1 | 6.5 |
|  | Lactate | 19.3 ± 0.5 mM | 28 mM |
|  | Glucose | 52 ± 14 µM | 100 µM |

Example 4: Battery Free NFC Based Soft Microfluidics to Readout Sweat Excretion Rate Perspiration is an important physiological phenomenon in the body. The human body regulates temperature, and can emit bodily waste through sweat glands. Furthermore, ion concentration which is directly related to dehydration such as chloride and sodium could be regulated. Thus, knowing sweat rate could be used as an index of body condition, and could aid in preventing dehydration in advance.

Conventionally, sweat rate measurement methods are relatively not advanced, though they are of great interest. Conventional approaches use absorbent an agent such as gauze and sponge. Those approaches involve measuring the difference of the weight of the patch in which gauze or sponge is attached before and after sweating. And the difference could be calculated with the surface area of the patch for sweat rate per unit sweat gland. Additionally, sweat composition was analyzed from the sweat sample which is collected by the absorbent agent. The conventional approach is not promising in terms of accuracy. In the process of absorption and detaching patch from epidermis, there would be some loss of sweat because of evaporation or dropped in case of profuse sweating. And it could be contaminated with exposure to atmosphere. The conventional approach could show some trend of physiological change.

Microfluidics can prevent the issues of evaporation and contamination. As soon as sweat excreted, it is may be collected in the microfluidic channel. We show the possibility of sweat collecting using microfluidics. Microfluidic channel length can be calculated as volume, and if we know the time for the channel filling up, sweat rate can be derived. To know the time, we introduce color change. Channel color changes as the sweat propagates in the microfluidic channel. In our approach, electrodes are sensing the sweat flow in the channel. Sweat has electrolytes and if sweat fluid gets disconnected from the electrodes, the stage of electrode will be closed and there would be some properties of conductor. Then, the fluid can act as a resistor. Biofluids are solutions that have ions. Direct current may not be ideal because if electrodes are charged with direct current, ions may separate according to their preferred charge, and measuring of the resistance could be difficult. Then, we employed alternative current (AC) between electrodes at the sensing stage(s).

This Example shows simple and convenient method to measure the sweat excretion rate using the epidermal soft microfluidics with well fabricated electrodes to readout the information from the sweat propagated. The information may be converted into electrical signal and may be readout using battery free NFC system. The system is designed to process the data and show the data to the users via smartphone screen.

Soft Microfluidics for Sweat Rate Readout and Monitoring:

The device structure has multiple layers with specific functions to be clear and robust in terms of sweat excretion rate and chloride concentration change. FIG. 19 shows the schematics of the device design. There are primarily four layers for NFC data processing, soft microfluidics, flexible electrodes, and adhesive layers (FIG. 19, panel a). Sweat sampling layer comprises flexible electrodes (FIG. 19, panel b) and microfluidic channel with soft-lithography, the assembled microfluidics channel in which copper-gold electrodes are located along the channel shape is to for mounting on the skin directly, and the inlet on the bottom of the channel can collect sweat as soon as it is excreted. The electrodes were fabricated using clad copper sheet of 3 µm/18 µm thickness of working and caring layers. FIG. 19, panel c, shows the optical image of assembled device. The diameter of device assembly is 32 mm. The microfluidics layer thickness is ~500 µm with ~300 µm of microfluidics mold layer and ~200 µm of flexible copper-gold electrodes layer. The device has flexibility to be mounted on various skin curves. And the electronics was designed to be reused by attaching the NFC electronics layer on the microfluidics for sweat tracking (FIG. 19, panel d). Magnets were used to secure the contact quality for robust power/data transferring. Small magnets are used for aligning the NFC electronics layer on the tracking channel, and large magnets are for making connections with the electrodes. As shown in FIG. 19, panel e, aligning with small magnets should be conducted at first, and electrodes contacting would be followed as it is released gently from the finger grabbing. Then it can be mounted on the skin, and the measurement could be performed with the human subjects. Also smartphone can be used to read the data from the battery free sweat readout device which put specific frequency to the electrodes in the microfluidics, and receives the impedance data accordingly. The data can be shown as ADC values on the smartphone screen as the results of measurement, and the data can be calculated to show the current state of the subject who are sweating in the workout.

Electrodes and Properties:

The electrodes are designed to be filled at the points by sweat propagating. The closing of electrodes as the sweat, an electrolyte, could reach up to the point in the channel with the pumping from the sweat gland could be sensed via measuring sweat impedance. Based on the volumes and measured closing times, sweat rate could be calculated. FIG. 20, panel a, shows the structure of electrode fabricated on the PDMS surface. The electrode is formed of copper with titanium deposited on the both sides of copper. The titanium deposition was conducted to prevent the oxidation of the copper electrode surface. If the electrode surface is oxidized substantially, the electronic properties (e.g., resistance) may change and electrical conductivity of the surface may be lost. Ti on another side of the electrode may aid to develop a bridge to the bonding to $SiO_2$. Then, $SiO_2$ could be deposited on the titanium to aid bonding on the PDMS surface. The electrode design includes five time points, and sweat tracking could be conducted on the channels(s) and/or chamber(s) where the electrodes are placed as tracking time points. The device further comprises a reference channel to allow reading the electrolyte concentration change via conductivity measurement. The conductivity may be expressed as resistance, and impedance measurement is utilized in this Example. (In contrast, direct current induced electrolyte separation and migration toward their preferred charged electrode may make measurement difficult). The reference channel dimensions were 6961 μm length distanced electrodes which are in the channel of 200 μm depth and 600 μm widths (FIG. 20, panel b). FIG. 20, panel c, shows the dimensions for the primary tracking channel. FIG. 20, panel d, shows the volumes for each time points. The volume information was used to calculate the sweat rate by dividing the tracking time to the corresponding time point. The tracking channel may store 80 μL of sweat. FIG. 20, panel e, is the impedance measurement with sweeping the frequency from 200 to $1.5 \times 10^7$ Hz; lower frequency showed clear discrimination for each time points. The electrodes were operated with artificial sweat to see the impedance change as the sweat propagates into the channel. FIG. 20, panel f, shows the results of continuous tracking of sweat in the channel. When the flow rate is fixed at 3 μL/min, it showed stair wise like trend of voltage increase. Voltage is reversely proportional to impedance, and it may be utilized for sweat rate tracking. Also reference channel and main channel were calibrated with sodium chloride standard solution (FIG. 20, panels g and h). The results show clear correlation as they show clear discrimination. FIG. 20, panel I, is the results of human sweat plotting from the data of smartphone ADC value and the instrument analysis. The comparison showed good and robust reliability of the electrode and NFC system to be used in situ.

Electronics and Smartphone Communication:

Exemplary device electronics of this Example have three domains for data amplification, data processing, and smartphone communication (FIG. 21, panel a). The data processing system can be powered with RF from the smartphone, and it can generate AC, resulting in current being applied at the tracking electrodes. As the electrodes are filled as the sweat propagates, corresponding impedance is read. The signals of impedance may be collected at the ADC in the data processing part (yellow, middle portion). And before the readout, the signal is amplified (blue, top-left, and green, bottom-left, parts). The data can be transferred to smartphone via the antenna as smartphone hooks up with the NFC system.

FIG. 21, panel b, shows the design of NFC system. The impedance can be measured as comparison with the resisters deducting the values of ground. Main channel resister was found to be 6.8 kΩ as relevant sweat concentration range was tested with the tracking electrodes. And the reference channel resister was found to be 200 kΩ. FIG. 21, panel c, shows the illustration of NFC system, and FIG. 21, panel d, is the optical image of the system. RF antenna was designed as the frequency can be amplified as 13.5 GHz by the resonance (FIG. 21, panel e). And finally the data collected via ADC electrodes can be shown on the screen of smartphone by programmed application (FIG. 21, panel f).

Exemplary Materials and Methods:

Electrodes fabrication: Working side of clad copper sheet of 3 μm/18 μm was coated with PI at 3000 rpm for 30 sec. The sheet was baked at 110° C. for 10 min. separately slide glass was spin-coated with PDMS which 20:1 ratio of elastomer and cross linker. The clad copper was attached on the glass slide to be both side of PI and PDMS are faced. The carrier layer had removed from the working side, and the copper surface had been deposited by E-beam (AJA0000) With Au at 400 Å. PR was coated on the Au surface at 3000 rpm, and the stuff was baked at 110 for 40 sec. Patterning is conducted with mask and mask aligner for photolithography, and it was developed with 400 k developer. Gold and copper were etched with each etchant, and PI was etched by March RIE (200 and 200 W power) for 40 min. Etched pattern was transferred to water soluble tape, and back side of pattern was deposited with Ti and $SiO_2$ with E-beam at 100 Å and 300 Å, respectively. Finally, the $SiO_2$ layer and PDMS surface were bonded after exposure to Harrick plasma at 200 W power.

Silicon wafer mold preparation and channel assembly: To get silicon wafer mold, photolithography was conducted with KMPR spin-coated silicon wafer with film pattern mask after baking the coated wafer on 110° C. hot plate for 5 min. After exposure to UV flood with mask aligning, wafer was baked at 110° C. for 5 min again, and pattern was developed with MF917 developer. The prepared wafer was etched with STS DRIE at 200 μm depth for microfluidic channel and electronics packaging layer and 100 μm for cPDMS electrode development. PDMS of 20:1 ratio was cured on the silicon wafer mold for soft-lithography at 70° C. oven for 4 h after spin-coating at 250 rpm for every layer. The prepared electrode was punched to generate inlets of 0.1 mm diameter at designed location, and channel pattern side of the PDMS molds covered electrode layer at appropriate position aligning the both end of electrodes, electrodes bucket and vias after putting ambient uncured PDMS on the mold side. Magnets were located at the designed position to bind electronics layer. After covering, the channel was baked at 110° C. on a hot plate for 20 min.

Electronics and programing: Double side of circuit board was designed as shown in FIG. 21, panel b, using Cu—PI—Cu layered sheet with laser cutter (model). After laser cutting, circuit board was treated with flux (product) and cleaned with sonicator for 5 min, and dried with $N_2$ blow. Vias were blocked with solder to be connected between upper and below circuit board properly. RF430 was used for an interface of data processing based on NFC. Also, the impedance signals were amplified with Ref AMP chip. All the chips, capacitors, diode, and resisters were placed on the designed circuit board with soldering. After chips placing, program install was conducted in the air. RF430 reader was connected to IBM computer and prepared electronics was activated with air-program-install.

Device packaging: The electronics with programmed RF430 was packed into the PDMS mold which is yielded as same manner of soft microfluidic channel fabrication using silicon mold. Bonding of prepared electrodes and soft microchannel was conducted as the embossed of the channel side was wet with ambient uncured PDMS (10:1 baking on a hot plate 70° C. for 60 min), and contact on the electrodes layer with aligning appropriately after generation of inlets (0.1 mm diameter) on the electrodes layer. Magnets (0.8 mm and 3 mm diameter) for binding electronics on the tracking channel were placed in both layers

Example 5: Resettable Epidermal Microfluidic Sweat Loss Sensor

The black indicator layer is formed by spin coating 10:1 PDMS containing 1.5 wt % black pigment and 1.5% white pigment on a flat PMMA coated wafer. The clear patterned layer is formed by spin coating 10:1 PDMS on a PMMA coated silicon wafer with bas-relief features. Both layers are cured at 100° C. for 1 hr. The scattering material is a commercially available hydrochromic ink (LCR Hallcrest HI51000). The exact composition is unknown. The hydrochromic ink is dispersed in water (5:1 wt water:ink) deposited via air brushing onto the molded PDMS layer and dried at 100° C. for 5 min. Scotch tape is used to remove the ink that is deposited outside the microchannel. Corona treatment of the molded and flat PDMS layers prepares the layers to be bonded. Lamination, light pressing, and heating at 70° C. for 24 hrs ensures a permanent bond between the layers and completes fabrication. See FIG. 22.

Example 6: Thin, Soft, Skin-Mounted Microfluidic Networks with Capillary Bursting Valves for Chrono-Sampling of Sweat and Measuring Pressure from Sweat Gland and Colorimetric Detection of Chloride Soft, Multi-Functional Microfluidic Device for Colorimetric Sweat Analysis:

A soft microfluidic device made from PDMS has flexibility and interfaces to the skin (FIG. 23, panel a). The device provides several functionalities, including: 1) analyzing concentration of chloride, glucose, pH and lactate in sweat, 2) determining temperature of sweat by colorimetric method, 3) calculating local sweat loss and instantaneous sweat rate via adhesive layer that provides a water-tight sealing between skin and the device that enables the device to collect sweat continuously (FIG. 23, panel b). Sweat gland under open region of skin under adhesive generates sweat flow about 2 kPa to 1) inlet #1 and fill the serpentine channel while developing color to detect chloride concentration in sweat and shows the local sweat loss, 2) inlet #2 and fills the collection chambers in clock-wise sequential manner through the guide of series of capillary bursting valves and develop color for detection temperature, glucose, pH and lactate of sweat. For colorimetric analysis, each chamber has thermochromic liquid crystal sensor or chemical assays that develop color according to the temperature or target biomarker in sweat and color reference markers placed around the chamber provide a standard color of target temperature or concentration for accurate color analysis that is not affected by light condition. The exploded view of the device shows the detailed compositions of one device (FIG. 23, panel c). The adhesive layer attaches the PDMS device on to the skin and the hole in the adhesive opens a route for the sweat from the region to enter to the microfluidic channels. White microfluidic PDMS channel layer formed by soft lithography has two channels: the left serpentine channel for measuring chloride concentration and sweat rate, the right sequential circular chambers for measuring glucose, pH and lactate concentration in sweat. The depth of the channel is 600 µm and its relatively thick depth provides sufficient color difference between concentration from the chamber for accurate detection of biomarker of sweat using colorimetric method. The chemical assay components are located in each chambers and channel for their purpose. A 200 µm thick clear 10:1 PDMS capping layer coated with stick PDMS from fully cured 50:1 PDMS generates the closed channel to the microfluidic layer. The sticky PDMS adhesion is preferred due to it not requiring heating process or oxygen plasma treatment that could affect to the stability of chemical assay in the chambers. On top the capping layer, a 25 µm thick thin PET film with reference color marker provide an accurate color analysis. FIG. 23, panel d, shows the process of 1) collecting sweat from exercising, 2) taking picture by smartphone camera, and 3) analyzing color from the chambers to calculate the sweat concentration. Comparing the color value from the reaction chamber with values from color reference marker facilitates estimating the sweat concentration in chamber.

Exemplary Device Fabrication Protocols:

Fabrication began with making a silicon wafer mold. Patterning photo-resist of KMPR 1010 (Microchem, MA, USA) on 1 mm thick Si-wafer and deep reactive ion etching (STS Pegasus ICP-DRIE; SPTS Technologies, Newport, United Kingdom) generated a mold for microfluidic channel. Thin layer of poly(methylmethacrylate) (PMMA; Microchem, MA, USA) formed on the mold. Pouring 10:1 PDMS (Sylgard 184; Dow corning, MI, USA) mixed with white silicone dye (Reynolds Advanced Materials) at 10% wt on the mold and spin coating at 150 rpm with baking at 150° C. for 3 min yielded a 700 µm thick layer. All the chemical assays were located on the cured PDMS channel. Sequential process of pouring 10:1 and 50:1 PDMS and spin coating at 400 and 1000 rpm baking at 150° C. for 3 min yielded a 200 µm thick layer and 75 µm thick layer, respectively. 50:1 PDMS provided a sticky layer to bond between microfluidic channel layer and capping layer. 25 µm thick clear polyester film (THERMLfilm SELECT® 10852; FLEXcon, MA, USA) on the top of the device with color reference marker. 60 µm thick medical grade acrylate adhesive (1524; 3M, MN, USA) bonded to the bottom of the device through 30 sec of laboratory corona treater (Electro-Technic Products).

Color Development and Reference Marker:

Colorimetric method for detection of biomarkers may be aided by a color reference marker for accurate analysis of color regardless of light condition. FIG. 24, panel a, shows the collection of color reference markers for analyzing temperature, chloride, glucose, pH and lactate from sweat. For the preparation of the color reference marker, in vitro test with standard solution produced reference color and digital imaging and image analysis provides color value of each assay. From the values, the color reference marker is generated and printed on the thin and clear film and attached to the top of the device. Mixture three kinds of thermochromic liquid crystals, 40 wt % cholesteryl oleyl carbonate (COC), 40 wt % cholesteryl nonanoate (CN), and 20 wt % cholesteryl 2, 4-dichlorobenzoate (CD) encapsulated by thin PET film with black background provides temperature sensor that has red-start at 32° C., green-start at 33° C. and blue-start at 34° C. enables to detect the temperature from 31° C. to 37° C. (FIG. 24, panel b, and 25). Silver chloranilate immobilized in pHEMA produces purple colored ion from reaction with chloride ion sweat and the color level continuously decreases with chloride concentration that allow lightness (L) level to provide a representative number of the color of assay (FIG. 24, panel c). As the sweat continuously flows in the chamber, the color development has a chance to be sensitive to flow rate. Sufficient reaction time from long reaction area provides uniform color development independent of flow rate from 1 to 5 µL min$^{-1}$ (FIG. 26). Glucose in the sweat produces hydrogen peroxide ($H_2O_2$) from the enzymatic reaction with glucose oxidase and peroxidase reacts with glucose substrate dye using $H_2O_2$ results yellowish color that changes blue level in the chamber dominantly (FIG. 24, panel d). Universal pH dye provides a pH sensor and red level from the sensor that changes dominantly with pH of solution serve a comparing parameter for the color of assay (FIG. 24, panel e). Lactate assay follows the similar enzymatic reaction as glucose assay and produces red color at low concentration at 5 mM and yellow color from 15 mM. The green level changes dominantly and serves a representative color value from the assay (FIG. 24, panel f). For enhancement of the color difference between concentration that makes more accurate color detection, the channel depth makes a dominant effect because thicker chamber produces longer path length of light (FIG. 27). As the chamber thickness defines the total thickness of the device and volume of chamber, 600 µm thick chamber provides soft mechanics of device and appropriate volume of sweat into the device as ~6 µL.

Exemplary Colorimetric Assays:

1) chloride: 8 µL of mixture of 50 mg of silver chloranilate (MP Biomedicals, CA, USA) and 200 µL of 2% pHEMA provides assay for chloride detection.

2) glucose: 1.0 µL of buffer, 0.5 µL of substrate, 0.5 µL of enzyme located in a chamber developed color for glucose detection. (Glucose Colorimetric Assay Kit II; Biovision, CA, USA)

3) pH: pH cocktail solution was realized by thoroughly vortexing 4 mL of universal pH dye (Fisher Scientific, NH, USA), 274 mg of polyvinyl chloride (M.W. ~233,000, Sigma-Aldrich, MO, USA), 635 µL of o-nitrophenyloctylether (Sigma-Aldrich, MO, USA) and 508 µL of aliquot in 10 mL of tetrahydrofuran (Sigma-Aldrich, MO, USA) till a homogenous suspension was obtained. Thereafter, a filter paper was dipped in the cocktail solution for 10 s and allowed to dry at ambient conditions for 15 min to realize the solid-state pH assay. Finally, a metal punch (diameter, 2 mm) was used to excise circular pads of the pH assay paper for incorporating in the wearable patch.

4) lactate: the lactate assay cocktail was prepared by thoroughly mixing 17% v/v dye, 17% v/v peroxidase from horseradish (HRP) (20 mg/mL; Sigma-Aldrich, MO, USA) and 66% v/v lactate oxidase (LOx) (60 mg/mL, activity of 101 U/mg; Toyobo Corp., Osaka, Japan) solution. The dye solution was earlier prepared by mixing 0.5 M 3,5-dichloro-2-hydroxy-benzenesulfonic acid (Sigma-Aldrich, MO, USA) with 0.25 M 4-aminoantipyrine in 1:1 v/v ratio, while the enzyme and dye solutions were prepared in 0.1 M sodium phosphate buffer (pH 7.0) and deionized water respectively. The lactate assay spot was prepared by first coating 2 µL of lactate assay cocktail in the designated chamber of the patch and letting it dry. A second coat of 1.5 µL of enzyme solution containing HRP (20 mg/mL) and LOx (60 mg/mL) in 1:2 v/v ratio was applied to the assay spot to extend the detection range up to the physiologically relevant lactate concentration and to enhance the color contrast. The assay spot was allowed to dry for at 1 hour at ambient room temperature before utilizing if for lactate detection.

Exemplary Colorimetric Temperature Sensor:

A thermochromic liquid crustal is fully sterol-based ternary mixture containing 20 wt % cholesteryl oleyl carbonate (COC, Sigma-Aldrich, MO, USA), 40 wt % cholesteryl nonanoate (CN, Sigma-Aldrich, MO, USA), and 20 wt % cholesteryl 2, 4-dichlorobenzoate (CD, Pressure Chemical Company, PA, USA). The mixture was heated at 200° C. with magnetic stirrer until forming a homogeneous mixture and was applied on the PET film with printing black for background and covered by another PET film. A $CO_2$ laser (Universal Laser Systems, AZ, USA) defined the size of the TLC film as 2.5 mm in diameter.

Exemplary Standard Color Development and Color Reference Marker Preparation:

Sodium chloride, D(+) Glucose and L(+) lactic acid (Sigma-Aldrich, MO, USA) generated standard solutions in DI water as its concentrations. Mixing 0.2 M sodium phosphate and 0.1 M citric acid produced pH buffer solutions from pH 4.5 to 7.0 and pH meter (Mettler Toledo, Greifensee, Switzerland) was used to measure pH. A syringe pump (Harvard Apparatus, MA, USA) generated flow at 1 µL/min speed into the microfluidic device with chloride assay on the hot plate at 31° C. until the solution filled 20% of the channel. For glucose, lactate and pH test, pipetting flowed standard solution into the chambers. For full color development, the device with glucose and lactate assay filled by the solution stayed on the hot plate at 31° C. for 20 min and pH for 5 min. A digital SLR camera (EOS 6D; Canon, Tokyo, Japan) took the picture of the device. Photoshop (Adobe Systems, CA, USA) provided color extraction from the color in the chambers. A color laser printer (C454 PS; Konica Minolta, Tokyo, Japan) produced a reference maker on PET film at 1200 DPI resolution. The printed the reference marker placed on the device again and smartphone camera (Iphone 5s; Apple, CA, USA) took picture of the chamber with reference marker. The color analysis compared the color level from the chamber and reference marker. Three spots from each chamber and reference marker provided the average color value. By adjusting brightness of the image, repetition of printing and comparing provided the optimum reference marker. For in vitro accuracy test, the color developed device with reference marker placed in laboratory with white light bulb and yellow light bulb and in outdoor.

Exemplary Accuracy Test of Colorimetric Methods in Various Lighting Condition:

The absolute color value from the image of assay chamber changes according to the lighting condition. The color reference marker attached to the device around the assay chamber represents color value of specific concentration and changes its color according to the lighting condition, thereby providing accurate color evaluation regardless of lighting condition. For validation of the functionality and accuracy of colorimetric method coupled with color reference marker, the devices supplied with known standard concentration produces images in white light bulb, yellow light bulb and daylight condition (FIG. 28, panel a). Overall the accuracy of chloride, glucose, pH and lactate are about 5%, 10%, 2%, 10% of testing concentration, respectively (Table 2).

The type of lighting condition does not affect to the size of accuracy in general. In case of pH and lactate, daylight condition may produce lower estimated concentration than expected concentration.

TABLE 2

Accuracy of colorimetric method

| Concentrations (mM) | | | | |
|---|---|---|---|---|
| Chloride | 25 | 50 | 75 | 100 |
| White bulb | 23 | 48 | 78 | 101 |
| S.D. | 2 | 1 | 4 | 3 |
| Yellow bulb | 23 | 50 | 76 | 97 |
| S.D. | 3 | 1 | 1 | 1 |
| Daylight | 25 | 50 | 80 | 102 |
| S.D. | 1 | 0 | 3 | 5 |

| Concentrations ($\mu$M) | | | | |
|---|---|---|---|---|
| Glucose | 25 | 50 | 75 | 100 |
| White bulb | 20 | 53 | 82 | 101 |
| S.D. | 4 | 4 | 2 | 9 |
| Yellow bulb | 23 | 52 | 80 | 106 |
| S.D. | 6 | 2 | 3 | 5 |
| Daylight | 21 | 52 | 73 | 104 |
| S.D. | 5 | 1 | 2 | 5 |

| pH | | | | |
|---|---|---|---|---|
| pH | 5.0 | 5.5 | 6.0 | 6.5 |
| White bulb | 4.9 | 5.5 | 6.0 | 6.5 |
| S.D. | 0.1 | 0.0 | 0.0 | 0.1 |
| Yellow bulb | 5.0 | 5.6 | 6.1 | 6.6 |
| S.D. | 0.1 | 0.0 | 0.1 | 0.1 |
| Daylight | 4.9 | 5.6 | 6.0 | 6.5 |
| S.D. | 0.1 | 0.0 | 0.1 | 0.1 |

| Concentrations (mM) | | | | |
|---|---|---|---|---|
| Lactate | 5 | 10 | 15 | 20 |
| White bulb | 5.7 | 10.4 | 14.8 | 19.3 |
| S.D. | 0.4 | 0.4 | 0.3 | 1.1 |
| Yellow bulb | 5.9 | 10.3 | 14.9 | 20.1 |
| S.D. | 0.3 | 0.5 | 1.2 | 2.2 |
| Daylight | 4.6 | 9.4 | 13.4 | 18.4 |
| S.D. | 0.8 | 0.5 | 0.2 | 1.4 |

| Temperature | | | | | |
|---|---|---|---|---|---|
| Temp (° C.) | 37 | 36 | 35 | 34 | 33 | 32 |
| White bulb | 370 | 36.1 | 34.8 | 34.0 | 33.0 | 32.0 |
| S.D. | 0.03 | 0.04 | 0.14 | 0.02 | 0.13 | 0.03 |
| Yellow bulb | 37.1 | 36.2 | 34.9 | 33.9 | 33.0 | 32.0 |
| S.D. | 0.03 | 0.26 | 0.11 | 0.22 | 0.06 | 0.10 |
| Daylight | 36.8 | 36.2 | 35.0 | 34.0 | 33.1 | 31.9 |
| S.D. | 0.06 | 0.09 | 0.33 | 0.11 | 0.00 | 0.00 |

Example 7: Epidermal Microfluidic Sensor for Sweat Collection and Analysis from Aquatic Athletes Waterproof NFC electronics comprise a flexible magnetic loop antenna, a set of near-field communication (NFC) components, and an LED as a mode for user notification form a wireless interface to NFC-enabled devices (smartphones, tablets, etc) for transmitting a digital identification code and a reading of skin temperature. Exemplary details on the processes for fabricating the NFC coil and on the circuit designs are includes in other Examples (e.g., Examples 3 and 4) and an exemplary NFC coil and associated components are illustrated in FIGS. 29 and 30. A coating of SIS encapsulates the NFC electronics to allow robust operation for extended periods even when completely submerged in water (FIG. 29, panel C). FIG. 29, panel E, illustrates the wireless operation of the NFC electronics in a wet environment and shows the LED as it emits light through the microfluidic layers.

Example 8: A "Skin-Like" Wearable Microfluidic Sensor for Fluorometric Sweat Analysis Layer Structured Microfluidic System for Fluorometric Assays:

A fluorometric sweat-sensing system consisting of a wearable microfluidic device and a smartphone-based fluorescence-imaging device to analyze biomarkers in sweat in-situ with a simple procedure and high sensitivity. Microfluidic device composed of a multilayer stack of three subsystems: an adhesive membrane, a sealed microfluidic channel and reservoirs, and a detachable black light-shielding film provides a reaction chamber to analyze various biomarkers by fluorometric methods. The micro-patterns in the fluidic layer enable use of fluorometric assays and simple sweat loss monitoring. FIG. 31 shows the features of a microfluidic device for fluorometric sweat sensing. The diameter and total thickness of the device are 32 mm and ~2 mm, respectively. Three independent assays are designed along the inside of the round layer each with its own inlet hole with diameter of 0.3-1.5 mm and connected three micro-reservoirs, respectively. The channel widths and depths are 100-200 μm and ~400 μm, respectively, and the diameter of each reservoir is 2.64 mm. The micro-reservoirs are connected by the curved channels with capillary bursting valves (CBVs). The valves enable time-sequential sweat sampling with three intervals for each reservoir. FIG. 32 shows a set of CBVs in the chamber. CBV #1 has 50 μm wide channel with 123°, CBV #2 has 160 μm wide channel with 23°, CBV #3 has 150 μm wide channel with 85° of diverging outlet, respectively. Sweat first burst CBV #2 and fills the chamber #1. Then, CBV #3 with highest BP blocks the sweat flow. After filling chamber #1, sweat burst CBV #3 and flows to the next chambers. The assay reservoir having three assay chambers can store a total of 8.1 μL of sweat, with ~2 μL for each chamber. The two round reservoirs located between the assay systems were designed for a fluorescence reference system composed of ionic liquid and a fluorescence dye.

The doughnut-shaped black PDMS with 200 μm thickness placed on top of the device work as a light shield to prevent photobleaching of the fluorescence reagents while collecting sweat. The low elastic module (~145 kPa) and surface adhesion property of the PDMS allowed for detachable adhesion between the PDMS films without any treatment. The PDMS-PDMS adhesion could be detached easily by figures (FIG. 31 (panel c)). The flower-shaped channel designed in the center of the layer allows the device to indicate sweat loss for the fluorometric assays. The incoming sweat dissolves the water-soluble dye located near the inlet as it flows past, thereby creating a visible, colored fluid with an easily identifiable filling front in the channel. Since the channel volume (~8.1 μL) is designed to be almost equal to that of an assay system (~8.1 μL), the channel system can indicate the amount of sweat filling the fluorometric assay reservoirs, which are normally shielded by the black film. The low modulus and high elasticity (up to ~200%) of PDMS enabled soft and flexible devices, which are suitable as a skin wearable sensing system. FIG. 31 (panel d) shows deformation of a representative device by bending and twisting. The device exhibited excellent strength properties against various mechanical forces and distortions and can be applied to the skin on any part of the human body.

Exemplary Device Fabrication Protocols:

Soft lithographic techniques yielded the microfluidic silicon molds. Patterning photo-resist of KMPR 1010 (Microchem, MA, USA) on 1 mm thick Si-wafer and deep reactive ion etching (STS Pegasus ICP-DRIE; SPTS Technologies, Newport, United Kingdom) generated a mold for microfluidic channel. Thin layer of poly(methylmethacrylate) (PMMA; Microchem, MA, USA) formed on the mold. Pouring 10:1 PDMS (Sylgard 184; Dow corning, MI, USA) mixed with white silicone dye (Silc Pig; Smooth-on, Inc., PA, USA) at 10% wt on the mold and spin coating at 150 rpm with baking at 150° C. for 30 min yielded a 1 mm thick layer. All the chemical assays were located on the cured PDMS channel. Mechanical punches were used to cut out a round-shaped patch and to create inlet holes for collecting sweat. A transparent PDMS mixture in a ratio of 10:1 (rubber base:cure) casted on a PMMA coated flat wafer at 300 rpm and cured 150° C. for 30 min formed a uniform cover layer. Bonding the cover film to the white microfluidic channel film after placing fluorometric assays defined sealed microfluidic channels and assay chambers. A tiny amount of PDMS (10:1) was applied on the cover film before stacking on top of the channel layer, and then cured at 40° C. for 1 h. The process allowed efficient bonding of the stack without damage of the assay reagents. Casting a PDMS mixture containing a black silicone (Silc Pig; Smooth-on, Inc., PA, USA) in a ratio of 10:1:1 (rubber base:cure:black silicone) at 200 rpm and cured at 150° C. for 30 min yielded a uniformly black elastic film. The black cover film was placed on the top of the stack without any bonding agents to yield a detachable light shield. A $CO_2$ laser (Universal Laser Systems, AZ, USA) cut a double-sided skin adhesive membrane (PC2723U; ScapaHealthcare, CT, USA) into a round shape with defined sweat inlet holes. The adhesive membrane with matching inlet holes was bonded to the bottom surface of the PDMS device on one side and to the skin on the other side. Plasma treating the micro microfluidic layer with a corona generator (Electro-Technic Products, IL, USA) created hydrophilic surfaces on the PDMS that allowed efficient bonding of the PDMS layer and the adhesive.

A Smartphone-Based Fluorometric Imaging System Applicable for a Sweat Sensing Device:

A smartphone system yields fluorescence sweat sensing in-situ with microfluidic devices. FIG. 33 (panel a) illustrates the features of a smartphone-based fluorescence imaging system consisting of a normal smartphone attached to an accessory. The attachment involving a dark shield box with immobilized excitation and emission filters allows a normal smartphone to take fluorescence images using its camera function. The attachment includes two movable parts: one is for fixing the holder to the side of a smartphone, and the other is for adjusting the box position to make contact with the excitation and emission filters and the interfaced smartphone LED light and camera (FIG. 33 (panel b)). The filters allowed the LED light and camera to work as an excitation light and a detector for fluorescence signals (FIG. 33 (panel c)). The blue transparent films that are generally used for display enabled transmittance of only blue light with narrow wavelength (451±35 nm) (FIG. 33 (panel d)) from the smartphone LED light (400 nm-750 nm wavelength, FIG. 33 (panel f)). The transmitted blue light allows the fluorescent probes (excitation wavelength of 400 nm-530 nm) on the patch to be excited. To detect only the emitted fluorescence signal, a long-wave pass glass lens that can blocks light below 515 nm wavelengths was placed at the interface of the smartphone camera lens. Double green filters also provide green light with narrow wavelength (550±50 nm) from the smartphone LED light (FIG. 33 (panel e)). It means various excitation lights can be obtained from filtered smartphone LED light.

FIG. 34 (panel a) shows a procedure of fluorescence sweat sensing using the microfluidic device and the smartphone-based system. The skin-mounted microfluidic device introduced sweat from the co-glands to the flower-shaped channel and the three independent assay parts through the corresponding inlet holes (FIG. 34 (panel a)-1). Completely filling the flower-shaped channel with the blue-colored sweat fluid indicates that the three assay reservoirs might be full. Then, the uppermost black film could be detached for taking a picture by the smartphone system (FIG. 34 (panel a)-2). Taking a picture with flashlight using the smartphone with the attachment provided a fluorescence image of the signals on the device (FIG. 34 (panel a)-3). PDMS that is transparent for wide range of wavelength and has a low refractive index (around 1.41) is applicable for fluorescence analysis.

The fluorescence signal intensity depends on the concentration of targets. To calibrate the fluorescence signals, the intensity analyzed by Image J software (NIH, USA) was divided by the reference intensity (FIG. 34 (panel b)). A stable fluorescence dye dissolved in ionic liquid was pre-placed as a reference in the device. The reference marker should have almost same excitation wavelength to those of probes. Nonvolatile ionic liquid enabled placement of the reference dye in vapors permeate PDMS stably. Various fluorescence colored references are prepared by using ionic liquid and dyes.

In addition, a white sweat device played an important role for enhancement of the fluorescence signals due to reflection of emitting fluorescence by titanium oxide particles of white pigments on the curvature of the micro reservoir (FIG. 35).

Exemplary Device Fabrication Protocols:

Assembly of black acrylic pieces (McMaster-Carr, IL, USA), excitation (Scotchcal™ graphic film, 3632-87; 3M, MN, USA) emission filters (colored-glass alternative filter, 5CGA-515, Newport Co., CA, USA), and a commercial smartphone holder (Lotus Tech, Wembley, UK) part using glue yielded a smartphone-based fluorometric-imaging device. The $CO_2$ laser cut an acrylic black board with 3.18 mm into eight pieces. Gluing the four black plates together formed a square shaped box. Placing square plates with two holes for excitation and emission filters on the top of the box defined the light-shielding box. The excitation and emission filters were fixed to the holes of the plate. The box was attached to the smartphone holder by a long rectangular acrylic piece with a screw. For alignment of the sweat patch, a square plate having a hole with a size equivalent to that of the patch was placed on the bottom of the box. Putting pieces of black paper on the surface of the plates inside the box to prevent light reflection completed the assembly process. All the results of the fluorescence images were taken by using a smartphone, iPhone 6 Plus (Apple Inc., CA, USA).

Reference Marker:

Dissolving 0.4 mg of rhodamine 110 chloride (Sigma-Aldrich, MO, USA) in 2 mL of 1-ethyl-3-methylilimidazolium ethyl sulfate ionic liquid (Sigma-Aldrich, MO, USA) formed the green reference solution. Drop casting 0.5 μL of the ionic liquid dye onto the chambers designed for the reference fluorometric dye completed the process. Dissolving 0.4 mg of rhodamine Red-X (Thermo Fisher, USA) in 2 mL of 1-ethyl-3-methylilimidazolium ethyl sulfate ionic liquid formed the red reference solution.

Fluorometric Development:

Dropping assay solution onto respective chambers of a microfluidic layer, and then drying at 35° C. for 1 h in a light shielded environment yields a solid-state fluorometric assay for various biomarkers. FIG. 36 (panel a) shows the assay chambers for chloride, sodium, and zinc before and after filling sweat under visible light. The fluorescence probes installed in each reservoir are easily dissolved by incoming sweat and reacted with their targets, chloride, sodium, and zinc selectivity. FIG. 36 (panel b), (panel c), and (panel d) shows the variation of the fluorescence images of chloride, zinc, and sodium probes reacted with artificial sweat at pH 6 containing various concentration of the targets under the excitation light of the smartphone. The graphs below the images show the dependence of the normalized intensity on the concentrations of the targets. The standard curves worked for calculating the concentration of the targets on a human trial. The calculated values were comparable with the values measured by the traditional methods, ion chromatography for chloride, ICP-MS for zinc, and atomic absorption for sodium (FIG. 37). The fluorometric assay works even in use of an extremely small amount of sweat. FIG. 38 shows the result of fluorometric chloride assay using 0.3 µL artificial sweat containing with 0 to 150 mM chloride. Lucigenin was placed in a microfluidic device using supporting papers.

Fluorometric Assays:

The chloride fluorometric assay solution consists of 2 mg lucigenin (Sigma-Aldrich, MO, USA) dispersed in 1 mL of MilliQ water. The zinc fluorometric assay solution was prepared by adding 25 µL of zinc detector (Zinc Quantification Kit (Fluorometric), Abcam Inc., MA, USA) into 5 mL of the zinc assay buffer. Dissolving 1 mg of the sodium detector (CoroNa™ Green; Molecular Probes, OR, USA) in 100 mL of dimethyl sulfoxide (Sigma-Aldrich, MO, USA) yielded a concentrated solution. Dispersing 2.3 µL of the concentrated solution into 1 mL of MilliQ water yielded the sodium fluorometric assay solution at the concentration of 40 µM. Dropping 2 µL volume of each assay solution onto the respective chambers of the microfluidic layer, and then drying at 35° C. for 1 h in a light shielded environment yielded the solid-state chloride, zinc, and sodium assays, respectively.

Example 9: Method to Improve Accuracy of Colorimetric Assay Analysis

Accuracy of colorimetric assays suffer in response to effects such as subtle color changes between different states (e.g. difference between 5 mM and 10 mM chloride levels), non-uniform lighting conditions, channel height, or variations in printed calibration marks (e.g. resolution, ink concentration, color print space). Whereas sampling colors in a device-independent color space, such as CIE L*a*b* color space, provides a facile method for color comparison, many colorimetric assays (such as chloride) contain a "white point measurement" indicating the absence of an analyte (i.e. 0 mM chloride). The utilization of white in a colorimetric assay is problematic when attempting to distinguish between subtle variations in color and thus analyte concentration as white is defined as $L^*=100$, $a^*=0$, $b^*=0$. Luminance, $L^*$, is most prone to variations in illumination, which propagates uncertainty into colorimetric assay analysis at low concentrations. For clinical applications, maximizing accuracy at low concentrations, which for chloride is <45 mM, is necessary to establish the assay as comparable to a diagnostic gold standard (e.g. chloride value <=1 mM standard deviation).

A flatbed scanner (Canon CanoScan LiDE 220) is used to eliminate variations in lighting. Illumination uniformity can be determined via a pixel-by-pixel variation analysis of each channel (RGB) of a full-bed scan. Typical variation was found to be <0.8% across the entire bed with <0.1% variation across a 30 mm×60 mm region (size of a test sweat device).

One strategy to improve colorimetric assay accuracy is to eliminate the white point in an assay by overprinting the measurement region with a contrasting color. By overprinting, the relevant detection range of the assay is elongated to increase the range of distinguishable color measurements. A demonstration of this strategy appears in FIG. 39.

Although several methods exist to relate measured differences in color in CIE $L^*a^*b^*$ space to assay concentration, accuracy is maximized while minimizing external factors (such as luminance variation) by using the established value for chroma (C) which is related to the $a^*$ and $b^*$ coordinates via the relationship $C=(a^{*2}+b^{*2})^{(1/2)}$. Using chroma, independent of $L^*$, to map measured color to known analyte concentration establishes a calibration curve to measure unknown solutions. Identifying the optimal color for a particular colorimetric assay is rapidly ascertained via a facet plot of the different variables so as to identify the parameters that provide a linear fit with the best fit and the largest gradient (i.e. slope) as compared to the control points. An example of the facet plot appears in FIG. 40 for the Green color shown in FIG. 39.

A comparison of color overlays generated via an inkjet printer and a laser printer show minimal influence on the performance of a selected color.

After the identification of an optimized color and opacity for a given assay, comparison of the calibration curve to an "unknown" calibration sample provides a simple means for evaluating accuracy. For silver chloranilate assay for chloride samples in a diagnostically relevant range (10 mM to 75 mM), the best-fit regression equation has been determined to be a power-law fit. The $R^2$ values for control is 0.995 and for the green-color overlay 0.999 for the values provided in Table 3. Evaluating the calibration curve at the measured chroma values for 30 mM (not part of fit calculations), the control yields a concentration measurement of 25.7 mM, within the expected range of a colorimetric assay. However, when measured with a color overlay, the fit yields a concentration of 30.41 mM. The calibration solution, when measured using a chloridometer (clinical gold standard, Wescor Chlorochek), is 30.5 mM (N=3, resolution is ±1 mM).

TABLE 3

Measured chroma values for a control (no overlay) and green overlay for silver chloranilate chloride assay at given chloride concentrations. 30 mM represents the calibration solution that is used to check the goodness of fit and compare performance accuracy.

| | Chroma | |
| --- | --- | --- |
| Concentration (mM) | Control | Green Overlay |
| 10 | 7.07 | 53.15 |
| 25 | 11.66 | 48.09 |
| 50 | 20.62 | 40.02 |
| 75 | 25.81 | 33.12 |
| Calibration: 30 | 12.81 | 46.20 |

Example 10: Integrating Structural Features for Rapid Volume Readout

The planar microfluidic channels can be designed so that the method of filling provides information about the performance of the device. One example is the use of filling behavior in a spiral to indicate the fill percentage of a channel "reservoir" of a known volume. As shown in FIG. 41, a channel "reservoir" may hold a total volume of 5 µL. The feature fills continuously but when half full (2.5 µL) the direction of filling switches. Using both motion and geometry, a person wearing the device can quickly monitor the collected sweat volume. As the sweat fills the device continuously, approximate percentages (such as ⅔ and ¾) are also easily assessed. When combined into a series of reservoirs, larger volumes of sweat can be quickly measured during a collection period as shown in FIG. 42.

Example 11: Integrating Passive Optical Elements to Visualize Sweat Filling

Visualization of sweat filling a sampling device is important for both evaluating device performance and for recording physiological data such as sweat rate. However, if the sweat is to be extracted for external analysis, the presence of dyes may be undesirable due to the possible contamination of other biomarkers present in sweat. We demonstrate the integration of passive optical elements and structural changes to the microfluidic channels that provide contrast to visualize the presence or absence of sweat without the need for pigments/dyes. FIG. 43 demonstrates three examples of lenses/retroreflector structures embedded in the soft polymer channels in the absence (FIG. 43, panel A) and presence of sweat (FIG. 43, panel B), a patterned area of surface roughness on the channel in the absence (FIG. 43, panel C) and presence of sweat (FIG. 43, panel D), and an embedded layer of microspherical silica particles which are opaque in the absence of sweat (FIG. 43, panel E) and become transparent in the presence of sweat (FIG. 43, panel F) revealing a color underlay.

An important component is the direct integration of structural features such as (a) lenses (b) surface roughness or (c) inert micro/nanoparticles into the channel surfaces exposed to sweat that cause a change in the index of refraction between a channel filled with air and that with sweat (water). The structural color change (FIG. 43, panels E, F) can be magnified if the underlying channel color is itself different from the surrounding medium but obscured via the structural feature. This provides enhanced visualization independent of viewing angle. Although the lens structure is molded into the channel (FIG. 43, panels A, B), the channel itself can act as a lens when filled with air, magnifying an image underneath the channel. When filled with sweat (or water), the lens is eliminated due to the matching of the index of the surrounding silicone material thus obscuring (or revealing) the pattern underneath the channel.

Example 12: Epidermal Microfluidic Sensor for Sweat Collection and Analysis from Aquatic Athletes Measurements of Sweat Loss and Instantaneous Sweat Loss:

The serpentine microfluidic channel has capability to measure sweat rate over a local region (e.g., anterior forearm) during cycling, and to correlate this measure with the total body sweat loss (FIG. 44, panel a). The simple microfluidic device with colored dye in the channel shows the filling of the sweat from the skin (FIG. 44, panel b). The comparison of the sweat collection from the microfluidic device with total body loss which measured by weighing body weight before and after exercise without water consumption shows good correlation (FIG. 44, panel c), indicating that microfluidic devices could be used to estimate total body loss in ambulatory environments. The amount of sweat captured with the microfluidic device and the control method using fabric based skin patch (Tegaderm® absorbent pad) also shows good correlation (FIG. 44, panel d). Furthermore, microfluidic devices enable immediate measurement of sweat rates during exercise routines. FIG. 44, panel e, shows immediate sweat rates at three different intervals in time. During the first session of exercise (labeled 'exercise'), there is constant sweat rate followed by a decrease in sweat rate approaching zero sweating when the subject is at rest (labeled 'rest'). The immediate sweat rate returns to initial levels once the subject re-initiates physical exertion (labeled 'resumed exercise').

Control Sweat Collection and Total Body Loss Measurement:

Subjects performed exercise on standing bicycle for 20-90 min with no fluid intake or restroom use during exercise. Tegaderm® with pad (3582; 3M, MN, USA) provided a control method to measure sweat generation at defined region. After collecting the sweat from the skin, the sweat weight was calculated by subtracting the initial mass of the Tegaderm®. Weighing by digital scale (Adam Equipment, CT, USA) with 2 g accuracy before and after exercise in nude provided the data for calculating total body loss.

Example 13: Battery-Free Near-Field Communication-Based Soft, Wearable Microfluidic Sweat Sensors: Battery-Free, Skin-Interfaced Microfluidic/Electronic Systems for Simultaneous Electrochemical, Colorimetric and Volumetric Analysis of Sweat Field testing involves healthy, non-diabetic, human subject volunteers (three males) instrumented with devices on the upper wrist. Studies follow guidelines laid down by the Institutional Review Board, Northwestern University, for studies with human subjects. The physical exercise involves cycling on a stationary bike with increasing resistance. Real-time data acquisition during each trial occurs either through a compact, short-range reader, or an extended, long-range reader were positioned in the vicinity of the device. As illustrated in FIG. 10 (panels G and H) and FIG. 14, the long-range reader offers significant spatial latitude to the user during data collection. FIG. 45, panel A, displays an image of a subject on a stationary bike wearing the patch, with an extended antenna (60×30 $cm^2$) in the background. FIG. 45, panel B, summarizes the effective communication distance between the device and antenna (shown in FIG. 45, panel A), presented here is the largest distance that enables successful operation. The data shows a maximum operating distance of 18 cm with this configuration.

FIG. 45 (panels C-E) shows a device after cycling, along with a summary of data acquired from the lactate and glucose sensors. Similarly, FIG. 45 (panels F-H) presents images of the device for another subject, illustrating lactate and glucose sensor measurements. For both subjects, the respective electrochemical sensors produce voltage signals that yield corresponding concentrations based on calibration plots obtained at ~30° C. (usual sweat temperature). The measured analyte concentrations are consistent with those of other Examples. Image analysis of FIG. 45 (panels C and F) reveals that the concentration of chloride is 34±2 mM (subject #1; chamber #1) and 62±5 mM (subject #2; chamber #1) and 36±5 mM (subject #2; chamber #2); the pH is 6.4±0.1 (subject #1; chamber #1) and 6.3±0.1 (subject #2; chamber #1) and the sweat rate is ~0.52 µL/min (subject #1) and 0.88 µL/min (subject #2). Separate analyses using conventional techniques such as commercial bench-top chloridometry, pH analysis and high-resolution nuclear magnetic resonance (NMR) spectroscopy provide points of comparison. Table 1 summarizes the results. FIG. 45, panel I, illustrates capabilities in monitoring of glucose and lactate levels in sweat over multiple days for subject #1. See FIG. 46 for data from an additional two subjects (subject #2 and #3). Separate measurements capture blood lactate and glucose levels over the same time period, as points of comparison. In these studies, the subjects wear sensors on the upper wrist for two consecutive days. On each day, the subject performs a cycling exercise on a stationary bike once in the morning in a fasting state, 20 min after consuming a sweetened drink containing 150 g of sugar and then again in the evening. Blood tests with commercial blood lactate (Lactate Plus®, Nova Biomedical, MA) and blood glucose (Accu-Check® Nano meter, Roche Diabetes Care, Inc.) meters capture the concentrations of these analytes before and after each cycling event. Photos of the device at different stages of the study, as shown in FIG. 45, panel I, and FIG. 46, indicate robust adhesion to the skin throughout the study. Analysis of the data reveals that the blood levels after each session follow trends that are similar to those of data measured on sweat using the skin-interfaced devices. These findings are generally in agreement with those of previous studies that compare lactate and glucose levels in blood to those measured in sweat using conventional collection and ex-situ analysis techniques. Further support for the long-term stability of the sensors follows from comparisons of signals produced by a pair of devices after the two-day trial with an unused pair (FIG. 47). The data show that the performance of the glucose sensor remains unchanged while the response of the lactate sensor decreases by only ~20% even after these rigorous two-day trials. These results represent the first examples of long-term use of skin-interfaced sweat sensors. The outcomes provide for non-invasive tracking of blood glucose and lactate levels. A second set of studies focus on exploring temporal variations in sweat glucose and lactate as compared to those of blood due to consumption of food and engagement in physical exercise. Here, the subjects wear the patch for one day and perform a cycling exercise (15-20 min) on a stationary bike in the morning in a fasting state, 30 min and 90 min after consuming breakfast and then again 30 min before lunch and 30 min and 90 min after lunch. Blood tests are performed using protocols similar to those for the first set of studies. FIG. 48 shows data acquired for subject #1 and #2 during these long-term sweat monitoring. Analysis reveals that the blood levels after each session follow trends that are similar to those of data measured on sweat using the skin-interfaced devices. The sweat glucose values lag behind those acquired from blood tests by ~30-60 min, while a much smaller time lag exists between blood lactate and sweat lactate. Such time lags can attributed to complex biological pathways through which the blood constituents reach other biofluids.

Example 14: Battery Free NFC Based Soft Microfluidics to Readout Sweat Excretion Rate Using the system packaged, human tests were conducted. FIG. 49, panel a shows the device can be mounted on various location of the subject body. The human tests were conducted to show the difference of sweat rate in the thermal environment (FIG. 49, panel b) and exercise environment (FIG. 49, panel c). Also in the exercise test, two locations on the bodies were compared. Subject #1 and #2 were tested and both showed the chloride and sweat rate were higher at running condition. The correlation of sweat rate and chloride concentration was also allowed as reported by Smith et al. in 2011 and Taylor et al. in 2013. Also other four subjects (FIG. 49, panels f-i) were tested to see the difference of sweat rate for forehead and forearm. Forehead is known to be a location which has most dense sweat gland, and generally shows high sweat excretion rate and pressure. And four subjects show similar results and sweat excretion trend.

For human test, six healthy volunteers were involved in the on-body test with jogging and operating stationary bike indoors with 73% humidity and 25° C. temperature condition. The devices were placed on fore head, chest, lower back, and fore arm. Before mounting the device, the skin has cleaned with 70% methyl alcohol. In the process of human test, there was no drinking water for hydration. All subjects were noticed about the procedure of human test.

Example 15: Capacitive-Based Sensors for Characterization of Sweat Rate and Sweat Dielectric Properties in Microfluidics Sweat Collection Patches Analysis of sweat rate as well as sweat composition contains useful health diagnosis information that can be collected in a non-invasive way, using a soft interfacing to the skin via microfluidics sweat collection patches. Measuring continuously the local sweat rate could provide health information and be used in various contexts, including for instance the study of diseases providing asymmetrical sweating (e.g., stroke rehabilitation). Sweat composition analysis techniques on microfluidics devices may include colorimetric or electrochemical sensors, but here we develop a method based on the analysis of dielectric properties of sweat, that can be done without the use of any reagent. Indeed, we can quantify sweat rate and sweat dielectric properties using capacitive techniques, that include some non-contact techniques which do not imply any reaction and any contact between sweat and electrodes.

The design of this device involving a unique combination of microfluidics, capacitive sensors, and near-field or Bluetooth communication will comprise the following parts: (1) A microfluidics platform; (2) Metal electrodes; (3) NFC or Bluetooth transmission platform.

More precisely, three techniques are envisioned for capacitive measurements: (i) Using two interdigitated metal electrodes to sense sweat without contact. The electrodes would be separated from the microfluidic channel by a thin dielectric layer. (ii) Using one metal electrode, the second electrode being in contact with sweat that is used as a conductor. A dielectric would separate the metal electrode from the sweat electrode. (iii) Using two metal electrodes, one on top and one on the bottom of the microfluidics platform.

With the technique (i), the sweat collection platform could be divided into two parts: (a) one re-usable electronics platform, laminated on (b) one single-use sweat collection microfluidics platform.

Sensing dielectric properties of a liquid can be done in a non-invasive way, involving no chemical reaction and no contact with the liquid. The dielectric properties of sweat may be characterized via a frequency sweep, to extract the most from this non-contact technique.

Exemplary Device Fabrication:

Microfluidics. The fabrication of the microfluidic platform begins by the manufacturing of an appropriate mold, using a silicone wafer, spin coating and baking a thick layer of photoresist, patterning with photolithography techniques and using deep reactive ion etching. The mold is then covered with a thin layer of poly(methylmethacrylate) and used to cast silicone elastomer. This step allows to create one layer of elastomer that needs to be bonded to a capping layer to form microfluidics channels.

Electrodes. Electrodes are made using a combination of the following materials: polyimide, PDMS or other silicone elastomer, Chromium, Copper, Gold, Titanium, $SiO_2$, making use of clean-room processing techniques and/or laser patterning.

Dielectric layer. Different materials are envisioned, including silicone elastomers, polyimide, $SiO_2$, and adhesives (acrylic or silicone-based).

NFC or Bluetooth electronics may be formed in accordance with above Examples.

FIG. 50: Exploded illustration of one possible composition of a device involving interdigitated electrodes (technique (i)). Interdigitated electrodes would be connected to a NFC or bluetooth capacitance measurement and transmission platform. A frequency sweep could be applied to obtain dielectric spectroscopy data. The electrodes are separated from the microfluidics channel by a thin dielectric layer (thickness below 100 microns). The microfluidics platform can be separated from the skin with a second dielectric layer and adhesive to stick to the skin. An inlet allows filling of the microfluidics platform.

FIG. 51: Exploded illustration of an example of a configuration where sweat could be used as a conductor, to quantify sweat rate, referred to as technique (ii) in the text.

FIG. 52: Exploded illustration of an example of a configuration where two electrodes could be used on top and on the bottom of the microfluidics channels, referred to as technique (iii) in the text.

STATEMENTS REGARDING INCORPORATION BY REFERENCE AND VARIATIONS

All references throughout this application, for example patent documents including issued or granted patents or equivalents; patent application publications; and non-patent literature documents or other source material are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention. The specific embodiments provided herein are examples of useful embodiments of the present invention and it will be apparent to one skilled in the art that the present invention may be carried out using a large number of variations of the devices, device components, methods and steps set forth in the present description. As will be obvious to one of skill in the art, methods and devices useful for the present embodiments can include a large number of optional device components, compositions, materials, combinations and processing elements and steps.

Every device, system, combination of components or method described or exemplified herein can be used to practice the invention, unless otherwise stated.

When a group of substituents is disclosed herein, it is understood that all individual members of that group and all subgroups, including any device components, combinations, materials and/or compositions of the group members, are disclosed separately. When a Markush group or other grouping is used herein, all individual members of the group and all combinations and subcombinations possible of the group are intended to be individually included in the disclosure.

Whenever a range is given in the specification, for example, a number range, a temperature range, a time range, a net bending stiffness range, a volume range, a footprint area range, a size range (such as thickness, width and/or length) or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements and/or limitation or limitations, which are not specifically disclosed herein.

One of ordinary skill in the art will appreciate that compositions, materials, components, methods and/or processing steps other than those specifically exemplified can be employed in the practice of the invention without resort to undue experimentation. All art-known functional equivalents, of any such compositions, materials, components, methods and/or processing steps are intended to be included in this invention. The terms and expressions which have been employed are used as terms of description and not of limitation, and there is no intention in the use of such terms and expressions of excluding any equivalents of the features shown and described or portions thereof, but it is recognized that various modifications are within the scope of the invention claimed. Thus, it should be understood that although the present invention has been specifically disclosed by exemplary embodiments and optional features, modification and variation of the concepts herein disclosed may be resorted to by those skilled in the art, and that such modifications and variations are considered to be within the scope of this invention as defined by the appended claims.

It must be noted that as used herein and in the appended claims, the singular forms "a", "an", and "the" include plural reference unless the context clearly dictates otherwise. Thus, for example, reference to "a layer" includes a plurality of layers and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described.

We claim:

1. A microfluidic system for monitoring a biofluid, comprising:
   a flexible substrate;
   a microfluidic network at least partially embedded in or supported by the substrate;
   a biofluid inlet fluidically connected to said microfluidic network to transport a biofluid from a skin surface to said microfluidic network;
   an optical sensor supported by the substrate and configured to sense one or more parameters of said biofluid or a component thereof, said optical sensor including one or more integrated optical structures, wherein said optical sensor comprises a colorimetric sensor, and
   a near-field communication (NFC) electronics module operably connected to support wireless power delivery, wireless data transmission or both to said system.

2. The system of claim 1, wherein said biofluid is sweat or a component thereof from a subject.

3. The system of claim 1, wherein said one or more integrated optical structures are one or more lenses, lens arrays, filters, optical gratings, reflectors, optical sources, optical detectors, retroreflectors, pattern of surface roughness or any combination thereof, wherein said one or more integrated optical structures are integrated in a sensor channel or reservoir that is a part of said microfluidic network or a sensor channel or reservoir that is in fluid communication with said microfluidic network.

4. The system of claim 1, wherein said optical sensor further comprises a fluorometric sensor, a scattered light sensor, an extinction-based sensor, a chemiluminescence sensor or any combination thereof.

5. The system of claim 4, wherein said optical sensor comprises one or more reactants provided in a sensor reservoir or channel of said microfluidic network or a sensor reservoir or channel in fluid communication with said microfluidic network; wherein interaction between said one or more reactants and said biofluid results in a measureable signal in an optical property of said biofluid or component thereof.

6. The system of claim 5, wherein said one or more reactants are an indicator, a dye, a fluorophore, a chelating agent, or any combination thereof.

7. The system of claim 5, wherein said one or more reactants are immobilized in a matrix in a sensor channel or reservoir or the walls of a sensor channel or reservoir.

8. The system of claim 7, wherein said matrix is a gel, a hydrogel, a coating, particles, a filler, or any combination thereof.

9. The system of claim 7, wherein said one or more reactants are selected from the group consisting of silver chloranilate, $CoCl_2$, glucose oxidase, peroxidase, potassium iodide, lactate dehydrogenase, diaphorase, formazan dyes, 2,4,6-tris(2-pyridinyl)-s-triazine (TPTZ) complexed with mercury ion or iron ion, a 2,2'-bicinchoninic acid, 1,10-phenanthroline, a universal pH indicator, and any combination thereof.

10. The system of claim 4, wherein the fluorometric sensor comprises a microfluidic reservoir and a detachable black light-shielding film provided in a multilayer geometry, wherein the microfluidic reservoir is in fluidic communication with said microfluidic network and wherein the microfluidic reservoir contains one or more fluorophore reagent.

11. The system of claim 1, wherein said optical sensor comprises a channel or reservoir of said microfluidic network or a sensor reservoir or channel in fluid communication with said microfluidic network; wherein said channel or reservoir has an inlet for receiving said biofluid; wherein a reactant is provided proximate to the inlet that provides a change in an optical property upon contact with said biofluid; wherein the position of said biofluid in said channel or reservoir is characteristic of a local rate of said biofluid from the skin of a subject.

12. The system of claim 11, wherein said channel or reservoir has a volume in a range of 1-500 μL.

13. The system of claim 1, wherein said one or more integrated optical structures include one or more indicator layers to provide for visualization of said optical sensor; wherein said indicator layer comprises a scattering media with a refractive index within 20% of said biofluid.

14. The system of claim 1, wherein said one or more integrated optical structures include one or more color reference markers.

15. The system of claim 1, wherein said one or more integrated optical structures include one or more colorimetric temperature sensors comprising a thermochromic liquid crystal layer.

16. The system of claim 1, wherein said one or more parameters of said biofluid are visually observable.

17. The system of claim 1, wherein a signal corresponding to said one or more parameters of said biofluid is transmitted by the NFC electronics module from said system to an external receiving device.

18. The system of claim 1, wherein said one or more parameters is sweat volume, sweat rate, sweat loss or any combination thereof.

19. The system of claim 18, wherein said analyte is an electrolyte, a metabolite, or a biomarker in said biofluid or component thereof.

20. The system of claim 1, wherein said one or more parameters are pH.

21. The system of claim 1, wherein said one or more parameters of said biofluid or a component thereof comprise the presence of, amount or concentration of an analyte in said biofluid or component thereof.

22. The system of claim 1, wherein a leading edge of a volume of said biofluid in a sensor microfluidic channel or reservoir is sensed by said optical sensor as a function of time.

23. The device of claim 22, wherein the lead edge of the volume of said biofluid in said microfluidic channel is sensed visually or measured using a photodetector.

24. The system of claim 1, comprising an epidermal electronic system.

25. The system of claim 1, comprising a wearable electronic system.

26. The system of claim 1, wherein the substrate, said microfluidic network or both are capable of establishing conformal contact with the skin of a human subject.

27. The system of claim 1, wherein the substrate, said microfluidic network or both are characterized by an average Young's Modulus equal to or less than 10 MPa.

28. The system of claim 1, wherein the substrate, said microfluidic network or both are characterized by an average Young's Modulus in a range of 0.5 kPa to 10 MPa.

29. The system of claim 1, wherein the substrate, said microfluidic network or both are characterized by a net bending stiffness less than or equal to 1 nN m.

30. The system of claim 1, wherein the substrate, said microfluidic network or both are characterized by a net bending stiffness in a range of 0.1 to 1 nN m.

31. The system of claim 1, wherein the system has a footprint in a range of 100 mm$^2$ to 1000 cm$^2$.

32. The system of claim 1, wherein said optical sensor comprises a sensor channel or reservoir that is at least partially optically transparent in the visible or infrared region of the electromagnetic spectrum.

33. The system of claim 1, wherein said optical sensor comprises a sensor channel or reservoir characterized by a volume in a range of 1 µm$^3$ to 10000 mm$^3$.

34. The system of claim 1, wherein said NFC electronics module is a multilayer, flexible circuit.

35. The system of claim 1, wherein said NFC electronics module includes an antenna providing for RF power of said system.

36. The system of claim 1, wherein said NFC electronics module provides for one-way or two-way wireless communication to an external receiving or transmitting electronic device.

37. The system of claim 1, wherein said NFC electronics module is at least partially encapsulated in a barrier layer.

38. The system of claim 37, wherein said NFC barrier layer is a moisture barrier.

39. A method of analyzing biofluid from a subject; said method comprising:
  providing a microfluidic system for monitoring said biofluid, comprising:
    a flexible substrate;
    a microfluidic network at least partially embedded in or supported by the substrate;
    a biofluid inlet fluidically connected to said microfluidic network to transport said biofluid from a skin surface to said microfluidic network;
    an optical sensor supported by the substrate and configured to sense one or more parameters of the sweat or a component thereof, said optical sensor including one or more integrated optical structures, wherein said optical sensor comprises a colorimetric sensor; and
    a near-field communication (NFC) electronics module operably connected to support wireless power delivery, wireless data transmission or both to said system;
  contacting the substrate of said system with a surface of the skin of a subject; and
  analyzing said biofluid from said surface of the skin of said subject.

40. The method of claim 39, wherein said biofluid is sweat.

41. The method of claim 39, wherein said subject is a human subject undergoing a diagnostic procedure, a therapeutic procedure, a fitness activity, or monitoring the presence, onset or progression of a disease condition.

* * * * *